(12) United States Patent
Gonsalves et al.

(10) Patent No.: US 7,122,720 B2
(45) Date of Patent: Oct. 17, 2006

(54) SYNTHETIC NUCLEIC ACID MOLECULE FOR IMPARTING MULTIPLE TRAITS

(75) Inventors: Dennis Gonsalves, Hilo, HI (US); Gustavo Alberto Fermin-Munoz, Hilo, HI (US)

(73) Assignee: Cornell Research Foundation, Inc., Ithaca, NY (US)

(*) Notice: Subject to any disclaimer, the term of this patent is extended or adjusted under 35 U.S.C. 154(b) by 349 days.

(21) Appl. No.: 10/131,814

(22) Filed: Apr. 24, 2002

(65) Prior Publication Data

US 2003/0190700 A1   Oct. 9, 2003

Related U.S. Application Data

(60) Provisional application No. 60/286,075, filed on Apr. 24, 2001.

(51) Int. Cl.
*C12N 15/82* (2006.01)
*C12N 5/10* (2006.01)
*C12N 15/90* (2006.01)
*A01H 5/00* (2006.01)
*A01H 5/10* (2006.01)

(52) U.S. Cl. ............ 800/280; 435/320.1; 435/419; 435/468; 435/471; 800/285; 800/301

(58) Field of Classification Search ............ 435/320.1, 435/419, 468, 471; 800/278, 279, 250, 285, 800/282, 288, 301
See application file for complete search history.

(56) References Cited

U.S. PATENT DOCUMENTS

| | | | |
|---|---|---|---|
| 4,818,689 A | 4/1989 | Suciu-Foca et al. | 435/7.1 |
| 5,034,323 A | 7/1991 | Jorgensen et al. | 800/282 |
| 5,175,102 A | 12/1992 | Baulcombe et al. | 800/280 |
| 5,231,020 A | 7/1993 | Jorgensen et al. | 800/286 |
| 5,254,802 A | 10/1993 | Hoekstra et al. | 800/306 |
| 5,283,184 A | 2/1994 | Jorgensen et al. | 800/286 |
| 5,292,362 A | 3/1994 | Bass et al. | 530/350 |
| 5,405,750 A | 4/1995 | Suciu-Foca et al. | 435/7.1 |
| 5,491,084 A | 2/1996 | Chalfie et al. | 435/189 |
| 5,530,196 A | 6/1996 | Fraley et al. | 435/468 |
| 5,569,823 A | 10/1996 | Schreier et al. | |
| 5,571,706 A | 11/1996 | Baker et al. | |
| 5,576,202 A | 11/1996 | Pehu et al. | 435/468 |
| 5,583,021 A | 12/1996 | Dougherty et al. | 435/468 |
| 5,589,612 A | 12/1996 | Jilka et al. | 800/280 |
| 5,589,625 A | 12/1996 | Saarma et al. | 435/468 |
| 5,596,132 A | 1/1997 | Zaitlin et al. | 435/468 |
| 5,741,668 A | 4/1998 | Ward et al. | 435/69.1 |
| 5,773,700 A | 6/1998 | Van Grinsven et al. | 800/280 |
| 5,789,156 A | 8/1998 | Bujard et al. | 435/6 |
| 5,792,922 A | 8/1998 | Moloney | 800/278 |
| 5,866,785 A | 2/1999 | Donson et al. | 800/280 |
| 5,889,190 A | 3/1999 | Donson et al. | 800/288 |
| 5,907,085 A | 5/1999 | Gonsalves et al. | 800/280 |
| 5,939,541 A | 8/1999 | Vance et al. | 536/24.1 |
| 5,939,600 A | 8/1999 | Goldbach et al. | 800/280 |
| 5,998,699 A | 12/1999 | Slightom et al. | 800/280 |
| 5,998,701 A | 12/1999 | Kawchuk et al. | 800/284 |
| 6,002,071 A | 12/1999 | Chappell et al. | 800/298 |
| 6,002,072 A | 12/1999 | McMaster et al. | 800/301 |
| 6,013,864 A | 1/2000 | Mitsky et al. | 800/301 |
| 6,057,492 A | 5/2000 | de Haan | 800/280 |
| 6,153,815 A | 11/2000 | Covello et al. | 800/306 |
| 6,222,096 B1 | 4/2001 | Held et al. | 800/278 |
| 6,222,098 B1 | 4/2001 | Barry et al. | 800/284 |
| 6,225,527 B1 | 5/2001 | Thomas et al. | 800/279 |
| 6,225,532 B1 | 5/2001 | Dixon et al. | 800/301 |
| 6,239,328 B1 | 5/2001 | Thompson | 800/278 |
| 6,239,331 B1 | 5/2001 | Drake et al. | 800/282 |
| 6,242,667 B1 | 6/2001 | Bujard et al. | 800/278 |
| 6,255,560 B1 | 7/2001 | Fraley et al. | 800/278 |

FOREIGN PATENT DOCUMENTS

| | | |
|---|---|---|
| EP | 0 426 195 A1 | 5/1991 |
| EP | 0 558 944 A2 | 9/1993 |
| EP | 0 566 525 A2 | 10/1993 |
| WO | WO 94/16550 | 8/1994 |
| WO | WO 95/09920 | 4/1995 |
| WO | WO 96/21019 | 7/1996 |
| WO | WO 96/21031 | 7/1996 |

(Continued)

OTHER PUBLICATIONS

Voinnet et al., PNAS, 1999, vol. 96, pp. 14174-14152.*

(Continued)

*Primary Examiner*—Ashwin Mehta
(74) *Attorney, Agent, or Firm*—Nixon Peabody LLP

(57) ABSTRACT

The present invention is directed to a DNA construct which includes a modified DNA molecule with a nucleotide sequence which is at least 80%, but less than 100%, homologous to two or more desired trait DNA molecules and which imparts the desired trait to plants transformed with the DNA construct. Each of the desired trait DNA molecules relative to the modified nucleic acid molecule have nucleotide sequence similarity values which differ by no more than 3 percentage points. The DNA construct may further include either a silencer or a plurality of modified DNA molecules. The present invention also relates to host cells, plant cells, transgenic plants, and transgenic plant seeds containing such DNA constructs. The present invention is also directed to a method of preparing a modified nucleic acid molecule suitable to impart multiple traits to a plant, a method of determining whether multiple desired traits can be imparted to plants by a single modified DNA molecule, and a method for imparting traits to plants by transforming the plants with the DNA construct.

91 Claims, 87 Drawing Sheets

FOREIGN PATENT DOCUMENTS

| | | |
|---|---|---|
| WO | WO 97/47754 | 12/1997 |
| WO | WO 98/37223 | 8/1998 |
| WO | WO 99/15682 | 4/1999 |
| WO | WO 00/32785 | 6/2000 |

OTHER PUBLICATIONS

Silva-Rosales et al., Arch. Virol., Apr. 2000, vol. 145, pp. 835-843.*

Pang et al., PNAS, 1997, vol. 94, pp. 8261-8266.* de Haan et al., "Characterization of RNA-Mediated Resistance to Tomato Spotted With Virus in Transgenic Tobacco Plants," *Biotechnology* 10:1133-1137 (1992).

Vaira et al., "Resistance to Tospoviruses in *Nicotiana benthamima* Transformed with the N Gene of Tomato Spotted With Virus Correlation Between Transgene Expression and Protection in Primary Transformants," *MPMI* 8:66-73 (1995).

Prins et al., "Broad Resistance to Tospoviruses in Transgenic Tobacco Plants Expressing Three Tospoviral Nucleoprotein Gene Sequences," *MPMI* 1:85-91 (1995).

Prins et al., "Characterization of RNA-Mediated Resistance to Tomato Spotted Wilt Virus in Transgenic Tobacco Plants Expressing $NS_M$ Gene Sequences," *Plant Molecular Biology* 33:235-243 (1997).

Depicker et al., "Post-Transcription Gene Silencing in Plants," *Curr. Opin. Cell Biol.* 9:373-382 (1997).

Vaucheret, "Identification of a General Silencer for 19S and 35S Promoters in a Transgenic Tobacco Plant: 90 bp of Homology in the Promoter Sequence Are Sufficient for Trans-Inactivation," *C.R. Acad. Sci. Ser. III* 316:1471-1483 (1993).

Simpson et al., "Light-Inducible and Tissue-Specific Pea LHCP Gene Expression Involves an Upstream Element Combining Enhancer-and Silencer-Like Properties," *Nature* (London) 323:551-554 (1986).

Schaeffer et al., "Identification of Enhancer and Silencer Regions Involved in Salt-Responsive Expression of Crassulaccan Acid Metabolism (CAM) Genes in the Facultative Halophyte Mesembryanthemum Crystallinum," *Plant Mol. Biol.* 28:205-218 (1995) (abstract).

Jan et al., "A Minimum Length of N Gene Sequence in Transgenic Plants is Required for RNA-mediated Tospovirus Resistance," *J. Gen. Virol.* 81:235-242 (2000).

[GenBank Accession No. AB044339] Maoka et al., "Reactions of PRSV Resistant Papya Cultivar 'Sun Up' to Japanese Isolates of PRSV and PLDMV," (2000).

[GenBank Accession No. AY027811] Wang et al., "Analyeses of the Coat Protein Genes of Papaya Ringspot Virus W Type Isolated from Different Areas of Taiwan," (2001).

Chuang et al., "Specific and Heritable Genetic Interference by Double-Stranded RNA in *Arabidopsis thaliana*," PNAS97(9):4985-4990 (2000).

Levin et al., Methods of Double-Stranded RNA-Mediated Gene Inactivation in Arabidopsis and Their Use to Define as Essential Gene in Methionine Biosynthesis, *Plant Molecular Biology* 44:759-775 (2000).

Smith et al., "Transgenic Plant Virus Resistance Mediated by Untranslatable Sense RNAs: Expression, Regulation, and Fate of Nonessential RNAs," *The Plant Cell* 6:1441-1453 (1994).

Senior, "Uses of Plant Gene Silencing," *Biotechnology and Genetic Engineering Reviews* 15:79-119 (1998).

Cai et al., "A Protocol For Efficient Transformation and Regeneration of *Carica Papaya* L.," Plant 35:61-69 (1999).

Seymour et al., "Down-Regulation of Two Non-Homologous Endogenous Tomato Genes with a Single Chimaeric Sense Gene Construct," *Plant Molecular Biology* 23:1-9 (1993).

Pang et al., "The Biological Properties of a Distinct Tospovirus and Sequence Analysis of its S RNA," *Phytopathology* 83(7):728-733 (1993).

Pang et al., "Resistance of Transgenic Nicotiana benthamiana Plants to Tomato Spotted Wilt and Impatiens Necrotic Spot Tospoviruses: Evidence of Involvement of the N Protein and N Gene RNA in Resistance," *Phytopathology* 84(3):243-249 (1994).

Voinnet et al., "Systemic Signalling in Gene Silencing," *Nature* pp.553 (1997).

Tanzer et al., "Characterization of Post-Transcriptionally Suppressed Transgene Expression That Confers Resistance to Tobaccos Etch Virus Infection in Tobacco," *The Plant Cell* 9:1411-1423 (1997).

Taylor, "Comprehending Cosuppression," *The Plant Cell* 9:1245-1249 (1997).

Ratcliff et al., "A Similarity Between Viral Defense and Gene Silencing in Plants," *Science* 276:1558-1563 (1997).

Jorgensen, "Altered Gene Expression in Plants Due to Trans Interactions Between Homologous Genes," *TIBTECH* 8:340-344 (1990).

Grierson et al., "Does Co-Suppression of Sense Genes in Transgenic Plants Involve Antisense RNA?" *TIBTECH* 9:122-123 (1991).

Hellwald et al., "Viral RNA as a Potential Target for Two Independent Mechanisms of Replicase-Mediated Resistance Against Cucumber Mosaic Virus," *Cell* 83:937-946 (1995).

Angell et al., "Consistent Gene Silencing in Transgenic Plants Expressing a Replicating Potato Virus X RNA," *EMBO Journal* 16(12):3675-3684 (1997).

Pang et al., "Resistance to Heterologous Isolates of Tomato Spotted Wilt Virus in Transgenic Tobacco Expressing Its Nucleocapsid Protein Gene," *Mol. Plant Pathology* 82(10):1223-1229 (1992).

Pang et al., "Different Mechanisms Protect Transgenic Tobacco Against Tomato Spotted Wilt Virus and Impatiens Necrotic Spot Tospoviruses," Bio/Technology 11(7):819-824 (1993).

Gonsalves et al., "Developing Transgenic Crops That Are Resistant to Tospoviruses," *Acta Horticulturao* 431:427-431 (1997).

Pang et al., "Post-Transcriptional Transgene Silencing and Consequent Tospovirus Resistance in Transgenic Lettuce are Affected By Transgene Dosage and Plant Development," *The Plant Journal* 9(6):899-909 (1996).

Epel et al., "Plant Virus Movement Protein Dynamics Probed with a GFP-Protein Fusion," *Gene* 173:75-79 (1996).

Lawson et al., "Engineering Resistance to Mixed Virus Infection in a Commercial Potato Cultivar: Resistance to Potato Virus X and Potato Virus Y in Transgenic Russet Burbank," *Bio/Technology* 8:127-134 (1990).

van der Krol et al., "Inhibition of Flower Pigmentation by Antisense CHS Genes: Promoter and Minimal Sequence Requirements for the Antisense Effect," *Plant Molecular Biology* 14:457-466 (1990).

Blokland et al., "Transgene-Mediated Suppression of Chalcone Synthase Expression in *Petunia hybrida* Results from an Increase in RNA Turnover," *The Plant Journal* 6(6):861-877 (1994).

Tennant et al., "Differential Protection Against Papays Ringspot Virus Isolates in Coat Protein Gene Transgenic Papay and Classically Cross-Protected Papayq," *The American Phytopathological Society* 84(11):1359-1366 (1994).

Fitch et al., "Virus Resistant Papayq Plants Derived from Tissues Bombarded with the Coat Protein Gene of Papayq Ringspot Virus," *Bio/Technology* 10:1466-1472 (1992).

* cited by examiner

A
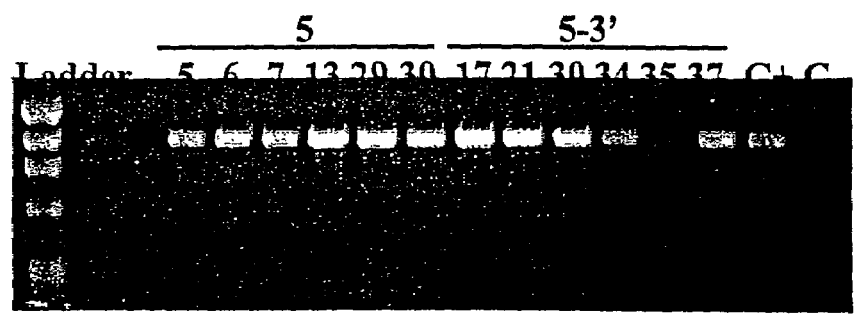
B
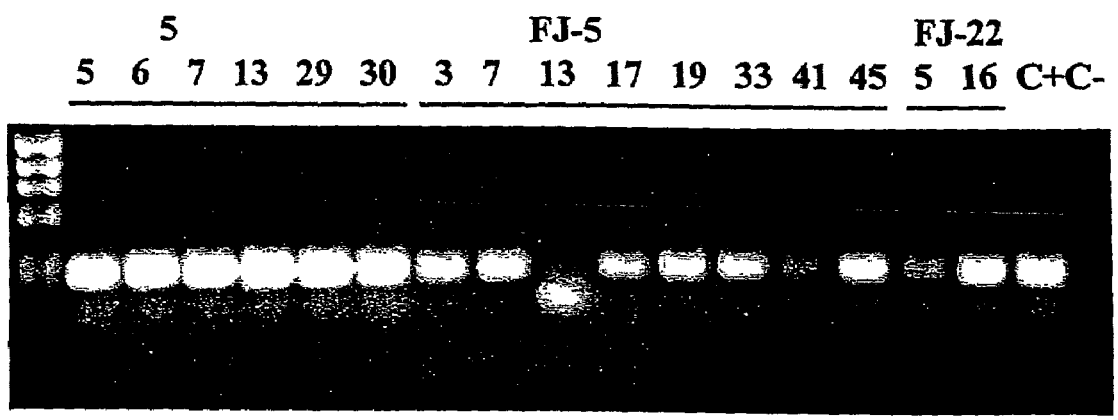
FIGURE 4

| | | | | | |
|---|---|---|---|---|---|
| Rec2 | GCAAAATCTG | TGAGACTTGC | CATAATGCTG | GGAGGTAGTA | TCCCTCTTAT (SEQ ID NO: 4) |
| TSWV | GCAAAgTCTG | TGAGgCTTGC | CATAATGCTG | GGAGGTAGct | TaCCTCTTAT (SEQ ID NO: 1) |
| GRSV | GCAAAATCTG | TGAGACTTGC | CATAATGCTt | GGAGGTAGTA | TCCCTCTcAT (SEQ ID NO: 2) |
| TCSV | GCAAAgTCTG | TaAGgCTTGC | CATAATGCTa | GGAGGTAGTA | TCCCTCTgAT (SEQ ID NO: 3) |
| | | | | | |
| Rec2 | TGCTTCTGTT | GACAGCTTTG | AAATGATCAG | TGTTGTCCTT | GCTATATATC |
| TSWV | TGCTTCaGTT | GAtAGCTTTG | AgATGATCAG | TGTTGTCtTg | GCTATATATC |
| GRSV | TGCTTCTGTT | GACAGtCTcG | AAATGATCAG | TGTTGTtCTT | GCcATATATC |
| TCSV | TGCTTCTGTg | GtCAGCTTTG | AAATGATCAG | caTcaTCCTT | GCcATATAaC |
| | | | | | |
| Rec2 | AAGAT-GCAA | AATACAAGGA | TCTCGGGATT | GAACCAACGA | AGTATAACAC |
| TSWV | AgGAT-GCAA | AATACAAGGA | TCTCGGGATc | GAcCCAAaGA | AGTATgACAC |
| GRSV | AAGATaGtcA | AgTACAgGag | T-TaGGGATT | GAACCAACtA | AGTAcAACAC |
| TCSV | AAGAT-GCtA | AATAtAAaGA | TCTtGGaATT | GAACCttCGA | AGTATAACAC |
| | | | | | |
| Rec2 | TAAGGAAGCC | TTAGGAAAAG | TTTGCACTGT | GCTGAAAAGC | AAAGGATTTA |
| TSWV | cAgGGAAGCC | TTAGGAAAAG | TTTGCACTGT | GCTGAAAAGa | AAAGcATTTg |
| GRSV | TAAGGAAGCt | cTgGGgAagG | TTTGCACTGT | GCTGAAAAGC | AAAGGATTTA |
| TCSV | TAAaGAAGCt | TTAGGAAAAG | TcTGCACTGT | GCTGAAAAGC | AAAGGATTTA |
| | | | | | |
| Rec2 | CAATGGATGA | AGATCAG | | | |
| TSWV | aAATGaATGA | AGATCAG | | | |
| GRSV → | CAATGGATGA | tGcaCAa | | | |

FIGURE 6

|  |  |  |
|---|---|---|
| (SEQ ID NO: 5) | Sync-Con | GCTAGATATG CTTTCGACTT CTATGAGGTG AATTCGAAAA CACCTGATATAG GGCTCGTGAA |
| (SEQ ID NO: 6) | TH-Con   | GCTAGATATG CTTTCGACTT CTATGAGGTG AAcTCaAAAA CACCTGATAG GGCTCGTGAA |
| (SEQ ID NO: 7) | KE-con   | GCTAGATATG CTTTCGACTT CTATGAGGTG AATTCGAAAA CACCTGATAG GGCTCGgGAA |
| (SEQ ID NO: 8) | YK-Con   | GCTAGATATG CTTTCGA(TT CTATGAGGTG AATTCGAAAA CACCTGATAG GGCTCGTGAA |

|  |  |  |
|---|---|---|
| (SEQ ID NO: 5) | Sync-Con | GCTCATATGC AGATGAAGGC TGCAGGGCTG CGCAACACTA ATCGCAGAAT GTTTGGAATG |
| (SEQ ID NO: 6) | TH-Con   | GCTCATATGC AGATGAAGGC TGCAGCGCTG CGCAACACTg ATCGCAGAAT GTTTGGAATG |
| (SEQ ID NO: 7) | KE-Con   | GCcCAcATGC AGATGAAGGC TGCAGCGCTG CGa.AACACTA gTCGCAGAAT GTTTGGAtG |
| (SEQ ID NO: 8) | YK-Con   | GCTCATATGC AGATGAAGGC TGCAGCGCTa CGCAAtACTA ATCGCAaAAT GTTTGGAATG |

|  |  |  |
|---|---|---|
| (SEQ ID NO: 5) | Sync-Con | GACGGCAGTG TTAGTAACAA GGAAGAAAAC ACGGAGAGAC ACACAGTGGA AGATGTCAAT |
| (SEQ ID NO: 6) | TH-Con   | GACGGCAGTG TCAGTAACAA GGAAGAAAAC ACGGAGAGAC ACACAGTGA AGATGTCAAC |
| (SEQ ID NO: 7) | KE-Con   | GACGGCAGTG TTAGTAACAA GGAAGAAAAC ACGGAGAGAC ACACAGTGGA AGATGTCAAT |
| (SEQ ID NO: 8) | YK-Con   | GACGGCAGTG TcAGTAACAA GGAAGAAAAC ACGGAGAGAC ACACAGTGGA AGATGTCAAe |

|  |  |  |
|---|---|---|
| (SEQ ID NO: 5) | Sync-Con | AGAGACATGC ACTCTCTCCT GGG |
| (SEQ ID NO: 6) | TH-Con   | AGAGACATGC ACTCTCTCCT aGG |
| (SEQ ID NO: 7) | KE-Con   | AGAGACATGC ACTCTCTCCT GGG |
| (SEQ ID NO: 8) | YK-Con   | AGAGACATGC ACTCTCTCCT GGG |

FIGURE 7

|  | | |
|---|---|---|
| (SEQ ID NO: 9) | Sync-Var | TGCTGGTCTG AATGAGAAGC TCAAAGAGAA AGAAAAACAG AAAAAAACAG AAAGAAAAAG AAAAAGATAA |
| (SEQ ID NO: 10) | TH-Var | TGCTGGTCTt AATGAGAAGT TCAAAGAGAt AA AGAAAAACAG AAAGA---AG AAAAAGATAA |
| (SEQ ID NO: 11) | KE-Var | TGCTGGTtTG AATGAaAAaC TCAAAGAGAA AGAAAAACAG AAAGAAAAAG AAAAGAaAA |
| (SEQ ID NO: 12) | YK-Var | TaCcGGTCTG AATGAGAAGC TCAAAGAaAA AGAAAAACAG AAAGAAAAAG AAAAAGATAA |
| | | |
| (SEQ ID NO: 9) | Sync-Var | ACAAAAAGAT AAAGAAAAATG ATGAAGCTAG TGACGGAAAT GATGTGTCAA CTAGCACAAA |
| (SEQ ID NO: 10) | TH-Var | ACAAAAAGgT AAAGAAAATA ATGAAGCTAG TGACGGAAAT GATGTGTCAA CTAGCACAAA |
| (SEQ ID NO: 11) | KE-Var | ACAAAAAGAa AAAGgaAAaG AtGAtGCTAG TGACgGAAAT GATGTGTCAA CTAGCACAAA |
| (SEQ ID NO: 12) | YK-Var | ACAAcAAGAT AAAGaCAATG ATGgAGCTAG TGACGGAAAc GATGTGTCAA CTAGCACAAA |
| | | |
| (SEQ ID NO: 9) | Sync-Var | AACTGGAGAG AGAGATAGAG ATGTCAATGC TGGAACTAGT GGAACTTTCA CTGTTCCGAG |
| (SEQ ID NO: 10) | TH-Var | ACTGGAGAG AGAGATAGAG ATGTCAATGC c GGAACTAGT GGtACTTTCA CTGTTCCGAG |
| (SEQ ID NO: 11) | KE-Var | AACTGGAGAG AGAGATAGAG ATGTCAATGt TGGGACcAGT GGAACTTTCg CTGTTCCGAG |
| (SEQ ID NO: 12) | YK-Var | AACTGGAGAG AGAGATAGgG ATGTCAATGC cGGAACTAGT GGAACcTTCA CTGTTCCGAG |
| | | |
| (SEQ ID NO: 9) | Sync-Var | GATAAAATCA TTTACTGATA AGTTGATTT |
| (SEQ ID NO: 10) | TH-Var | aATAAAATtA TTTACtGAcA AGaTGATTT |
| (SEQ ID NO: 11) | KE-Var | aATtAAATCA TTTACTGATA AGTTGATTc |
| (SEQ ID NO: 12) | YK-Var | GATAAAgTCA TTTACTGATA AGaTGATcT |

FIGURE 8

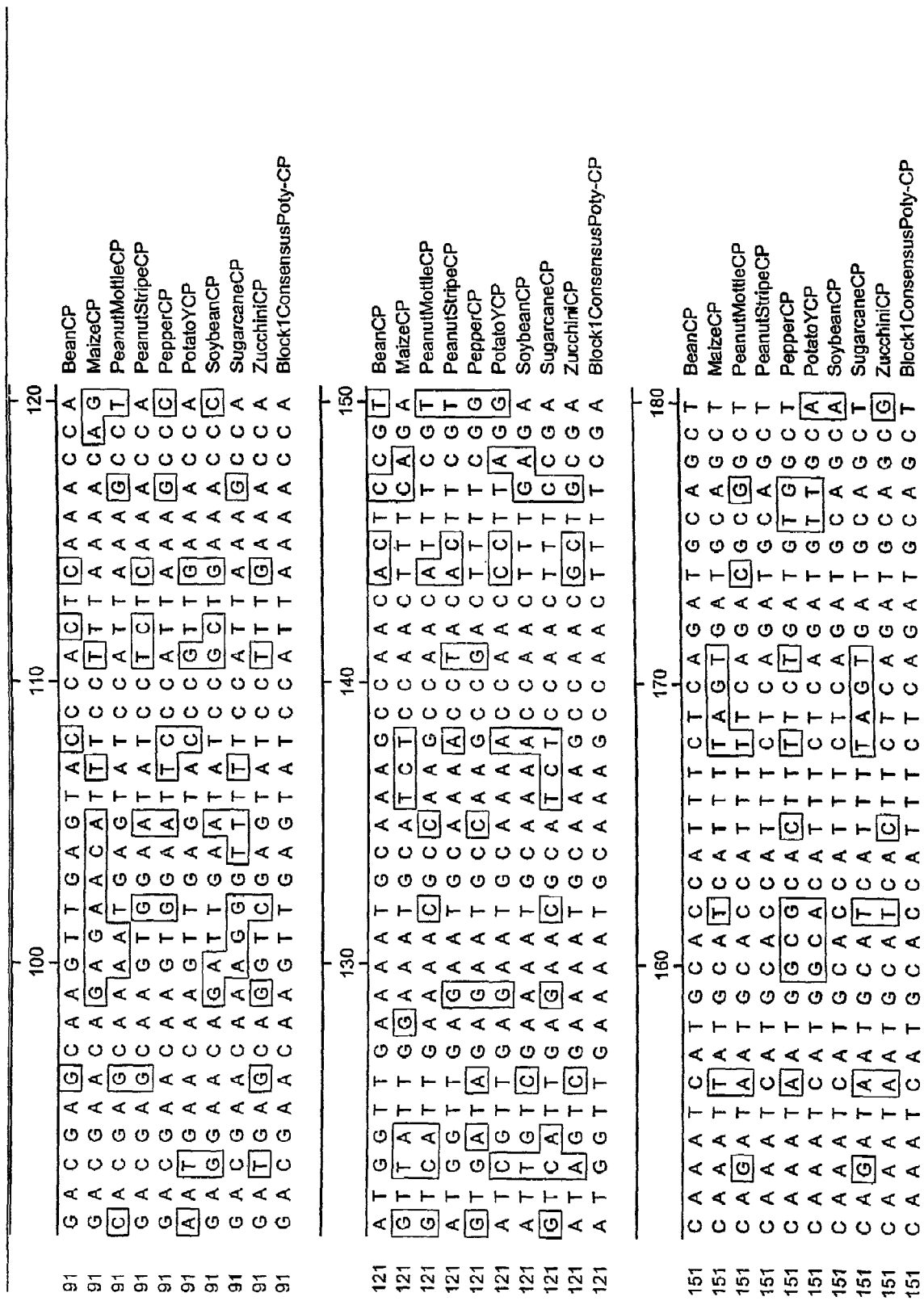
FIGURE 9 (Con't.)

|     |   |   |   |   |   |   |   |   |   |   | 190 |   |   |   |   |   |   |   |   | 200 |   |   |             |
|-----|---|---|---|---|---|---|---|---|---|---|-----|---|---|---|---|---|---|---|---|-----|---|---|-------------|
| 181 | G | A | A | G | C | A | T | T | A | C | A   | T | T | G | A | G | A | T | G | A   | G | A | BeanCP |
| 181 | G | A | A | G | C | A | T | T | A | C | A   | T | T | G | A | G | A | T | A | A   | G | A | MaizeCP |
| 181 | G | A | A | G | C | A | G | T | A | C | A   | T | T | G | A | G | A | T | A | T   | G | A | PeanutMottleCP |
| 181 | G | A | A | G | C | A | T | T | A | C | T   | T | T | G | A | G | A | T | A | T   | G | A | PeanutStripeCP |
| 181 | G | A | A | G | C | A | T | T | A | C | T   | T | T | A | G | A | A | T | G | C   | G | C | PepperCP |
| 181 | G | A | A | G | C | A | G | T | T | C | A   | T | A | G | A | G | A | T | G | C   | G | C | PotatoYCP |
| 181 | G | A | A | G | C | A | T | T | A | C | A   | T | T | A | G | A | A | T | G | A   | G | A | SoybeanCP |
| 181 | G | A | A | G | C | A | G | T | A | C | T   | T | T | G | A | G | A | T | A | C   | G | C | SugarcaneCP |
| 181 | G | A | A | G | C | A | T | T | A | C | A   | T | T | G | A | G | A | T | G | A   | G | A | ZucchiniCP |
| 181 | G | A | A | G | C | A | T | T | A | C | A   | T | T | G | A | G | A | T | G | A   | G | A | Block1ConsensusPoty-CP |

Decoration 'Decoration #1': Box residues that differ from Block1ConsensusPoty-CP.

FIGURE 9 (Con't.)

FIGURE 10

FIGURE 10 (Con't)

```
                              190                           200
181  G A G G C A T A C A T T G A G A T G A G A A   BeanCP
181  G A A G C A T A C A T T G A G A T G A G A A   Block1ConsensusPoty-CP
181  G A A G C T T A C A T A G A G T A G A G C A   Block1SyncPoty-CP
181  G A A G C A T A C A T T G A G T A T A G A A   MaizeCP
181  G A G G C G T A C A T T G A G A T G A G A A   PeanutMottleCP
181  G A A G C A T A C A T T G A G A T G A G A A   PeanutStripeCP
181  G A G G C A T A T A T A G A A A T G C G C A   PepperCP
181  G A A G C G T A T A T A G A A A T G C G C A   PotatoYCP
181  G A A G C T T A C A T T G A G A T G A G A A   SoybeanCP
181  G A A G C G T A T A T A G A G T A C C G A A   SugarcaneCP
181  G A G G C A T A C A T A G A A A T G A G A A   ZucchiniCP
```

Decoration 'Decoration #1': Box residues that differ from Block1SyncPoty-CP.

FIGURE 10 (Con't)

FIGURE 11

FIGURE 11 (Con't)

FIGURE 12 (Con't)

| | | | | | | | | | | | |
|---|---|---|---|---|---|---|---|---|---|---|---|
| 121 | G | T | C | C | T | T | G | T | T | T | G | Petunia |
| 121 | G | T | A | C | T | T | G | T | G | T | G | PetuniaCHSB |
| 121 | G | T | C | C | T | T | G | T | T | T | G | PetuniaCHSD |
| 121 | G | C | C | C | T | T | G | C | T | T | G | PetuniaCHSF |
| 121 | G | T | C | C | T | T | G | T | T | T | G | PetuniaCHSG |
| 121 | G | T | C | C | T | T | G | T | T | T | G | PetuniaCHSJ |
| 121 | G | T | C | C | T | T | G | T | T | T | G | PetuniaConsensus |

Decoration 'Decoration #1': Box residues that differ from PetuniaConsensus.

FIGURE 13 (Con't.)

FIGURE 14

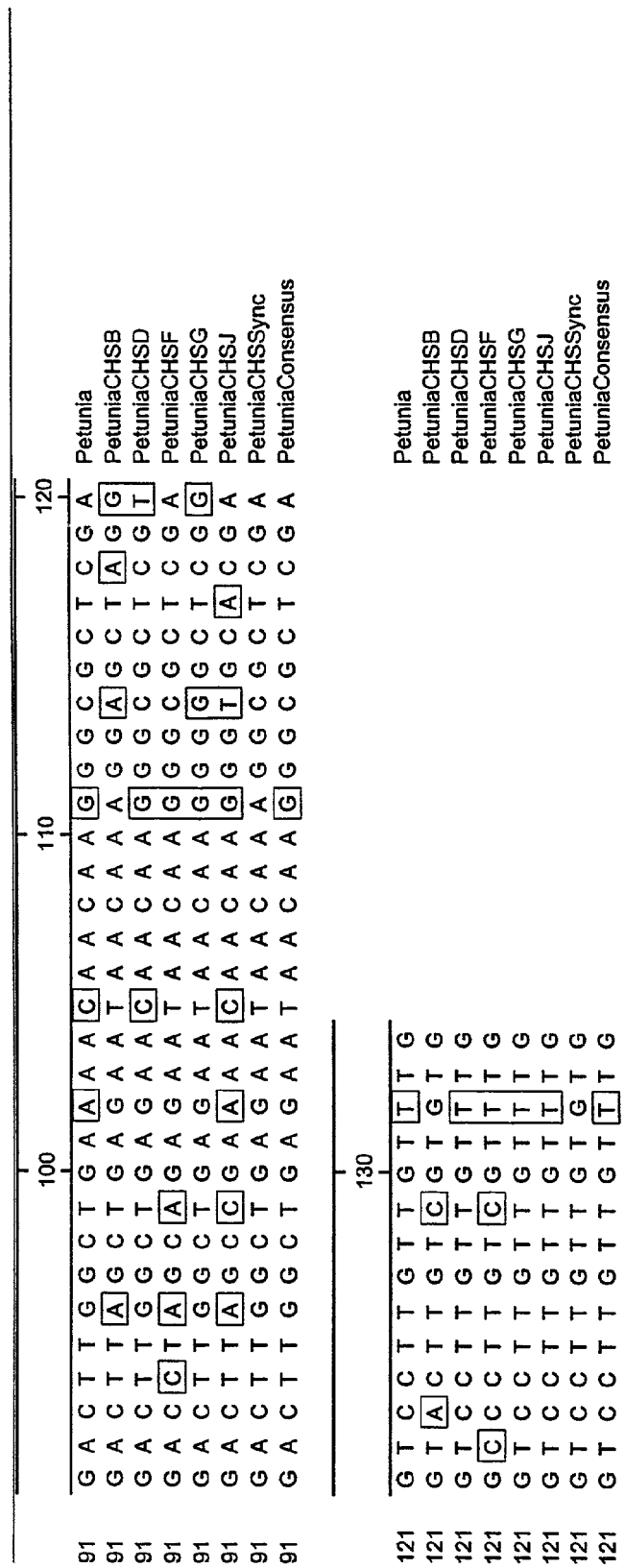
FIGURE 14 (Con't.)

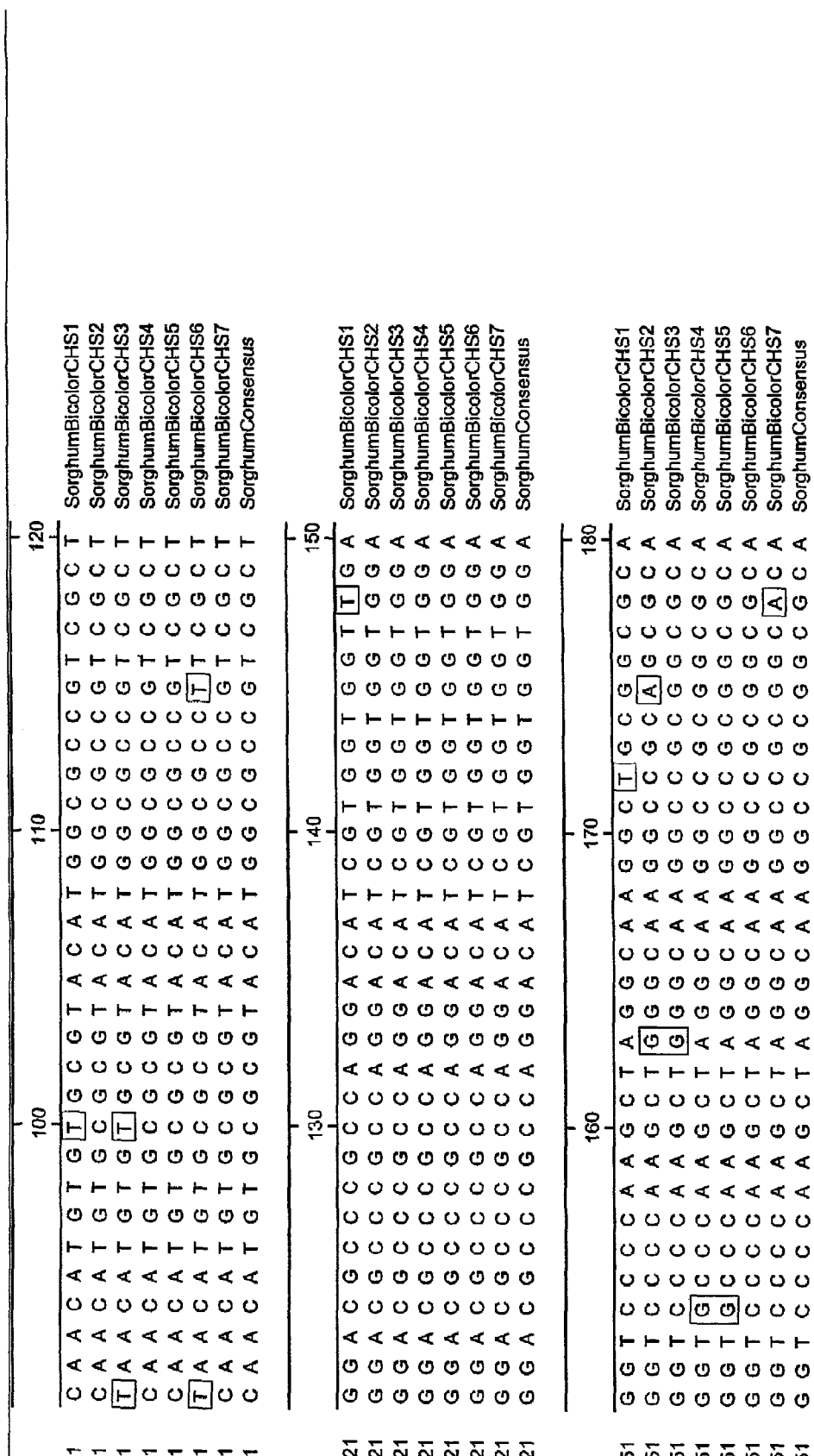
FIGURE 15 (Con't)

FIGURE 15 (Con't)

| | | 280 | | | | | 290 | | |
|---|---|---|---|---|---|---|---|---|---|
271 C T A C C A G C T C A C C A A A G A T G C T  SorghumBicolorCHS1
271 C T T A C C A G C T C A C C A A A G A T G C T  SorghumBicolorCHS2
271 C T T A C C A G C T C A C C A A A G A T G C T  SorghumBicolorCHS3
271 C T T A C C A G C T C A C C A A A G A T G C T  SorghumBicolorCHS4
271 C T T A C C A G C T C A C C A A A G A T G C T  SorghumBicolorCHS5
271 C T T A C C A G C T C A C C A A A G A T G C T  SorghumBicolorCHS6
271 C T T A C C A G C T C A C C A A A G A T G C T  SorghumBicolorCHS7
271 C T A C C A G C T C A C C A A A G A T G C T  SorghumConsensus Decoration 'Decoration #1': Box residues that differ from SorghumConsensus.

FIGURE 15 (Con't)

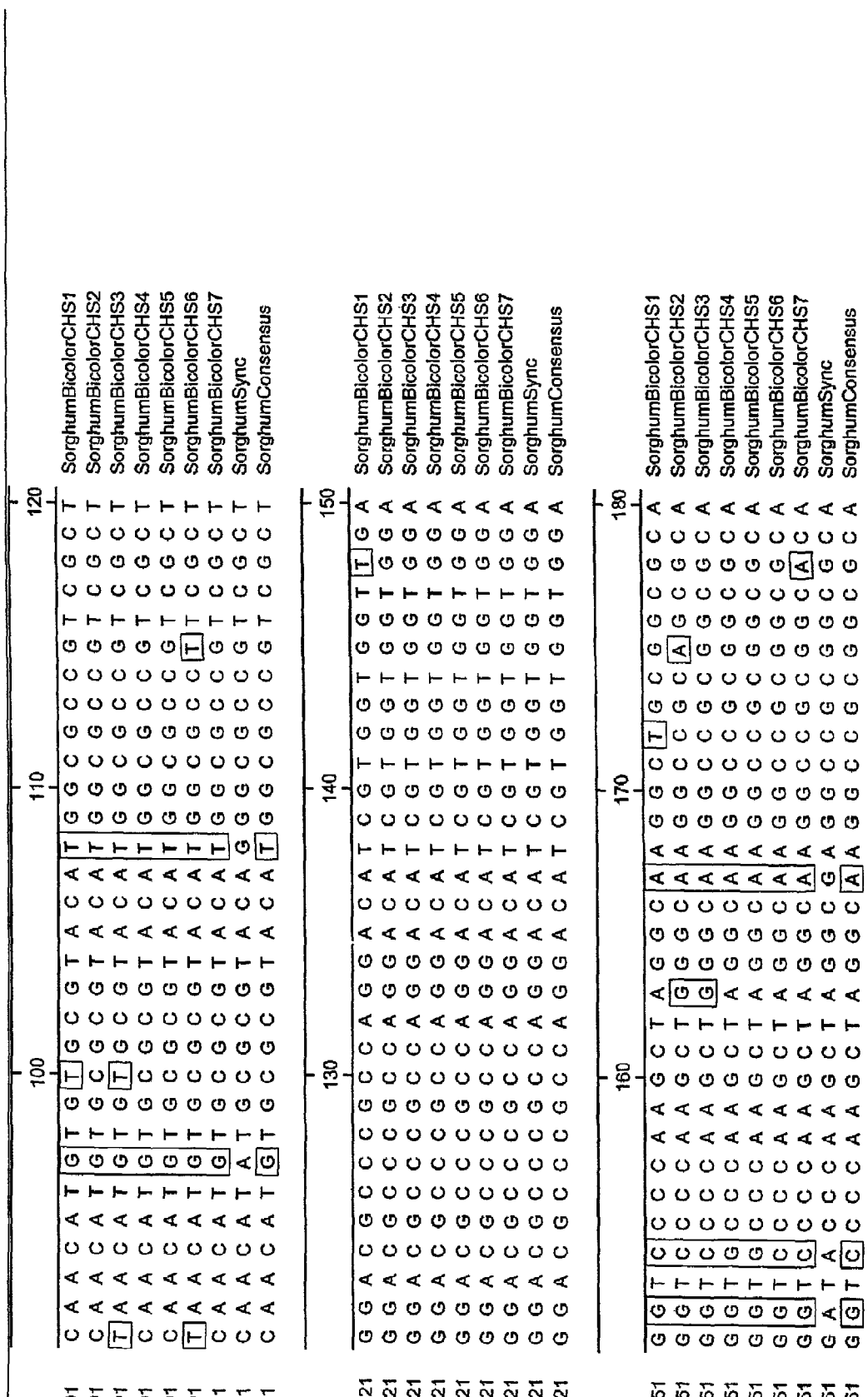
FIGURE 16 (Con't)

FIGURE 16 (Con't)

| | | | | | 280 | | | | | | 290 | | |
|---|---|---|---|---|---|---|---|---|---|---|---|---|---|
| 271 | C | T | A | C | C | T | C | A | C | A | A | G | A | T | G | C | T | SorghumBicolorCHS1 |
| 271 | C | T | A | C | C | T | C | A | C | A | A | G | A | T | G | C | T | SorghumBicolorCHS2 |
| 271 | C | T | A | C | C | T | C | A | C | A | A | G | A | T | G | C | T | SorghumBicolorCHS3 |
| 271 | C | T | A | C | C | T | C | A | C | A | A | G | A | T | G | C | T | SorghumBicolorCHS4 |
| 271 | C | T | A | C | C | T | C | A | C | A | A | G | A | T | G | C | T | SorghumBicolorCHS5 |
| 271 | C | T | A | C | C | T | C | A | C | A | A | G | A | T | G | C | T | SorghumBicolorCHS6 |
| 271 | C | T | A | C | C | T | C | A | C | A | A | G | A | T | G | C | T | SorghumBicolorCHS7 |
| 271 | C | T | A | C | C | T | C | A | T | A | A | G | A | T | G | C | T | SorghumSync |
| 271 | C | T | A | C | C | T | C | A | C | A | A | G | A | T | G | C | T | SorghumConsensus |

Decoration 'Decoration #1': Box residues that differ from SorghumSync.

FIGURE 16 (Con't)

FIGURE 17

FIGURE 17 (Con't)

FIGURE 17 (Con't)

FIGURE 17 (Con't)

FIGURE 17 (Con't)

FIGURE 17 (Con't)

FIGURE 17 (Con't)

FIGURE 17 (Con't)

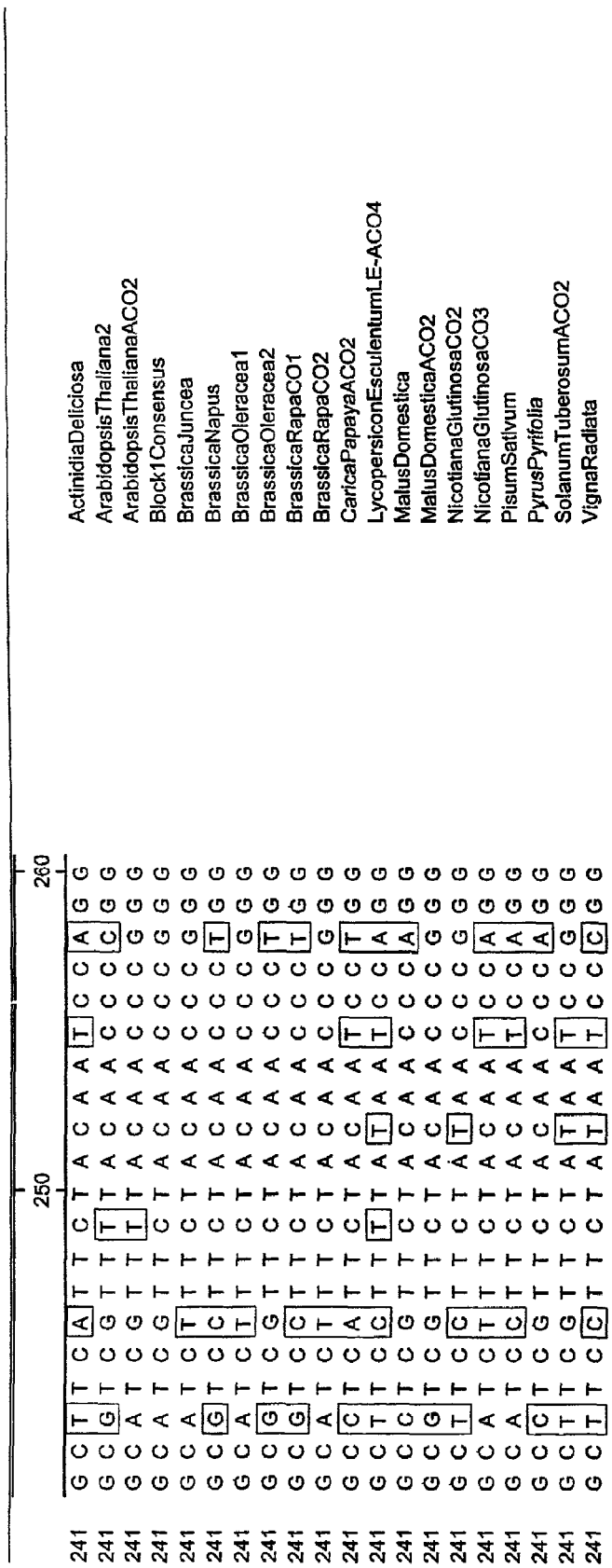
FIGURE 17 (Con't)

FIGURE 18

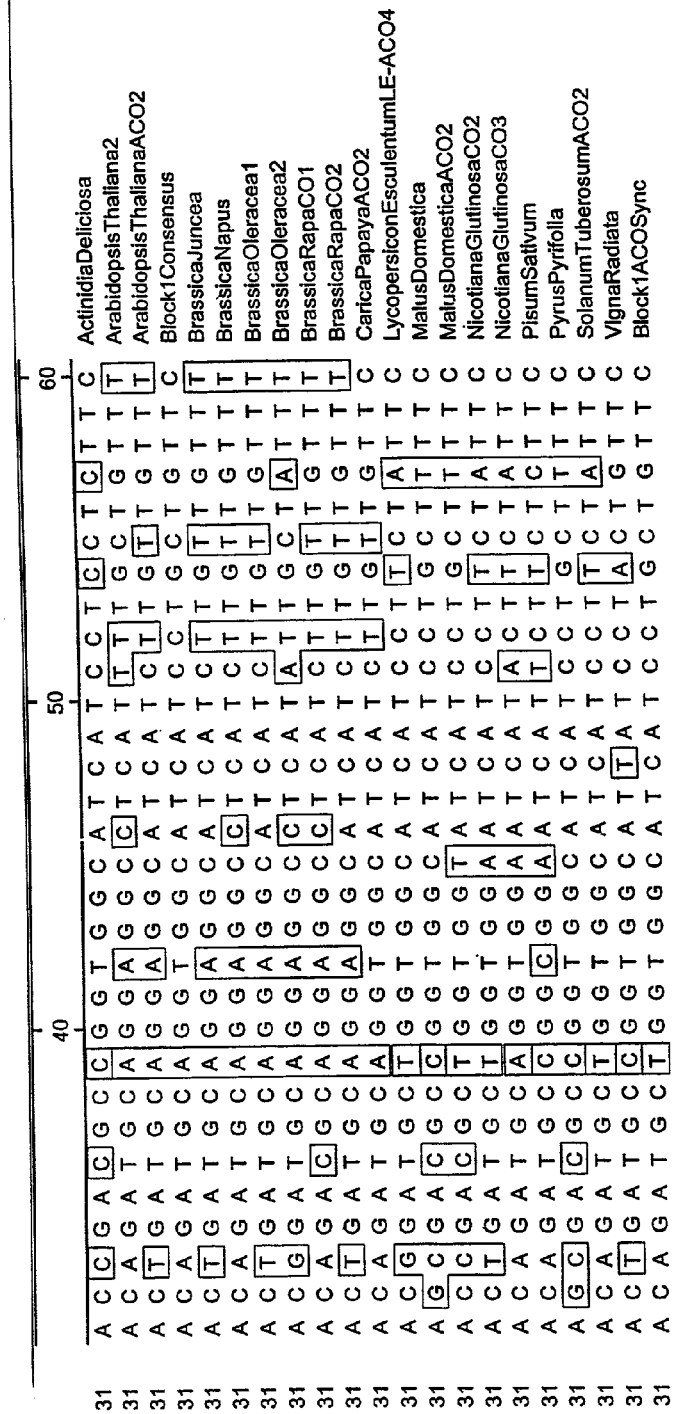
FIGURE 18 (Con't)

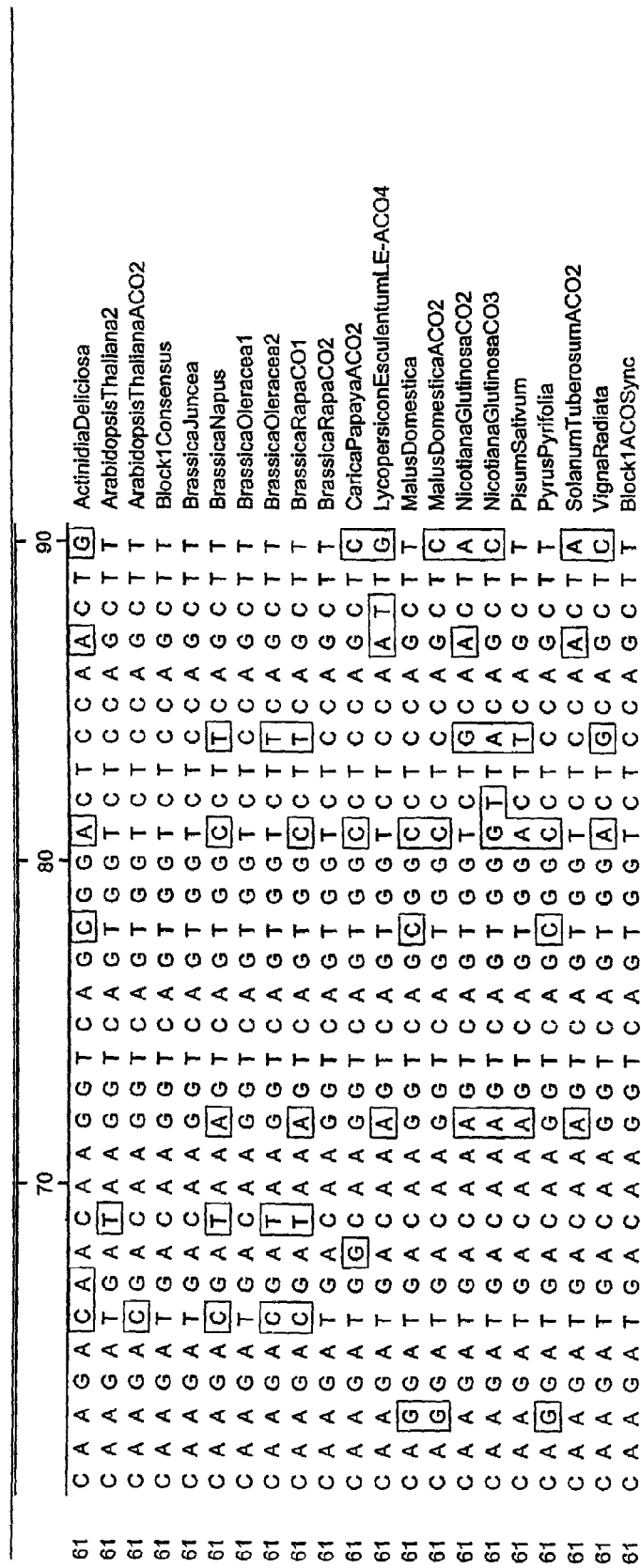
FIGURE 18 (Con't)

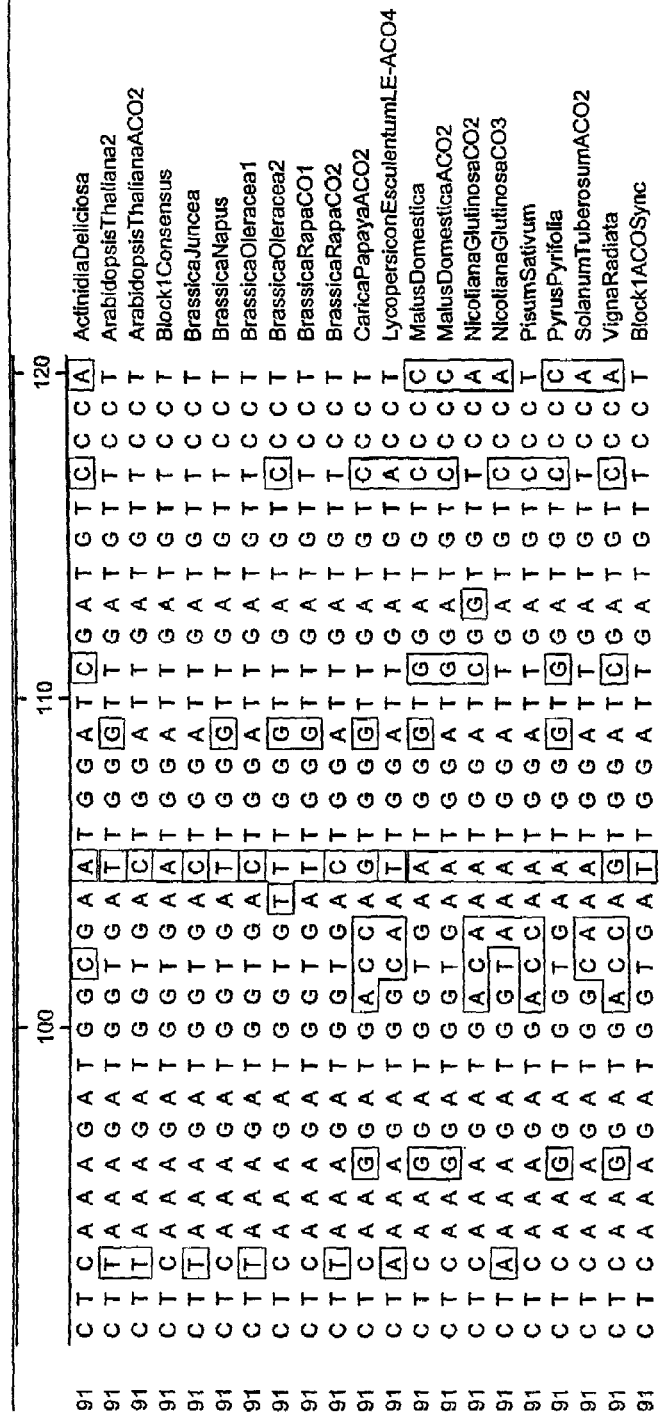
FIGURE 18 (Con't)

FIGURE 18 (Con't)

FIGURE 18 (Con't)

FIGURE 18 (Con't)

FIGURE 18 (Con't)

FIGURE 18 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

FIGURE 19 (Con't)

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 181 | A | G | A | A | C | A | T | T | G | C | C | A | C | T | C | T | T | C | G | G | G | T | A | T | G | G | C | | PRSV-CP-AusHawSync |
| 181 | A | G | A | A | C | A | T | T | G | C | C | A | C | T | C | T | T | C | G | G | G | T | A | T | G | G | C | | ConsensusForAmericaSync |
| 181 | A | G | A | A | C | A | T | T | G | C | C | A | C | T | C | T | T | C | G | G | G | T | A | T | G | G | C | | PRSV-CP-AmericaSync |
| 181 | A | G | A | A | C | A | T | T | G | C | C | A | C | T | C | T | T | C | G | G | G | T | A | T | G | G | C | | PRSV-CP-AsiaSync |
| 181 | A | G | A | A | C | A | T | T | G | C | C | A | C | T | C | T | T | C | G | G | G | T | A | T | G | G | C | | ConsensusForAsiaSync |
| 181 | A | G | A | A | C | A | T | T | G | C | C | A | C | T | C | T | T | C | G | G | G | T | A | T | G | G | C | | PRSV-CP-UniversalSync |
| 211 | A | A | C | T | G | A | | | | | | | | | | | | | | | | | | | | | | | | Australia-Bridgeman_Downs_trimmedSVU |
| 211 | A | A | C | T | G | A | | | | | | | | | | | | | | | | | | | | | | | | Australia-Bundaberg_trimmedSVU |
| 211 | A | A | C | T | G | A | | | | | | | | | | | | | | | | | | | | | | | | Australia-PRSV-P_trimmedSVU |
| 211 | A | A | C | T | G | A | | | | | | | | | | | | | | | | | | | | | | | | Australia-Wellington_Point_trimmedSVU |
| 211 | A | A | C | T | G | A | | | | | | | | | | | | | | | | | | | | | | | | Brasil(Geneva)_trimmedSVU |
| 211 | A | A | C | T | G | A | | | | | | | | | | | | | | | | | | | | | | | | Brasil-Bahia-Itabela1-P_trimmedSVU |
| 211 | A | A | C | T | G | A | | | | | | | | | | | | | | | | | | | | | | | | Brasil-Bahia-Itabela2-P_trimmedSVU |
| 211 | A | A | C | T | G | A | | | | | | | | | | | | | | | | | | | | | | | | Brasil-BahiaCrizDasAlmas-P_trimmedSVU |
| 211 | A | A | C | T | G | A | | | | | | | | | | | | | | | | | | | | | | | | Brasil-Brasilia-P_trimmedSVU |
| 211 | A | A | C | T | G | A | | | | | | | | | | | | | | | | | | | | | | | | Brasil-Ceara-P_trimmedSVU |
| 211 | A | A | C | T | G | A | | | | | | | | | | | | | | | | | | | | | | | | Brasil-EspiritoSanto-P_trimmedSVU |
| 211 | A | A | C | T | G | A | | | | | | | | | | | | | | | | | | | | | | | | Brasil-Paraiba-P_trimmedSVU |
| 211 | A | A | C | T | G | A | | | | | | | | | | | | | | | | | | | | | | | | Brasil-Parana-P_trimmedSVU |
| 211 | A | A | C | T | G | A | | | | | | | | | | | | | | | | | | | | | | | | Brasil-Pernambuco-P_trimmedSVU |
| 211 | A | A | C | T | G | A | | | | | | | | | | | | | | | | | | | | | | | | Brasil-SaoPaulo-P_trimmedSVU |
| 211 | A | A | T | C | G | A | | | | | | | | | | | | | | | | | | | | | | | | China-severe_trimmedSVU |
| 211 | A | A | C | T | G | A | | | | | | | | | | | | | | | | | | | | | | | | China_Xiao_trimmedSVU |
| 211 | A | A | C | T | A | A | | | | | | | | | | | | | | | | | | | | | | | | FloridaH1K_trimmedSVU |
| 211 | A | A | T | T | A | A | | | | | | | | | | | | | | | | | | | | | | | | Hawaii-KEAAU(Geneva)_trimmedSVU |
| 211 | A | A | C | T | A | A | | | | | | | | | | | | | | | | | | | | | | | | Hawaii-OAHU(Geneva)_trimmedSVU |
| 211 | A | A | T | T | A | A | | | | | | | | | | | | | | | | | | | | | | | | Hawaii_trimmedSVU |
| 211 | A | A | C | T | G | A | | | | | | | | | | | | | | | | | | | | | | | | India-Bangalore_trimmedSVU |
| 211 | A | A | C | T | G | A | | | | | | | | | | | | | | | | | | | | | | | | India-Chiengmai1_trimmedSVU |
| 211 | A | A | C | T | G | A | | | | | | | | | | | | | | | | | | | | | | | | India-Chiengmai2_trimmedSVU |
| 211 | A | A | C | T | G | A | | | | | | | | | | | | | | | | | | | | | | | | India-PRSV-P_trimmedSVU |
| 211 | A | A | T | T | G | A | | | | | | | | | | | | | | | | | | | | | | | | India-Ratchaburi_trimmedSVU |
| 211 | A | A | T | T | G | A | | | | | | | | | | | | | | | | | | | | | | | | Indonesia1_trimmedSVU |
| 211 | A | A | T | T | G | A | | | | | | | | | | | | | | | | | | | | | | | | Indonesia2_trimmedSVU |
| 211 | A | A | T | T | G | A | | | | | | | | | | | | | | | | | | | | | | | | JAMAICA(Geneva)_trimmedSVU |
| 211 | A | A | C | T | G | A | | | | | | | | | | | | | | | | | | | | | | | | Japan-Okinawa_Maoka_trimmedSVU |
| 211 | A | A | C | T | G | A | | | | | | | | | | | | | | | | | | | | | | | | Japan-PRSV-S_trimmedSVU |
| 211 | A | A | C | T | G | A | | | | | | | | | | | | | | | | | | | | | | | | Japan_Hanada_trimmedSVU |
| 211 | A | A | C | T | G | A | | | | | | | | | | | | | | | | | | | | | | | | Malaysia_Maoka_trimmedSVU |

FIGURE 19 (Con't)

FIGURE 19 (Con't)

| | | | | | | |
|---|---|---|---|---|---|---|
| 211 | A | A | T | T | G | A | Thailand-KPS_trimmedSVU |
| 211 | A | A | T | T | G | A | Thailand-LabMild_trimmedSVU |
| 211 | A | A | T | T | G | A | Thailand-LabSevere_trimmedSVU |
| 211 | A | A | T | T | G | A | Thailand_Maoka_trimmedSVU |
| 211 | A | A | T | T | G | A | Thailand_trimmedSVU |
| 211 | A | A | C | T | [A] | A | Venezuela-El-Vigia(Geneva)_trimmedSVU |
| 211 | A | A | C | T | G | A | ConsensusForSyncAusHaw |
| 211 | A | A | C | T | [A] | A | PRSV-CP-AusHawSync |
| 211 | A | A | C | T | G | A | ConsensusForAmericaSync |
| 211 | A | A | C | T | [A] | A | PRSV-CP-AmericaSync |
| 211 | A | A | C | T | G | A | PRSV-CP-AsiaSync |
| 211 | A | A | [T] | T | G | A | ConsensusForAsiaSync |
| 211 | A | A | C | T | G | A | PRSV-CP-UniversalSync |

Decoration 'Decoration #1': Box residues that differ from PRSV-CP-UniversalSync.

FIGURE 19 (Con't)

FIGURE 20

FIGURE 20 (Con't)

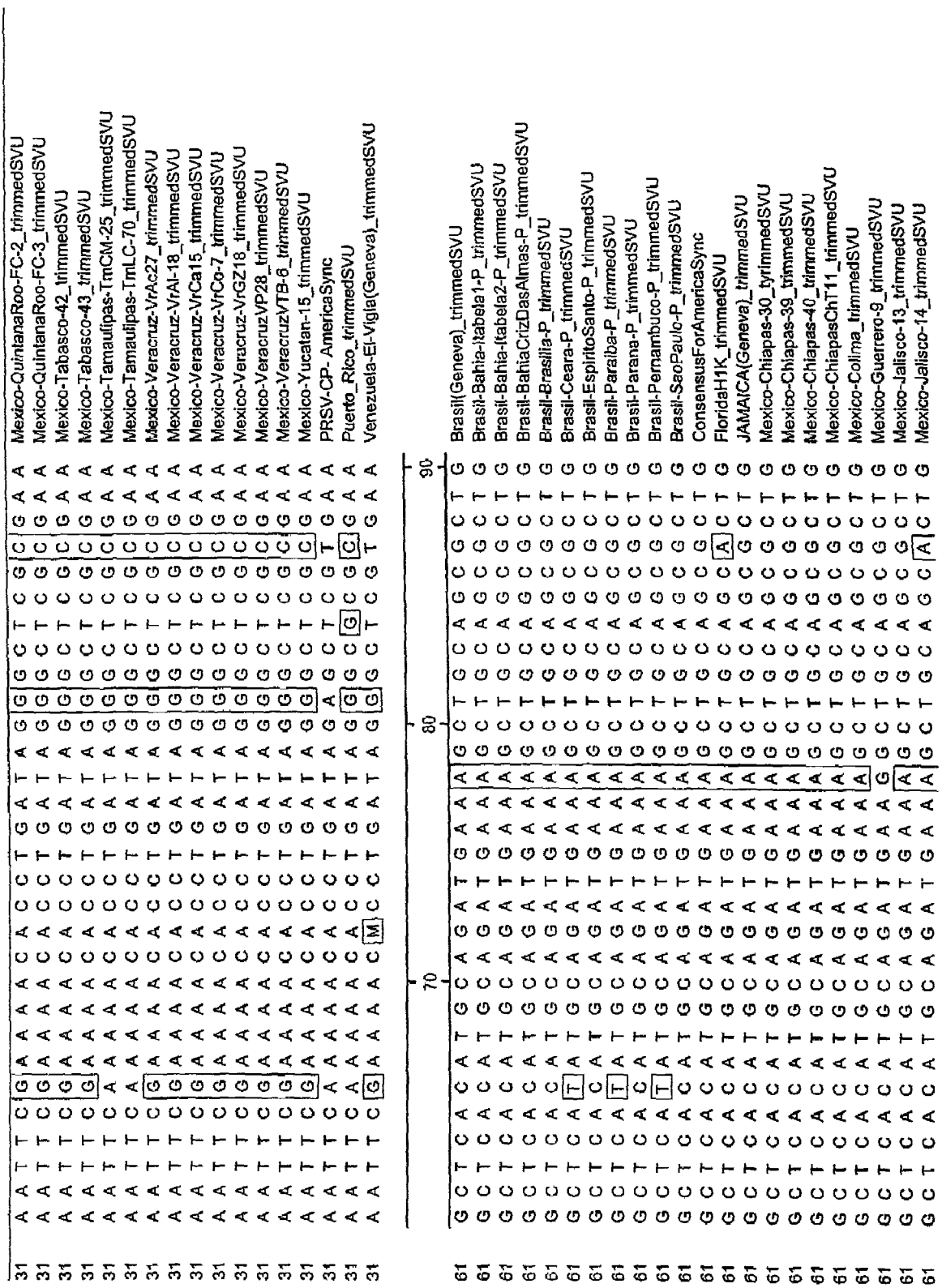
FIGURE 20 (Con't)

FIGURE 20 (Con't)

FIGURE 20 (Con't)

FIGURE 20 (Con't)

FIGURE 20 (Con't)

FIGURE 20 (Con't)

FIGURE 20 (Con't)

FIGURE 20(Con't)

FIGURE 21

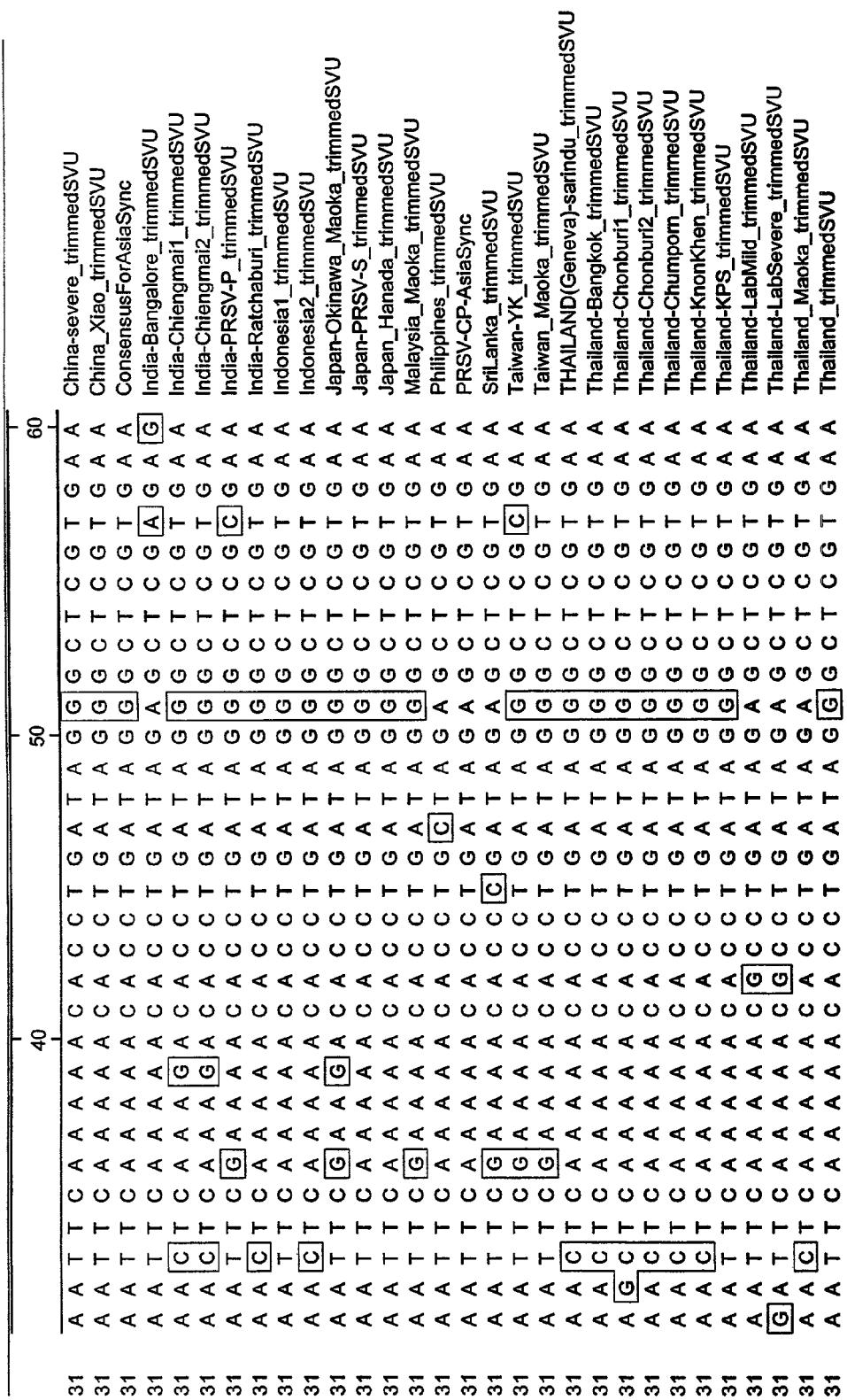
FIGURE 21 (Con't)

FIGURE 21 (Con't)

FIGURE 21 (Con't)

FIGURE 21 (Con't)

FIGURE 21 (Con't)

FIGURE 21 (Con't)

| Pos | | | | | Strain |
|---|---|---|---|---|---|
| 211 | A | A | T | G | A | China-severe_trimmedSVU |
| 211 | A | A | C | A | A | China_Xiao_trimmedSVU |
| 211 | A | A | T | G | A | ConsensusForAsiaSync |
| 211 | A | A | T | G | A | India-Bangalore_trimmedSVU |
| 211 | A | A | T | G | A | India-Chiengmai1_trimmedSVU |
| 211 | A | A | T | G | A | India-Chiengmai2_trimmedSVU |
| 211 | A | A | C | G | A | India-PRSV-P_trimmedSVU |
| 211 | A | A | T | G | A | India-Ratchaburi_trimmedSVU |
| 211 | A | A | T | G | A | Indonesia1_trimmedSVU |
| 211 | A | A | T | G | A | Indonesia2_trimmedSVU |
| 211 | A | A | T | G | A | Japan-Okinawa_Maoka_trimmedSVU |
| 211 | A | A | T | G | A | Japan-PRSV-S_trimmedSVU |
| 211 | A | A | T | G | A | Japan_Hanada_trimmedSVU |
| 211 | A | A | T | G | A | Malaysia_Maoka_trimmedSVU |
| 211 | A | A | C | G | A | Philippines_trimmedSVU |
| 211 | A | A | C | G | A | PRSV-CP-AsiaSync |
| 211 | A | A | C | A | A | SriLanka_trimmedSVU |
| 211 | A | A | T | G | A | Taiwan-YK_trimmedSVU |
| 211 | A | A | T | G | A | Taiwan_Maoka_trimmedSVU |
| 211 | A | A | T | G | A | THAILAND(Geneva)-sarindu_trimmedSVU |
| 211 | A | A | T | G | A | Thailand-Bangkok_trimmedSVU |
| 211 | A | A | T | G | A | Thailand-Chonburi1_trimmedSVU |
| 211 | A | A | T | G | A | Thailand-Chonburi2_trimmedSVU |
| 211 | A | A | T | G | A | Thailand-Chumporn_trimmedSVU |
| 211 | A | A | T | G | A | Thailand-KnonKhen_trimmedSVU |
| 211 | A | A | T | G | A | Thailand-KPS_trimmedSVU |
| 211 | A | A | T | G | A | Thailand-LabMild_trimmedSVU |
| 211 | A | A | T | G | A | Thailand-LabSevere_trimmedSVU |
| 211 | A | A | T | G | A | Thailand_Maoka_trimmedSVU |
| 211 | A | A | T | G | A | Thailand_trimmedSVU |

Decoration 'Decoration #1': Box residues that differ from PRSV-CP-AsiaSync.

FIGURE 21 (Con't)

FIGURE 22

FIGURE 22 (Con't)

| | | | | | | | | | | | | | | | | | |
|---|---|---|---|---|---|---|---|---|---|---|---|---|---|---|---|---|---|
|181|A|G|A|A|C|A|T|G|C|C|T|C|T|C|T|G|T|A|T|G|C|Australia-Bridgeman_Downs_trimmedSVU|
|181|A|G|A|G|A|C|A|T|G|C|C|T|C|T|C|T|G|T|A|T|G|C|Australia-Bundaberg_trimmedSVU|
|181|A|G|A|G|A|C|A|T|T|G|C|C|T|C|T|C|T|G|T|A|T|G|C|Australia-PRSV-P_trimmedSVU|
|181|A|G|A|G|A|C|A|T|T|G|C|C|T|C|T|C|T|G|T|A|T|G|C|Australia-Wellington_Point_trimmedSVU|
|181|A|G|A|G|A|C|A|T|T|G|C|C|T|C|T|C|T|G|T|A|T|G|C|Hawaii_trimmedSVU|
|181|A|G|A|G|A|C|A|T|T|G|C|C|T|C|T|C|T|G|G|C|A|T|G|C|Hawaii-KEAAUGeneva_trimmedSVU|
|181|A|G|A|G|A|C|A|T|T|G|C|C|T|C|T|C|T|G|T|A|T|G|C|Hawaii-OAHUGeneva_trimmedSVU|
|181|A|G|A|G|A|C|A|T|T|G|C|C|T|C|T|C|T|G|T|A|T|G|C|PRSV-CP-AusHawSync|
|181|A|G|A|G|A|C|A|T|T|G|C|C|T|C|T|C|T|G|T|A|T|G|C|ConsensusForSyncAusHaw|

| | | | | | |
|---|---|---|---|---|---|
|211|A|A|C|T|G|A|Australia-Bridgeman_Downs_trimmedSVU|
|211|A|A|C|T|G|A|Australia-Bundaberg_trimmedSVU|
|211|A|A|C|T|G|A|Australia-PRSV-P_trimmedSVU|
|211|A|A|C|T|G|A|Australia-Wellington_Point_trimmedSVU|
|211|A|A|C|T|A|A|Hawaii_trimmedSVU|
|211|A|A|C|T|A|A|Hawaii-KEAAUGeneva_trimmedSVU|
|211|A|A|C|T|A|A|Hawaii-OAHUGeneva_trimmedSVU|
|211|A|A|C|T|G|A|PRSV-CP-AusHawSync|
|211|A|A|C|T|A|A|ConsensusForSyncAusHaw|

Decoration 'Decoration #1': Box residues that differ from PRSV-CP-AusHawSync.

FIGURE 22 (Con't)

```
                              SEQUENCE LISTING

<160> NUMBER OF SEQ ID NOS: 235

<210> SEQ ID NO 1
<211> LENGTH: 216
<212> TYPE: DNA
<213> ORGANISM: Tomato Spotted Wilt Virus CP

<400> SEQUENCE: 1
gcaaagtctg tgaggcttgc cataatgctg ggaggtagct tacctcttat tgcttcagtt    60
gatagctttg agatgatcag tgttgtcttg gctatatatc aggatgcaaa atacaaggat   120
ctcgggatcg acccaaagaa gtatgacacc agggaagcct taggaaaagt ttgcactgtg   180
ctgaaaagaa aagcatttga aatgaatgaa gatcag                              216

<210> SEQ ID NO 2
<211> LENGTH: 216
<212> TYPE: DNA
<213> ORGANISM: Groundnut Ringspot Virus CP

<400> SEQUENCE: 2
gcaaaatctg tgagacttgc cataatgctt ggaggtagta tccctctcat tgcttctgtt    60
gacagtctcg aaatgatcag tgttgttctt gccatatatc aagatagtca agtacaggag   120
ttagggattg aaccaactaa gtacaacact aaggaagctc tggggaaggt ttgcactgtg   180
ctgaaaagca aaggatttac aatggatgat gcacaa                              216

<210> SEQ ID NO 3
<211> LENGTH: 199
<212> TYPE: DNA
<213> ORGANISM: Tomato Chlorotic Spot Virus CP

<400> SEQUENCE: 3
gcaaagtctg taaggcttgc cataatgcta ggaggtagta tccctctgat tgcttctgtg    60
gacagctttg aaatgatcag catcatcctt gccatatacc aagatgctaa atataaagat   120
```

```
cttggaattg aaccttcgaa gtataacact aaagaagctt taggaaaagt ctgcactgtg    180
ctgaaaagca aaggattta                                                 199

<210> SEQ ID NO 4
<211> LENGTH: 216
<212> TYPE: DNA
<213> ORGANISM: Artificial Sequence
<220> FEATURE:
<223> OTHER INFORMATION: Description of Artificial Sequence:  Synthetic
      Rec2 CP

<400> SEQUENCE: 4
gcaaaatctg tgagacttgc cataatgctg ggaggtagta tccctcttat tgcttctgtt    60
gacagctttg aaatgatcag tgttgtcctt gctatatatc aagatgcaaa atacaaggat   120
ctcgggattg aaccaacgaa gtataacact aaggaagcct taggaaaagt ttgcactgtg   180
ctgaaaagca aggatttac aatggatgaa gatcag                              216

<210> SEQ ID NO 5
<211> LENGTH: 203
<212> TYPE: DNA
<213> ORGANISM: Artificial Sequence
<220> FEATURE:
<223> OTHER INFORMATION: Description of Artificial Sequence:  Sync-Con

<400> SEQUENCE: 5
gctagatatg ctttcgactt ctatgaggtg aattcgaaaa cacctgatag ggctcgtgaa    60
gctcatatgc agatgaaggc tgcagcgctg cgcaacacta atcgcagaat gtttggaatg   120
gacggcagtg ttagtaacaa ggaagaaaac acggagagac acacagtgga agatgtcaat   180
agagacatgc actctctcct ggg                                            203

<210> SEQ ID NO 6
<211> LENGTH: 203
<212> TYPE: DNA
<213> ORGANISM: TH PRSV-CP Conserved Region

<400> SEQUENCE: 6
gctagatatg ctttcgactt ctatgaggtg aactcaaaaa cacctgatag ggctcgtgaa    60
gctcatatgc agatgaaggc tgcagcgctg cgcaacactg atcgcagaat gtttggaatg   120
gacggcagtg tcagtaacaa ggaagaaaac acggagagac acacagtgga agatgtcaac   180
agagacatgc actctctcct agg                                            203

<210> SEQ ID NO 7
<211> LENGTH: 203
<212> TYPE: DNA
<213> ORGANISM: KE PRSV-CP Conserved Region

<400> SEQUENCE: 7
gctagatatg ctttcgactt ctatgaggtg aattcgaaaa cacctgatag ggctcgcgaa    60
gcccacatgc agatgaaggc tgcagcgctg cgaaacacta gtcgcagaat gtttggtatg   120
gacggcagtg ttagtaacaa ggaagaaaac acggagagac acacagtgga agatgtcaat   180
agagacatgc actctctcct ggg                                            203

<210> SEQ ID NO 8
<211> LENGTH: 203
<212> TYPE: DNA
<213> ORGANISM: YK PRSV-CP Conserved Region
```

```
<400> SEQUENCE: 8
gctagatatg ctttcgattt ctatgaggtg aattcgaaaa cacctgatag ggctcgtgaa      60
gctcatatgc agatgaaggc tgcagcgcta cgcaatacta atcgcaaaat gtttggaatg     120
gacggcagtg tcagtaacaa ggaagaaaac acggagagac acacagtgga agatgtcaac     180
agagacatgc actctctcct ggg                                             203

<210> SEQ ID NO 9
<211> LENGTH: 209
<212> TYPE: DNA
<213> ORGANISM: Artificial Sequence
<220> FEATURE:
<223> OTHER INFORMATION: Description of Artificial Sequence:  Synthetic
      Sequence for TH-KE-YK PRSV-CP Variable Region

<400> SEQUENCE: 9
tgctggtctg aatgagaagc tcaaagagaa agaaaaacag aaagaaaaag aaaaagataa      60
acaaaaagat aaagaaaatg atgaagctag tgacggaaat gatgtgtcaa ctagcacaaa     120
aactggagag agagatagag atgtcaatgc tggaactagt ggaactttca ctgttccgag     180
gataaaatca tttactgata agttgattt                                       209

<210> SEQ ID NO 10
<211> LENGTH: 206
<212> TYPE: DNA
<213> ORGANISM: TH PRSV-CP Variable Region

<400> SEQUENCE: 10
tgctggtctt aatgagaagt tcaaagataa agaaaaacag aaagaagaaa aagataaaca      60 aaaggtaaa gaaaataatg aagctagtga cggaaatgat gtgtcaacta gcacaaaaac     120
tggagagaga gatagagatg tcaatgccgg aactagtggt actttcactg ttccgagaat     180
aaaattattt accgacaaga tgattt                                          206

<210> SEQ ID NO 11
<211> LENGTH: 209
<212> TYPE: DNA
<213> ORGANISM: KE PRSV-CP Variable Region

<400> SEQUENCE: 11
tgctggtttg aatgaaaaac tcaaagagaa agaaaaacag aaagaaaaag aaaagaaaa       60 acaaaaagaa aaggaaaag acgatgctag tgacgaaaat gatgtgtcaa ctagcacaaa     120
aactggagag agagatagag atgtcaatgt tgggaccagt ggaactttcg ctgttccgag     180
aattaaatca tttactgata agttgattc                                       209

<210> SEQ ID NO 12
<211> LENGTH: 209
<212> TYPE: DNA
<213> ORGANISM: YK PRSV-CP Variable Region

<400> SEQUENCE: 12
taccggtctg aatgagaagc tcaaagaaaa agaaaagcag aaagaaaaag aaaaagataa      60
acaacaagat aaagacaatg atggagctag tgacggaaac gatgtgtcaa ctagcacaaa     120
aactggagag agagataggg atgtcaatgc cggaactagt ggaaccttca ctgttccgag     180
gataaagtca tttactgata agatgatct                                       209

<210> SEQ ID NO 13
```

<211> LENGTH: 202
<212> TYPE: DNA
<213> ORGANISM: Bean PotyV-CP

<400> SEQUENCE: 13

```
atgtcaattg taatgaatgg cttcatggta tggtgtattg acaatggcac ttcaccggat    60
gtgaatggca catgggtgat gatggatgga gacgagcaag ttgagtaccc actcaaacca   120
atggttgaaa atgcaaagcc aacactccgt caaatcatgc accatttctc agatgcagct   180
gaggcataca ttgagatgag aa                                            202
```

<210> SEQ ID NO 14
<211> LENGTH: 202
<212> TYPE: DNA
<213> ORGANISM: Maize PotyV-CP

<400> SEQUENCE: 14

```
atgacggttg tcatgagtgg attaatggtt tggtgcattg agaatggttg ctcaccaaac    60
atcaatggag tctggacaat gatggatgga gacgaacaga gaacatttcc tttaaaacag   120
gttattggaa atgcatctcc aactttcaga caaattatgc atcattttag tgatgcagct   180
gaagcataca ttgagtatag aa                                            202
```

<210> SEQ ID NO 15
<211> LENGTH: 202
<212> TYPE: DNA
<213> ORGANISM: Peanut Mottle PotyV-CP

<400> SEQUENCE: 15

```
atgagtgttc tcatgaatgg gctgatggtt tggtgcattg agaatggcac ctcaccaaat    60
atcaacggaa attggaccat gatggacggg cacgagcaaa atgagtatcc attaaagcct   120
gtcattgaaa acgccaagcc aacatttcgt cagataatgc accatttttc agacgcggct   180
gaggcgtaca ttgagatgag aa                                            202
```

<210> SEQ ID NO 16
<211> LENGTH: 202
<212> TYPE: DNA
<213> ORGANISM: Peanut Stripe PotyV-CP

<400> SEQUENCE: 16

```
atgtcaattg tgatgaacgg ctttatggtg tggtgtattg acaatggcac ttcaccggat    60
gtaaatggaa catgggtgat gatggacgga gacgagcaag tggaatatcc tctcaaacca   120
atggttgaga atgcaaaacc tacacttcgt caaatcatgc accatttctc agatgcagct   180
gaagcataca ttgagatgag aa                                            202
```

<210> SEQ ID NO 17
<211> LENGTH: 202
<212> TYPE: DNA
<213> ORGANISM: Pepper PotyV-CP

<400> SEQUENCE: 17

```
atgggtacag tgatgaatgg cttaatggtt tggtgcattg aaaatggcac gtccccaaac    60
attagtggaa catggaccat gatggatgga gacgaacaag tggaattccc attaaagccc   120
gtgatagaga atgccaagcc gacttttcgg caataatgg cgcacttttc tgatgtggct   180
gaggcatata tagaaatgcg ca                                            202
```

```
<210> SEQ ID NO 18
<211> LENGTH: 202
<212> TYPE: DNA
<213> ORGANISM: PotatoY PotyV-CP

<400> SEQUENCE: 18
atgccaactg tgatgaatgg gcttatggtt tggtgcattg aaaatggaac ctcgccaaat     60
gtcaacggag tttgggttat gatggatggg aatgaacaag ttgagtaccc gttgaaacca    120
atcgttgaga atgcaaaacc aacccttagg caaatcatgg cacatttctc agatgttgca    180
gaagcgtata tagaaatgcg ca                                              202

<210> SEQ ID NO 19
<211> LENGTH: 202
<212> TYPE: DNA
<213> ORGANISM: Soybean PotyV-CP

<400> SEQUENCE: 19
atgggtgtgg ttatgaatgg cttcatggta tggtgcattg acaatggtac atctccagat     60
gctaatggcg tgtgggtgat gatggatgga gaggaacaga ttgaatatcc gctgaaaccc    120
attgtcgaaa atgcaaaacc aactttgaga caaatcatgc accatttctc agatgcagca    180
gaagcttaca ttgagatgag aa                                              202

<210> SEQ ID NO 20
<211> LENGTH: 202
<212> TYPE: DNA
<213> ORGANISM: Sugarcane PotyV-CP

<400> SEQUENCE: 20
atgacagttg tcatgagtgg tctcatggta tggtgcatcg aaaatggttg ctcaccaaac     60
ataaacggaa attggacgat gatggacgga gacgaacaaa gggttttttcc attaaagcca    120 gtcattgaga acgcatctcc aacttttccga cagataatgc atcattttag tgatgcagct    180
gaagcgtata tagagtaccg aa                                              202

<210> SEQ ID NO 21
<211> LENGTH: 202
<212> TYPE: DNA
<213> ORGANISM: Zucchini PotyV-CP

<400> SEQUENCE: 21
atgggagttg taatgaatgg tttcatggtt tggtgcattg aaaatggcac ttcgcctgat     60
atcaatggag tgtggttcat gatggatgga gatgagcagg tcgagtatcc tttgaaacca    120
atagtcgaaa atgcaaagcc aacgctgcga caaataatgc atcacttctc agatgcagcg    180
gaggcataca tagaaatgag aa                                              202

<210> SEQ ID NO 22
<211> LENGTH: 202
<212> TYPE: DNA
<213> ORGANISM: Artificial Sequence
<220> FEATURE:
<223> OTHER INFORMATION: Description of Artificial Sequence:  Block 1
      Consensus PotyV-CP

<400> SEQUENCE: 22
atggcagttg tgatgaatgg cttcatggtt tggtgcattg aaaatggcac ctcaccaaat     60
atcaatggaa tttgggtgat gatggatgga gacgaacaag ttgagtatcc attaaaacca    120
atggttgaaa atgcaaagcc aacttttcga caaatcatgc accatttctc agatgcagct    180
```

```
gaagcataca ttgagatgag aa                                            202
```

<210> SEQ ID NO 23
<211> LENGTH: 202
<212> TYPE: DNA
<213> ORGANISM: Artificial Sequence
<220> FEATURE:
<223> OTHER INFORMATION: Description of Artificial Sequence:  Block 1
      Synthetic Poty-CP

<400> SEQUENCE: 23

```
atgggagttg tgatgaatgg cctcatggtt tggtgcattg aaaatggaac ctcaccaaac    60
atcaatggag tatgggctat gatggatggg gacgaacaag ttgagtttcc attaaagcca   120
gtgattgaga atgcaaagcc aactttcga caaatcatgc atcattttc agatgcagca    180 gaagcttaca tagagtagag ca                                           202
```

<210> SEQ ID NO 24
<211> LENGTH: 207
<212> TYPE: DNA
<213> ORGANISM: Artificial Sequence
<220> FEATURE:
<223> OTHER INFORMATION: Description of Artificial Sequence:
      Lycopersicon Consensus Sequence

<400> SEQUENCE: 24

```
caaggagtga aggtatcagc tccaggaaat agtcccaaca cagatggaat tcatgtaaaa    60
tcatcatcag gagttagtat tatgaactca catattggta ctggagatga ttgtatctct   120
attggccctg gaaattcgaa cttatggatt gaaggcattg cttgtggccc tggccatgga   180
ataagcattg gaagcttagg ctggaaa                                       207
```

<210> SEQ ID NO 25
<211> LENGTH: 207
<212> TYPE: DNA
<213> ORGANISM: Lycopersicon

<400> SEQUENCE: 25

```
caaggactga aggtatcagc tccaggagat agtcccaaca cagatggaat tcatgtaaaa    60
ttatcatcag gagttagtat tatgaaatca caaattggta ctggagacga ttgtatatcc   120
attggccctg gaaattctaa cttatggatt gaaggcattg cttgtggccc tggccatgga   180
ataagcattg gaagcttagg ctggaaa                                       207
```

<210> SEQ ID NO 26
<211> LENGTH: 207
<212> TYPE: DNA
<213> ORGANISM: Lycopersicon

<400> SEQUENCE: 26

```
caaggagtaa aggtatccgc tccaggaaat agtcccaaca cagatggaat tcatgtaaaa    60
tcatcatctg gagttagtat tatgaaatca caaattggta ctggagatga ttgtatctct   120
attggccctg gaacttcaaa cttatggatt gaaggcattg cttgtggccc tggccatgga   180
ataagcattg gaagcttagg ctggaaa                                       207
```

<210> SEQ ID NO 27
<211> LENGTH: 207
<212> TYPE: DNA
<213> ORGANISM: Lycopersicon

```
<400> SEQUENCE: 27
caaggagtaa aggtatcagc tccaggaaat agtcccaaca cagatggaat tcatgtaaaa      60
ttatcatctg gagttagcat tataaactca catattggta ctggagacga ttgcatctct     120
attggccctg gaacttcaaa cttatggatt gaaggcattg cttgtggccc tggccatgga     180
ataagcattg gaagcttagg ctggaaa                                         207

<210> SEQ ID NO 28
<211> LENGTH: 207
<212> TYPE: DNA
<213> ORGANISM: Lycopersicon

<400> SEQUENCE: 28
caaggagtga aggtgttatc tccaggaaat agccctaata ctgatggaat tcatgtacaa      60
tcatcctcag gagttagtat tatgaactcg aatattggta ctggagatga ttgtatatct     120
attggccctg gaaactcgaa tttatggatt gaaggcattg cttgtggccc aggccatgga     180
attagcattg gaagcttagg ttgggaa                                         207

<210> SEQ ID NO 29
<211> LENGTH: 207
<212> TYPE: DNA
<213> ORGANISM: Lycopersicon

<400> SEQUENCE: 29
caaggagtga aggtgttagc cccaggaaat agcccgaata ctgatggaat tcatgtacaa      60
tcatcttcag gagttagtat taggaactcg aatattggta ctggagatga ttgtatctct     120
attggccctg gaaactcgaa cttatggatt gaaggcattg cttgtggccc tggccatgga     180
attagcattg gaagcttagg ttgggaa                                         207

<210> SEQ ID NO 30
<211> LENGTH: 207
<212> TYPE: DNA
<213> ORGANISM: Artificial Sequence
<220> FEATURE:
<223> OTHER INFORMATION: Description of Artificial Sequence:
      Lycopersicon Synthetic Sequence

<400> SEQUENCE: 30
caaggagtga aggtgtcagc tccaggaaat agccccaata ctgatggaat tcatgtacaa      60
tcatcatctg gagttagtat tatgaaatca aatattggta ctggagacga ttgtatatct     120
attggccctg gaacttcgaa cttatggatt gaaggcattg cttgtggccc tggccatgga     180
ataagcattg gaagcttagg ctgggaa                                         207

<210> SEQ ID NO 31
<211> LENGTH: 134
<212> TYPE: DNA
<213> ORGANISM: Petunia CHS

<400> SEQUENCE: 31
aagctacttg ggcttcgtcc atcggtcaag aggctcatga tgtaccaaca ggggttgcttt     60 gctggaggca cggttcttcg gttagccaag gacttggctg aaaacaacaa gggcgctcga    120
gtccttgttg tttg                                                       134

<210> SEQ ID NO 32
<211> LENGTH: 134
<212> TYPE: DNA
```

```
<213> ORGANISM: Petunia CHSB

<400> SEQUENCE: 32
aagctccttg gcctaagccc atcagttcaa cgtctaatga tgtaccaaca aggttgtttt    60
gctggtggca caatgcttag attggcaaag gacttagctg agaataacaa aggagctagg   120
gtacttgtcg tgtg                                                     134

<210> SEQ ID NO 33
<211> LENGTH: 134
<212> TYPE: DNA
<213> ORGANISM: Petunia CHSD

<400> SEQUENCE: 33
aagcttcttg gacttggttc atcagttaag cgattcatga tgaaccaact aggttgtttt    60
gctggtggca cagttcttcg tttggcgaag gacttggctg agaacaacaa gggcgctcgt   120
gtccttgttg tttg                                                     134

<210> SEQ ID NO 34
<211> LENGTH: 134
<212> TYPE: DNA
<213> ORGANISM: Petunia CHSF

<400> SEQUENCE: 34
aagcttcttg gacttagccc atcagtcaag agactcatga tgtaccaact aggttgctat    60
ggtggtggca ccgttctccg attggcaaaa gacctagcag agaataacaa gggcgctcga   120
gcccttgtcg tttg                                                     134

<210> SEQ ID NO 35
<211> LENGTH: 134
<212> TYPE: DNA
<213> ORGANISM: Petunia CHSG

<400> SEQUENCE: 35
aagcttcttg gactttctcc atcagttaaa cgatcaatga tgtaccaaca aggtgctat     60 ggtggtggca ctgctctccg attggccaag gacttggctg agaataacaa gggggctcgg   120
gtccttgttg tttg                                                     134

<210> SEQ ID NO 36
<211> LENGTH: 134
<212> TYPE: DNA
<213> ORGANISM: Petunia CHSJ

<400> SEQUENCE: 36
aagcttcttg ggcttcggtc atcagtcaag cgactcatga tgtaccaaca aggttgtttt    60
gctggtggca ctgtactccg attggctaag gacttagccg aaaacaacaa gggtgcacga   120
gtccttgttg tttg                                                     134

<210> SEQ ID NO 37
<211> LENGTH: 134
<212> TYPE: DNA
<213> ORGANISM: Artificial Sequence
<220> FEATURE:
<223> OTHER INFORMATION: Description of Artificial Sequence: Petunia
      CHS Consensus Sequence

<400> SEQUENCE: 37
aagcttcttg gacttagtcc atcagttaag cgactcatga tgtaccaaca aggttgtttt    60
```

```
gctggtggca cagttcttcg attggcaaag gacttggctg agaataacaa gggcgctcga      120
gtccttgttg tttg                                                       134
```

<210> SEQ ID NO 38
<211> LENGTH: 134
<212> TYPE: DNA
<213> ORGANISM: Artificial Sequence
<220> FEATURE:
<223> OTHER INFORMATION: Description of Artificial Sequence:  Petunia
      CHS Synthetic Sequence

<400> SEQUENCE: 38

```
aagctccttg gacttagtcc atcagtcaag cgactaatga tgtaccaaca aggttgcttt       60
gctggtggca ctgtgcttcg attggcaaag gacttggctg agaataacaa aggcgctcga      120
gtccttgttg tgtg                                                       134
```

<210> SEQ ID NO 39
<211> LENGTH: 291
<212> TYPE: DNA
<213> ORGANISM: Sorghum

<400> SEQUENCE: 39

```
actcaaggag aagttcaaga ggatgtgtga caagtcgcag atccggaagc ggtacatgca       60
cctgacggag gagtacctgg cggagaaccc caacatgtgt gcgtacatgg cgccgtcgct      120
ggacgcccgc caggacatcg tggtggttga ggtccccaag ctaggcaagg ctgcggcgca      180
gaaggcgatc aaggagtggg ggcagccgaa atccaagatc acccacctcg tcttctgcac      240
cacctccggc gtcgacatgc cgggcgcgga ctaccagctc accaagatgc t              291
```

<210> SEQ ID NO 40
<211> LENGTH: 291
<212> TYPE: DNA
<213> ORGANISM: Sorghum

<400> SEQUENCE: 40

```
actcaaggag aagttcaaga ggatgtgcga caagtcgcag atccggaagc ggtacatgca       60
cctgacggag gagtacctag cggagaaccc caacatgtgc gcgtacatgg cgccgtcgct      120
ggacgcccgc caggacatcg tggtggtgga ggtccccaag ctgggcaagg ccgcagcgca      180
gaaggcgatc aaggagtggg ggcagccgaa atccaagatc acccacctcg tcttctgcac      240
cacctccggc gtcgacatgc cgggcgccga ctaccagctc accaagatgc t              291
```

<210> SEQ ID NO 41
<211> LENGTH: 291
<212> TYPE: DNA
<213> ORGANISM: Sorghum

<400> SEQUENCE: 41

```
cctcaaggag aagttcaaga ggatgtgcga caagtcgcag atccgaaagc ggtacatgca       60
cctgacggag gagtacctgg cggagaaccc taacatgtgt gcgtacatgg cgccgtcgct      120
ggacgcccgc caggacatcg tggtggtgga ggtccccaag ctgggcaagg ccgcggcgca      180
gaaggcgatc aaggagtggg ggcagccgaa atccaagatc acccatctcg tcttctgcac      240
cacctccggc gtcgacatgc ccggcgccga ctaccagctc accaagatgc t              291
```

<210> SEQ ID NO 42
<211> LENGTH: 291
<212> TYPE: DNA

<210> SEQ ID NO 42
<211> LENGTH: 291
<212> TYPE: DNA
<213> ORGANISM: Sorghum

<400> SEQUENCE: 42

```
actcaaggag aagttcaaga ggatgtgcga caagtcgcag atccggaagc ggtacatgca    60
cctgacggag gagtatctgg cggagaaccc caacatgtgc gcgtacatgg cgccgtcgct   120
ggacgcccgc caggacatcg tggtggtgga ggtgcccaag ctaggcaagg ccgcggcgca   180
gaaggcaatc aaggagtggg ggcagccgaa atccaagatc acccacctcg tcttctgcac   240
cacctccggc gtcgacatgc cgggcgctga ctaccagctc accaagatgc t            291
```

<210> SEQ ID NO 43
<211> LENGTH: 291
<212> TYPE: DNA
<213> ORGANISM: Sorghum

<400> SEQUENCE: 43

```
actcaaggag aagttcaaga ggatgtgcga caagtcgcag atccggaagc ggtacatgca    60
cctgacggag gagtacctgg cggagaaccc caacatgtgc gcgtacatgg cgccgtcgct   120
ggacgcccgc caggacatcg tggtggtgga ggtgcccaag ctaggcaagg ccgcggcgca   180
taaggcgatc aaggagtggg ggcagccgaa atccaagatc actcacctcg tcttctgcac   240
cacctccggc gtcgacatgc cgggcgccga ctaccagctc accaagatgc t            291
```

<210> SEQ ID NO 44
<211> LENGTH: 291
<212> TYPE: DNA
<213> ORGANISM: Sorghum

<400> SEQUENCE: 44

```
actcaaggag aagttcaaga ggatgtgcga caagtcgcag atccggaagc ggtacatgca    60
cttgaccgag gagtacctgg cggagaaccc taacatgtgc gcgtacatgg cgccttcgct   120
ggacgcccgc caggacatcg tggtggtgga ggtccccaag ctaggcaagg ccgcggcgca   180
gaaggcgatc aaggaatggg ggcagccgaa atccaagatc acccacctcg tcttctgcac   240
cacctccggc gtcgacatgc cgggcgccga ctaccagctc accaagatgc t            291
```

<210> SEQ ID NO 45
<211> LENGTH: 291
<212> TYPE: DNA
<213> ORGANISM: Sorghum

<400> SEQUENCE: 45

```
cctcaaggag aagttcaaga gaatgtgcga caagtcgcag atccggaagc ggtacatgca    60
cctgacggag gagtatctgg cggagaaccc caacatgtgc gcgtacatgg cgccgtcgct   120
ggacgcccgc caggacatcg tggtggtgga ggtccccaag ctaggcaagg ccgcggcaca   180
gaaggcaatc aaggagtggg ggcagcccaa atccaagatc acccacctcg tcttctgcac   240
cacctccggt gtcgacatgc cgggcgccga ctaccagctc accaagatgc t            291
```

<210> SEQ ID NO 46
<211> LENGTH: 291
<212> TYPE: DNA
<213> ORGANISM: Artificial Sequence
<220> FEATURE:
<223> OTHER INFORMATION: Description of Artificial Sequence: Sorghum CHS Consensus Sequence

<400> SEQUENCE: 46

```
actcaaggag aagttcaaga ggatgtgcga caagtcgcag atccggaagc ggtacatgca      60
cctgacggag gagtacctgg cggagaaccc caacatgtgc gcgtacatgg cgccgtcgct     120
ggacgcccgc caggacatcg tggtggtgga ggtccccaag ctaggcaagg ccgcggcgca     180
gaaggcgatc aaggagtggg ggcagccgaa atccaagatc acccacctcg tcttctgcac     240
cacctccggc gtcgacatgc cgggcgccga ctaccagctc accaagatgc t              291
```

<210> SEQ ID NO 47
<211> LENGTH: 291
<212> TYPE: DNA
<213> ORGANISM: Artificial Sequence
<220> FEATURE:
<223> OTHER INFORMATION: Description of Artificial Sequence: Sorghum
      Synthetic CHS Sequence

<400> SEQUENCE: 47

```
cctcaaggag aagttcaaga ggatatgcga caagtcgaag atcaggaagc gttacatgca      60
cttgacggag gagaacctag cggagaaccc caacatatgc gcgtacaggg cgccgtcgct     120
ggacgcccgc caggacatcg tggtggtgga gataccccaag ctaggcgagg ccgcggcgca    180
gaaggcgatc aaagagtggg ggcagccgaa ttccaagatc acgcacctcg tcttctgcac     240
cacctccggc gtcgacatgc ctggcgccga ctaccagctc atcaagatgc t              291
```

<210> SEQ ID NO 48
<211> LENGTH: 260
<212> TYPE: DNA
<213> ORGANISM: Actinidia Deliciosa ACC

<400> SEQUENCE: 48

```
ccagagctga tcaagggtct ccgagcccac accgacgccg gtggcatcat cctcctcttc      60
caagacaaca aggtcagcgg actccaactg ctcaaagatg gcgaatggat cgatgtccca     120
ccaatgaaac actccattgt gatcaacata ggtgaccagc ttgaggtaat cacaaatggc     180
aagtacaaga gcgtgatgca ccgtgtgatt gctcagccgg atggcaacag aatgtcaata     240
gcttcattct acaatccagg                                                 260
```

<210> SEQ ID NO 49
<211> LENGTH: 260
<212> TYPE: DNA
<213> ORGANISM: Arabidopsis Thaliana2 ACC

<400> SEQUENCE: 49

```
ccagagatga tcaaagggct tagggctcac acagatgcag gaggcctcat tttgctgttt      60
caagatgata aggtcagtgg tctccagctt cttaaagatg gtgattgggt tgatgttcct     120
cctctcaagc attccattgt catcaacctt ggtgaccaac ttgaggtgat aacaaacggg     180
aagtacaaga gtgtaatgca ccgtgtgatg acccagaaag aaggaaacag gatgtctatc     240
gcgtcgtttt acaaccccgg                                                 260
```

<210> SEQ ID NO 50
<211> LENGTH: 200
<212> TYPE: DNA
<213> ORGANISM: Arabidopsis Thaliana2 ACC

<400> SEQUENCE: 50

```
ccagagatga tcaaaggtct tagggcccac actgatgcag gaggcatcat cttgttgttt      60
caagacgaca aggtcagtgg tctccagctt cttaaagatg gtgactggat tgatgttcct     120
```

```
cctctcaacc actctattgt catcaatctt ggtgaccaac ttgaggtgat aaccaacggg      180
gcatcgtttt acaacccggg                                                  200

<210> SEQ ID NO 51
<211> LENGTH: 260
<212> TYPE: DNA
<213> ORGANISM: Artificial Sequence
<220> FEATURE:
<223> OTHER INFORMATION: Description of Artificial Sequence:  Block 1
      ACC-Oxidase Consensus

<400> SEQUENCE: 51
ccagagctga tcaaaggtct tagggctcac acagatgcag gtggcatcat cctgctgttc       60
caagatgaca aggtcagtgg tctccagctt ctcaaagatg gtgaatggat tgatgttcct      120
ccaatgaacc actccattgt catcaaccct ggtgaccaac ttgaggtgat aaccaatggg      180
aagtacaaga gtgtgatgca ccgtgtgatg gctcagacag atggaaacag aatgtctata      240
gcatcgttct acaacccggg                                                  260

<210> SEQ ID NO 52
<211> LENGTH: 260
<212> TYPE: DNA
<213> ORGANISM: Brassica juncea

<400> SEQUENCE: 52
ccagagatga tcaaaggtct cagggcccat actgatgcag gaggcatcat cttgttgttt       60
caagatgaca aggtcagtgg tctccagctt cttaaagatg gtgactggat tgatgttcct      120
ccactcaacc actctattgt catcaatctt ggtgaccaac ttgaggtgat aaccaacggc      180
aggtacaaga gtgtgatgca ccgtgtggtg actcagaaag aaggaaacag aatgtctatt      240
gcatctttct acaacccggg                                                  260

<210> SEQ ID NO 53
<211> LENGTH: 260
<212> TYPE: DNA
<213> ORGANISM: Brassica napus

<400> SEQUENCE: 53
cctgagatga tcaaagggct tagggctcac acagatgcag gaggcctcat cttgttgttt       60
caagacgata aagtcagtgg ccttcagctt ctcaaagatg gtgattgggt tgatgttcct      120
ccactcaagc actccattgt catcaatctt ggtgaccaac ttgaggtgat aacaaacggg      180
tggtacaaga gcataatgca tcgtgtaatg actcaaaaag aaggaaacag gatgtctatt      240
gcgtccttct acaaccctgg                                                  260

<210> SEQ ID NO 54
<211> LENGTH: 260
<212> TYPE: DNA
<213> ORGANISM: Brassica oleracea

<400> SEQUENCE: 54
ccagagatga tcaaaggtct tagggcccac actgatgcag gaggcatcat cttgttgttt       60
caagatgaca aggtcagtgg tctccagctt cttaaagatg gtgactggat tgatgttcct      120
ccactcaacc actctattgt catcaatctt ggtgaccaac ttgaggtgat aaccaacggc      180
aggtacaaga gtgtgatgca tcgtgtggtg actcagaaag aaggaaacag aatgtcaatt      240
gcatctttct acaacccggg                                                  260
```

<210> SEQ ID NO 55
<211> LENGTH: 260
<212> TYPE: DNA
<213> ORGANISM: Brassica oleracea

<400> SEQUENCE: 55

| | | | | | |
|---|---|---|---|---|---|
| ccggagatga | tcaaagggct | tagggctcac | acggatgcag | gaggcctcat | attgctattt | 60 |
| caagacgata | aggtcagtgg | tcttcagctt | ctcaaagatg | gtgtttgggt | tgatgtccct | 120 |
| cctctcaaac | actccattgt | catcaatctt | ggtgaccaac | ttgaggtgat | aaccaacggg | 180 |
| aagtacaaga | gcataatgca | ccgtgtgatg | acacaaaaag | aaggaaacag | gatgtctata | 240 |
| gcgtcgttct | acaaccctgg | | | | | 260 |

<210> SEQ ID NO 56
<211> LENGTH: 260
<212> TYPE: DNA
<213> ORGANISM: Brassica rapa

<400> SEQUENCE: 56

| | | | | | |
|---|---|---|---|---|---|
| cctgagatga | tcaaagggct | tagggctcac | acagacgcag | gaggcctcat | cttgttgttt | 60 |
| caagacgata | aagtcagtgg | ccttcagctt | ctcaaagatg | gtgattgggt | tgatgttcct | 120 |
| ccactcaagc | actccattgt | catcaatctt | ggtgaccaac | ttgaggtgat | aacaaacggg | 180 |
| aagtacaaga | gcgtaatgca | tcgcgtcatg | actcaaaaag | aaggaaacag | gatgtctatt | 240 |
| gcgtccttct | acaaccctgg | | | | | 260 |

<210> SEQ ID NO 57
<211> LENGTH: 260
<212> TYPE: DNA
<213> ORGANISM: Brassica rapa

<400> SEQUENCE: 57

| | | | | | |
|---|---|---|---|---|---|
| ccagagatga | taaaaggtct | tagggcccac | actgatgcag | gaggcatcat | cttgttgttt | 60 |
| caagatgaca | aggtcagtgg | tctccagctt | cttaaagatg | gtgactggat | tgatgttcct | 120 |
| ccactcaacc | actctattgt | catcaatctt | ggtgaccaac | ttgaggtgat | aactaacggc | 180 |
| aggtacaaga | gtgtgatgca | ccgtgtggtg | actcagaaag | aaggaaacag | aatgtcaatt | 240 |
| gcatctttct | acaacccggg | | | | | 260 |

<210> SEQ ID NO 58
<211> LENGTH: 260
<212> TYPE: DNA
<213> ORGANISM: Carica papaya

<400> SEQUENCE: 58

| | | | | | |
|---|---|---|---|---|---|
| ccagatctta | tcgagggact | cagagcccac | acagatgcag | gtggcatcat | cttgttgttc | 60 |
| caagatggca | aggtcagtgg | cctccagctc | ctcaaggatg | accagtgggt | tgatgtccct | 120 |
| cccatgaaac | attccattgt | catcaacctt | ggtgatcaac | ttgaggtgat | tactaacggt | 180 |
| aaatacaaga | gtgtaatgca | cagagttata | gcacagacag | atgggaacag | aatgtcacta | 240 |
| gcctcattct | acaatcctgg | | | | | 260 |

<210> SEQ ID NO 59
<211> LENGTH: 260
<212> TYPE: DNA
<213> ORGANISM: Lycopersicon esculentum

<400> SEQUENCE: 59

-continued

```
ccagacttga tcaaaggcct tcgcgctcac acggatgctg gtggcatcat ccttctattc      60
caagatgaca aagtcagtgg tctccaattg ctaaagatg gcaattggat tgatgtacct      120
cctatgaaac actctattgt catcaacctc ggcgatcagc tagaggtgat tactaatgga     180
agatacaaga gtattgagca cagagtgatt gctcaacaag atggcactag gatgtcaata     240
gcttcctttt ataatccagg                                                 260

<210> SEQ ID NO 60
<211> LENGTH: 260
<212> TYPE: DNA
<213> ORGANISM: Malus domestica

<400> SEQUENCE: 60
ccagacctga tcaagggact ccgggcccac agcgacgccg gtggcatcat cctgcttttc     60
caggatgaca aggtcagcgg cctccagctt ctcaaggatg gtgaatgggt ggatgtcccc    120
ccaatgcacc actccattgt cataaactta ggtgaccaga ttgaggtgat caccaatggg    180
aagtacaaaa gtgtgatgca ccgggtgata gctcagtcgg atgggaccag aatgtcgata    240
gcctcgttct acaacccagg                                                260

<210> SEQ ID NO 61
<211> LENGTH: 260
<212> TYPE: DNA
<213> ORGANISM: Malus domestica

<400> SEQUENCE: 61
ccagacctga tcaagggact ccgggcccac accgacgctg gtggtatcat cctgcttttc     60
caggatgaca aggtcagtgg cctccagctc ctcaaggatg gtgaatggat ggatgtcccc    120
ccagtgcacc actccattgt catcaactta ggtgaccaga ttgaggtgat cactaatggg    180
aagtacaaga gtataatgca ccgggtgata gctcagtcgg acggaaccag aatgtcgata    240
gcgtcgttct acaacccggg                                                260

<210> SEQ ID NO 62
<211> LENGTH: 260
<212> TYPE: DNA
<213> ORGANISM: Nicotiana glutinosa

<400> SEQUENCE: 62
cccgatttga ttaaaggcct cagggctcac actgatgctg gtggaatcat ccttctattc     60
caagatgaca aagtcagtgg tctgcaacta ctcaaagatg acaaatggat cggtgttcca    120
ccaatgcgcc actccattgt catcaacctc ggtgaccaac ttgaggtgat tactaatgga    180
aagtacaaga gtatggagca tagggtgatt gctcagcctg atggaaacag aatgtccatt    240
gcttccttct ataacccggg                                                260

<210> SEQ ID NO 63
<211> LENGTH: 260
<212> TYPE: DNA
<213> ORGANISM: Nicotiana glutinosa

<400> SEQUENCE: 63
ccagaattaa taaagggtct aagggctcac acagatgcag gtggaatcat acttctattc     60
caagatgaca aagtcagtgg gttacagctc ctaaaagatg gtaaatggat tgatgtccca    120
ccaatgagcc actccaattgt tgtcaatatt ggagaccaac tagaggtgat cacaaatgga   180
```

```
aaatacaaga gtgtggagca cagggtaatt gctcagccag atgggaacag gatgtccata    240
gcatctttct acaatccagg                                                260

<210> SEQ ID NO 64
<211> LENGTH: 260
<212> TYPE: DNA
<213> ORGANISM: Pisum sativum

<400> SEQUENCE: 64
ccggaactca tcaagggact tagagctcac acagatgccg gcggaatcat tcttctcttc    60
caagatgaca aagtcagtgg acttcagctt ctcaaagatg accaatggat tgatgtccct    120
ccaatgcgtc actctattgt catcaatctt ggtgatcaac tcgaggtgat aaccaatgga    180
aagtacaaga gtgtgatgca tagagtaata gcacaaacag atggtgctag aatgtccata    240
gcatccttct acaatccagg                                                260

<210> SEQ ID NO 65
<211> LENGTH: 260
<212> TYPE: DNA
<213> ORGANISM: Pyrus pyrifolia

<400> SEQUENCE: 65
ccagacctga tcaagggact ccgggcccac agcgacgccg gtggcatcat cctgcttttc    60
caggatgaca aggtcagcgg cctccagctt ctcaaggatg gtgaatgggt ggatgtcccc    120
ccaatgcacc actccattgt cataaactta ggtgaccaga ttgaggtgat caccaatggg    180
aagtacaaga gtgtgatgca ccgggtgata gctcagtcgg acgggaccag aatgtcgata    240
gcctcgttct acaacccagg                                                260

<210> SEQ ID NO 66
<211> LENGTH: 260
<212> TYPE: DNA
<213> ORGANISM: Solanum tuberosum

<400> SEQUENCE: 66
cctgatctca ttaaaggcct gagggctcac acagatgctg gtggcatcat ccttctattc    60
caagatgaca aagtcagtgg tctccaacta ctcaaagatg gcaaatggat tgatgttcca    120
aaatacaaga gtgtggagca cagggtgatt gctcagcctg atggaaacag aatgtccttg    180
ccaatgcgcc actccattgt catcaacctc ggtgaccaac tcgaggtgat taccaatgga    240
gcttcgttct ataatccggg                                                260

<210> SEQ ID NO 67
<211> LENGTH: 260
<212> TYPE: DNA
<213> ORGANISM: Vigna radiata

<400> SEQUENCE: 67
cctgatctga taagggcct aagagctcac actgatgccg gtggcattat cctactgttc    60
caagatgaca aggtcagtgg actgcagctc ctcaaggatg accagtggat cgatgtccca    120
ccaatgcgtc actccattgt catcaacctt ggtgaccaac ttgaggtcat aaccaatggc    180
aagtacaaga gtgtcatgca ccgagtcatt gctcagacgg atggcaccag aatgtccctg    240
gcttccttct ataatcccgg                                                260

<210> SEQ ID NO 68
<211> LENGTH: 260
```

```
<212> TYPE: DNA
<213> ORGANISM: Artificial Sequence
<220> FEATURE:
<223> OTHER INFORMATION: Description of Artificial Sequence:  Block 1
      ACO Synthetic Sequence

<400> SEQUENCE: 68
ccagagctga tcaagggcct tcgggctcac acagatgctg gtggcatcat cctgctgttc      60
caagatgaca aggtcagtgg tctccagctt ctcaaagatg gtgattggat tgatgttcct     120
ccaatgaacc actccattgt catcaatctt ggtgaccagc ttgaggtgat taccaatgga     180
aaatacaaga gtgtgatgca ccgtgtgatt gctcagacag atggaaacag aatgtcaata     240
gcatcgttct acaatccggg                                                 260

<210> SEQ ID NO 69
<211> LENGTH: 216
<212> TYPE: DNA
<213> ORGANISM: Australia-Bridgeman-Downs-PRSV

<400> SEQUENCE: 69
gctagatacg ctttcgattt ctatgaggtg aattcgaaaa cacctgatag ggctcgcgaa      60
gctcacatgc agatgaaagc tgcagcgctg cgaaacacta gtcgcagaat gtttggtatg     120
gacggcagtg ttagtaacaa ggaagaaaac acggagagac acacagtgga agatgtcaat     180
agagacatgc actctctcct gggtatgcac aactga                               216

<210> SEQ ID NO 70
<211> LENGTH: 216
<212> TYPE: DNA
<213> ORGANISM: Australia-Bundaberg-PRSV

<400> SEQUENCE: 70
gctagatacg ctttcgattt ctatgaggtg aattcgaaaa cacctgatag ggctcgcgaa      60
gctcacatgc agatgaaagc tgcagcgctg cgaaacacta gtcgcagaat gtttggtatg     120
gacggcagtg ttagtaacag ggaagaaaac acggagagac acacagtgga agatgtcaat     180
agagacatgc actctctcct gggtatgcgc aactga                               216

<210> SEQ ID NO 71
<211> LENGTH: 216
<212> TYPE: DNA
<213> ORGANISM: Australia-PRSV

<400> SEQUENCE: 71
gctagatacg ctttcgattt ctatgaggtg aattcgaaaa cacctgatag ggctcgcgaa      60
gctcacatgc agatgaaagc tgcagcgctg cgaaacacta gtcgcagaat gtttggtatg     120
gacggcagtg ttagtaacaa ggaagaaaac acggagagac acacagtgga agatgtcaat     180
agagacatgc actctctcct gggtatgcgc aactga                               216

<210> SEQ ID NO 72
<211> LENGTH: 216
<212> TYPE: DNA
<213> ORGANISM: Australia-Wellington-Point-PRSV

<400> SEQUENCE: 72
gctagatacg ctttcgattt ctatgaggtg aattcgaaaa cacctgatag ggctcgcgaa      60
gctcacatgc agatgaaagc tgcagcgctg cgaaacactg gtcgcagaat gtttggtatg     120
gacggcagtg ttagtaacaa ggaagaaaac acggagagac acacagtgga agatgtcaat     180
```

```
agagacatgc actctctcct gggtatgcgc aactga                                      216

<210> SEQ ID N

```
gacggcaatg tcagtaacaa ggaagaaaac acggagaggc acacagtgga agatgtcaat      180
agagacatgc actctctcct gggtatgcgc aactga                               216

<210> SEQ ID NO 78
<211> LENGTH: 216
<212> TYPE: DNA
<213> ORGANISM: Brasil-Ceara-PRSV

<400> SEQUENCE: 78
gccagatatg ctttcgattt ctatgaggtg aattcgaaaa cacctgatag agctcgtgaa      60
gctcatatgc agatgaaagc tgcagcgctg cgaaacacta atcgcagaat gtttggtatg     120
gacggcagtg ttagtaacaa ggaagaaaac acggagagac acacagtgga agatgtcaac     180
agagacatgc actctctcct gggtatgcgc aactga                               216

<210> SEQ ID NO 79
<211> LENGTH: 216
<212> TYPE: DNA
<213> ORGANISM: Brasil-EspiritoSanto-PRSV

<400> SEQUENCE: 79
gctagatatg ctttcgattt ctatgaggtg aattcgaaaa cacctgatag ggctcgcgaa      60
gctcacatgc agatgaaagc tgcagcgctg cgaaacacta atcgtagaat gtttggtatg     120
gacggcagtg tcagtaacaa ggaagaaaac acggagagtc acacagtgga agatgtcaat     180
agagacatgc actctctcct gggtatgcgc aactga                               216

<210> SEQ ID NO 80
<211> LENGTH: 216
<212> TYPE: DNA
<213> ORGANISM: Brasil-Paraiba-PRSV

<400> SEQUENCE: 80
gctagatatg ctttcgattt ctatgaggtg aattcgaaaa cacctgatag ggctcgtgaa      60
gctcatatgc agatgaaagc tgcagcgctg cgaaacacta atcgcagaat gtttggtatg     120
gacggcagtg ttagtaacaa ggaagaaaac acggagagac acacagtgga agatgtcaat     180
agagacatgc actctctcct gggtatgcgc aactga                               216

<210> SEQ ID NO 81
<211> LENGTH: 216
<212> TYPE: DNA
<213> ORGANISM: Brasil-Parana-PRSV

<400> SEQUENCE: 81
gctagatatg ctttcgattt ctatgaggtg aattcgaaaa cacctgatag ggctcgcgaa      60
gctcacatgc agatgaaagc tgcagcgctg cgaaacacta atcgcagaat gtttggtatg     120
gacggcagtg ttagtaacaa ggaagaaaac acggagagac acacagtgga agatgtcaat     180
agagacatgc actctctcct gggtatgcgc aactga                               216

<210> SEQ ID NO 82
<211> LENGTH: 216
<212> TYPE: DNA
<213> ORGANISM: Brasil-Pernambuco-PRSV

<400> SEQUENCE: 82
gctagatatg ctttcgattt ctatgaggtg aattcgaaaa cacctgatag ggctcgtgaa      60
gctcatatgc agatgaaagc tgcagcgctg cgaaacacta atcgcagaat gtttggtatg     120
```

```
gacggcagtg ttagtaacaa ggaagaaaac acggagagac acacagtgga agatgtcaat    180
agagacatgc actctctcct gggtatgcgc aactga                              216

<210> SEQ ID NO 83
<211> LENGTH: 216
<212> TYPE: DNA
<213> ORGANISM: Brasil-SaoPaulo-PRSV

<400> SEQUENCE: 83
gctagatatg ctttcgattt ctatgaggtg aattcgaaaa cacctgatag ggctcgcgaa    60
gctcacatgc agatgaaagc tgcagcgctg cgaaacacta atcgcagaat gtttggtatg    120
gacggcagtg tcagtaacaa ggaagaaaac acggagaggc acacagtgga agatgtcaat    180
agagacatgc actctctcct gggtatgcgc aactga                              216

<210> SEQ ID NO 84
<211> LENGTH: 216
<212> TYPE: DNA
<213> ORGANISM: China-Severe-PRSV

<400> SEQUENCE: 84
gctagatatg ctttcgattt ctatgaggtg aattcaaaaa cacctgatag ggctcgtgaa    60
gctcatatgc agatgaaagc tgcagccgtg cgcaacacta atcgcagaat gtttggaatg    120
gacggcagtg tcagtaacaa ggaagaaaac acggagagac acacagtgga agatgtcaac    180
agagacatgc actctctcct gggtatgcgc aattga                              216

<210> SEQ ID NO 85
<211> LENGTH: 216
<212> TYPE: DNA
<213> ORGANISM: China-Xiao-PRSV

<400> SEQUENCE: 85
gctagatatg ctttcgattt ctatgaggtg aattcaaaaa cacctgatag ggctcgtgaa    60
gctcatatgc agatgaaagc tgcagcgctg cgcaacacta ctcgcagact gtttggaatg    120
gacggcagtg tcagtaacaa ggaagaaaac acggagagac acacagtgga agatgtcaac    180
agagacatgc actctctcct gggtatgcgc aactaa                              216

<210> SEQ ID NO 86
<211> LENGTH: 216
<212> TYPE: DNA
<213> ORGANISM: FloridaH1K-PRSV

<400> SEQUENCE: 86
gccagatacg ctttcgattt ctatgaggta aattcgaaaa cacctgatag agctcgcgaa    60
gctcacatgc agatgaaagc tgcagcactg cgaaatgcta gtcgcagaat gtttggtatg    120
gacggcagtg ttagtaacaa ggaagaaaac acggagagac acacagtgga agatgtcaat    180
agagacatgc actctctcct gggtatgcgc aactga                              216

<210> SEQ ID NO 87
<211> LENGTH: 216
<212> TYPE: DNA
<213> ORGANISM: Hawaii-KEAAU(Geneva)-PRSV

<400> SEQUENCE: 87
gctagatatg ctttcgactt ctatgaggtg aattcgaaaa cacctgatag ggctcgcgaa    60
```

| | |
|---|---|
| gcccacatgc agatgaaggc tgcagcgctg cgaaacacta gtcgcagaat gtttggtatg | 120 |
| gacggcagtg ttagtaacaa ggaagaaaac acggagagac acacagtgga agatgtcaat | 180 |
| agagacatgc actctctcct gggcatgcgc aactaa | 216 |

<210> SEQ ID NO 88
<211> LENGTH: 216
<212> TYPE: DNA
<213> ORGANISM: Hawaii-OAHU(Geneva)-PRSV

<400> SEQUENCE: 88

| | |
|---|---|
| gctagatacg ctttcgactt ttatgaggtg aattcgaaaa cacctgatag agctcgcgaa | 60 |
| gctcacatgc agatgaaggc tgcagcgctg cgaaacacca gtcgcagaat gtttggtatg | 120 |
| gacggcagtg ttagtaacaa ggaagaaaac acggagagac acacagtgga agatgtcaat | 180 |
| agagacatgc actctctcct gggtatgcgc aactaa | 216 |

<210> SEQ ID NO 89
<211> LENGTH: 216
<212> TYPE: DNA
<213> ORGANISM: Hawaii-PRSV

<400> SEQUENCE: 89

| | |
|---|---|
| gctagatacg ctttcgactt ctatgaggtg aattcgaaaa cacctgatag ggctcgcgaa | 60 |
| gctcacatgc agatgaaggc tgcagcgctg cgaaacacca gtcgcagaat gtttggtatg | 120 |
| gacggcagtg ttagtaacaa ggaagaaaac acggagagac acacagtgga agatgtcaat | 180 |
| agagacatgc actctctcct gggtatgcgc aactaa | 216 |

<210> SEQ ID NO 90
<211> LENGTH: 216
<212> TYPE: DNA
<213> ORGANISM: India-Bangalore-PRSV

<400> SEQUENCE: 90

| | |
|---|---|
| gctagatatg ctttcgattt ctatgaggtg aattcaaaaa cacctgatag agctcgagag | 60 |
| gctcatatgc agatgaaggc agctgcactg cggaacacaa atcgcagaat gtttggaatg | 120 |
| gacggcagtg tcagtaacaa ggaagaaaac acggagagac acacagtgga agatgtcaat | 180 |
| agagacatgc actctctcct gggtatgcgc aactga | 216 |

<210> SEQ ID NO 91
<211> LENGTH: 216
<212> TYPE: DNA
<213> ORGANISM: India-Chiengmai1-PRSV

<400> SEQUENCE: 91

| | |
|---|---|
| gctagatatg ctttcgactt ctatgaagtg aactcaaaga cacctgatag ggctcgtgaa | 60 |
| gctcacatgc agatgaaggc tgcagcgctg cgtaacacta gtcgcagaat gtttggaatg | 120 |
| gatggcagtg tcagtaacaa ggaagaaaac acggagagac acacagtgga agatgttaac | 180 |
| agagacatgc actctctcct aggtatgcgc aattga | 216 |

<210> SEQ ID NO 92
<211> LENGTH: 216
<212> TYPE: DNA
<213> ORGANISM: India-Chiengmai2-PRSV

<400> SEQUENCE: 92

| | |
|---|---|
| gctagatatg ctttcgactt ctatgaggtg aactcaaaga cacctgatag ggctcgtgaa | 60 |

```
gctcatatgc agatgaaggc tgcagcgctg cgcaacacta gtcgcagaat gtttggaatg    120
gacggcagtg ttagtaacaa ggaagaaaac acggagagac acacagtgga ggatgttaac    180
agagacatgc actctctcct aggtatgcgc aattga                              216

<210> SEQ ID NO 93
<211> LENGTH: 216
<212> TYPE: DNA
<213> ORGANISM: India-PRSV-P

<400> SEQUENCE: 93
gctagatacg ctttcgattt ctatgaggtg aattcgaaaa cacctgatag ggctcgcgaa     60
gctcacatgc agatgaaagc tgcggcattg cgaaacacta atcgcaggat gtttggtatg    120
gacggcagtg tcagtaacaa ggaagagaac acggagagac acacagtaga agatgtcaat    180
agagacatgc actctctcct gggtatgcgc aactga                              216

<210> SEQ ID NO 94
<211> LENGTH: 216
<212> TYPE: DNA
<213> ORGANISM: India-Ratchaburi-PRSV

<400> SEQUENCE: 94
gctagatatg ctttcgactt ctatgaggtg aactcaaaaa cacctgatag ggctcgtgaa     60
gctcatatgc agatgaaggc tgcagcgctg cgcaacactg gtcgcagaat gtttggaatg    120
gacggcagtg tcagtaacaa ggaagaaaac acggagagac acacagtgga agatgtcaac    180
agagacatgc actctctcct gggtatgcgc aattga                              216

<210> SEQ ID NO 95
<211> LENGTH: 216
<212> TYPE: DNA
<213> ORGANISM: Indonesia1-PRSV

<400> SEQUENCE: 95
gctagatatg ctttcgactt ctatgaggtg aattcaaaaa cacctgatag ggctcgtgaa     60
gctcatatgc agatgaaggc tgcagcgctg cgcaacacta gtcgcagaat gtttggaatg    120
gacggcagtg tcagtaacaa ggaagaaaac acggagagac acacagtgga agatgtaaac    180
agagacatgc actctctcct aggtatgcgc aattga                              216

<210> SEQ ID NO 96
<211> LENGTH: 216
<212> TYPE: DNA
<213> ORGANISM: Indonesia2-PRSV

<400> SEQUENCE: 96
gctagatatg ctttcgactt ctatgaggtg aactcaaaaa cacctgatag ggctcgtgaa     60
gctcatatgc agatgaaggc tgcagcgctg cgcaacacta gtcgcagaat gtttggaatg    120
gacggcagtg tcagtaacaa ggaagaaaac acggagagac acacagtgga agatgttaac    180
agagacatgc actctctcct aggtatgcgc aattga                              216

<210> SEQ ID NO 97
<211> LENGTH: 216
<212> TYPE: DNA
<213> ORGANISM: Jamaica(Geneva)-PRSV

<400> SEQUENCE: 97
```

```
gctagatacg ctttcgattt ctatgaggtg aattcgaaga cacctgatag ggctcgtgaa      60
gctcacatgc agatgaaagc tgcagcgctg cgaaacacta atcgcagaat gtttggtatg     120
gacggcagtg ttagtaacaa tgaagaaaac acggagagac acacagtgga agatgtctat     180
atagacatgc actctctcct gcgtttgcgc aactga                               216

<210> SEQ ID NO 98
<211> LENGTH: 216
<212> TYPE: DNA
<213> ORGANISM: Japan-Okinawa-Maoka-PRSV

<400> SEQUENCE: 98
gctagatatg ctttcgattt ctatgaggtg aattcgaaga cacctgatag ggctcgtgaa      60
gctcatatgc agatgaaggc tgcagcgcta cgcaatgcta atcgcagaat gtttgggatg     120
gacggcagtg tcagtaacaa ggaagaaaac acggagagac acacagtgga agatgtcaac     180
agagacatgc actctctcct gggtatgcgc aattga                               216

<210> SEQ ID NO 99
<211> LENGTH: 216
<212> TYPE: DNA
<213> ORGANISM: Japan-PRSV-S

<400> SEQUENCE: 99
gccagatatg ctttcgattt ctatgaggtg aattcaaaaa cacctgatag ggctcgtgaa      60
gctcatatgc agatgaaggc tgcagcgcta cgcaatacta gtcgcagaat gtttggaatg     120
gacggcagtg tcagtaacaa ggaagaaaac acggagagac acacagtgga agatgtcaac     180
agagacatgc actctctcct gggtatgcgc aattga                               216

<210> SEQ ID NO 100
<211> LENGTH: 216
<212> TYPE: DNA
<213> ORGANISM: Japan-Hanada-PRSV

<400> SEQUENCE: 100
gccagatatg ctttcgattt ctatgaggtg aattcaaaaa cacctgatag ggctcgtgaa      60
gctcatatgc agatgaaggc tgcagcacta cgcaatacta gtcgcagaat gtttggaatg     120
gacggcagtg tcagtaacaa ggaagaaaac acggagagac acacagtgga agatgtcaac     180
agagacatgc actctctcct gggtatgcgc aattga                               216

<210> SEQ ID NO 101
<211> LENGTH: 216
<212> TYPE: DNA
<213> ORGANISM: Malaysia-Maoka-PRSV

<400> SEQUENCE: 101
gctagatatg ctttcgattt ctatgaggtg aattcgaaaa cacctgatag ggctcgtgaa      60
gctcatatac agatgaaagc tgcagcgcta cgcaataata atcgcaaagt gtttggattg     120
gacggcagtg tcagtaacaa ggaagaaaac acggagagac acacagtgga agatgtcaac     180
agagacatgc actctctcct gggtatgcgc aattga                               216

<210> SEQ ID NO 102
<211> LENGTH: 216
<212> TYPE: DNA
<213> ORGANISM: Mexico-Chiapas-30-PRSV

<400> SEQUENCE: 102
```

```
gctagatacg ctttcgattt ttatgaggtg aattcaaaaa cacctgatag agctcgcgaa        60
gctcacatgc agatgaaagc tgcagcgctg cgaaattcta atcgcagaat gtttggtatg       120
gatggcagtg ttagtaacaa ggaagaaaac acggagagac acacagtgga agatgtcaat       180
agagacatgc actctctcct gggtatgcgc aactga                                 216
```

<210> SEQ ID NO 103
<211> LENGTH: 216
<212> TYPE: DNA
<213> ORGANISM: Mexico-Chiapas-39-PRSV

<400> SEQUENCE: 103

```
gctagatacg ctttcgattt ttatgaggtg aattccaaaa cacctgatag agctcgcgaa        60
gctcacatgc agatgaaagc tgcagcgctg cgaaattcta atcgcagaat gtttggtatg       120
gatggcagtg ttagtaacaa ggaagaaaac acggagagac acacagtgga agatgtcaat       180
agagacatgc actctctcct gggtatgcgc aactga                                 216
```

<210> SEQ ID NO 104
<211> LENGTH: 216
<212> TYPE: DNA
<213> ORGANISM: Mexico-Chiapas-40-PRSV

<400> SEQUENCE: 104

```
gctagatacg ctttcgattt ttatgaggtg aattcaaaaa cacctgatag agctcgcgaa        60
gctcacatgc agatgaaagc tgcagcgctg cgaaattcta atcgcagaat gtttggtatg       120
gatggcagtg ttagtaacaa ggaagaaaac acggagagac acacagtgga agatgtcaat       180
agagacatgc actctctcct gggtatgcgc aactga                                 216
```

<210> SEQ ID NO 105
<211> LENGTH: 216
<212> TYPE: DNA
<213> ORGANISM: Mexico-ChiapasChT11-PRSV

<400> SEQUENCE: 105

```
gctagatacg ctttcgattt ttatgaggtg aattcaaaaa cacctgatag agctcgcgaa        60
gctcacatgc agatgaaagc tgcagcgctg cgaaattcta atcgcagaat gtttggtatg       120
gatggcagtg ttagtaacaa ggaagaaaac acggagagac acacagtgga agatgtcaat       180
agagacatgc actctctcct gggtatgcgc aactaa                                 216
```

<210> SEQ ID NO 106
<211> LENGTH: 216
<212> TYPE: DNA
<213> ORGANISM: Mexico-Colima-PRSV

<400> SEQUENCE: 106

```
gctagatacg ctttcgattt ctatgaggtg aattcgaaaa cacctgatag ggctcgcgaa        60
gctcacatgc agatgaaagc tgcagcgctg cgaaacacta atcgcagaat gtgtggtatg       120
gacggcagtg ttagtaacaa ggaagaaaac acagagagac acacagtgga agatgtcaat       180
agagacatgc actctctcct gggtatgcgc aactga                                 216
```

<210> SEQ ID NO 107
<211> LENGTH: 216
<212> TYPE: DNA
<213> ORGANISM: Mexico-Guerrero-9-PRSV -continued

```
<400> SEQUENCE: 107
gctagatacg ctttcgattt ctatgaggtg aattcgaaaa cacctgatag ggctcgcgaa      60
gctcacatgc agatgaaggc tgcagcgctg cgaaacacta gtcgcagaat gtttggtatg     120
gatggcagtg ttagtaacaa ggaagaaaac acggagagac acacagtgga agatgtcaat     180
agagacatgc actctctcct gggtatgcgc aactga                               216

<210> SEQ ID NO 108
<211> LENGTH: 216
<212> TYPE: DNA
<213> ORGANISM: Mexico-Jalisco-13-PRSV

<400> SEQUENCE: 108
gctaagtacg ctttcgattt ctatgaggtg aattcgaaaa cacctgatag ggctcgcgaa      60
gctcacatgc agatgaaagc tgcagcgctg cgaaacacta atcgcagaat gtttggtatg     120
gacggcagtg ttagtaacaa ggaagaaaac acagagagac acacagtgga agatgtcaat     180
agagacatgc actctctcct gggtatgcgc aactga                               216

<210> SEQ ID NO 109
<211> LENGTH: 216
<212> TYPE: DNA
<213> ORGANISM: Mexico-Jalisco-14-PRSV

<400> SEQUENCE: 109
gctagatacg ctttcgattt ctatgaggtg aattcgaaaa cacctgatag ggctcgcgaa      60
gctcacatgc agatgaaagc tgcagcactg cgaaacacta gtcgcagaat gtttggtatg     120
gatggcagtg ttagtaacaa ggaagaaaac acagagagac acacagtgga ggatgtcaat     180
agagacatgc actctctcct gggtatgcgc aactga                               216

<210> SEQ ID NO 110
<211> LENGTH: 216
<212> TYPE: DNA
<213> ORGANISM: Mexico-Jalisco-39-PRSV

<400> SEQUENCE: 110
gctagatacg cttttgattt ctatgaggtg aattcgaaaa cacctgatag ggctcgcgaa      60
gctcacatgc agatgaaagc tgcagcactg cgaaacacta gtcgcagaat gtttggtatg     120
gatggcagtg ttagtaacaa ggaagaaaac acagagagac acacagtgga agatgtcaat     180
agagacatgc actctctcct gggtatgcgt aactga                               216

<210> SEQ ID NO 111
<211> LENGTH: 216
<212> TYPE: DNA
<213> ORGANISM: Mexico-Michoacan-18-PRSV

<400> SEQUENCE: 111
gctagatacg ctttcgattt ctatgaggtg aattcgaaaa cacctgatag ggctcgcgaa      60
gctcacatgc agatgaaggc tgcagcactg cgaaacacta gtcgcagaat gtttggtatg     120
gacggcagtg ttagtaacaa ggaagaaaac acggagagac acacagtgga agatgtcaat     180
agagacatgc actctctcct gggtatgcgc aactga                               216

<210> SEQ ID NO 112
<211> LENGTH: 216
<212> TYPE: DNA
<213> ORGANISM: Mexico-Michoacan-57-PRSV
```

<400> SEQUENCE: 112

```
gctagatacg ctttcgattt ctatgaggtg aattcaaaaa cacctgatag ggctcgcgaa      60
gctcacatgc agatgaaggc tgcagcactg cgaaacacta gtcgcagaat gtttggtatg     120
gatggcagtg ttagtaacaa ggaagaaaac acggagagac acacagtgga agatgtcaat     180
agagacatgc actctctcct gggtatgcgc aactga                               216
```

<210> SEQ ID NO 113
<211> LENGTH: 216
<212> TYPE: DNA
<213> ORGANISM: Mexico-Nayarit-22-PRSV

<400> SEQUENCE: 113

```
gctagatacg ctttcgattt ctatgaggtg aattcgaaaa cacctgatag ggctcgcgaa      60
gctcacatgc agatgaaagc tgcagcactg cgaaacacta gtcgcagaat gtttggtatg     120
gatggcagtg ttagtaacaa ggaagaaaac acagagagac acacagtgga ggatgtcaat     180
agagacatgc actctctcct gggtatgcgc aactga                               216
```

<210> SEQ ID NO 114
<211> LENGTH: 216
<212> TYPE: DNA
<213> ORGANISM: Mexico-Oaxaca-T27-PRSV

<400> SEQUENCE: 114

```
gctagatatg ctttcgattt ctatgaggtg aattcgaaaa cacctgatag ggctcgcgaa      60
gctcacatgc agatgaaggc tgcagcactg cgaaacacta gtcgcagaat gtttggtatg     120
gacggcagtg ttagtaacaa ggaagaaaac acggagagac acacagtgga agatgtcaat     180
ggagacatgc actctctcct gggtatgcgc aactga                               216
```

<210> SEQ ID NO 115
<211> LENGTH: 216
<212> TYPE: DNA
<213> ORGANISM: Mexico-Oaxaca-T66-PRSV

<400> SEQUENCE: 115

```
gctagatatg ctttcgattt ttatgaggtg aactcgaaaa cacctgatag ggctcgcgaa      60
gctcacatgc agatgaaggc tgcagcactg cgaaacacta gtcgcagaat gtttggtatg     120
gacggcagtg ttagtaacaa ggaagaaaac acggagagac acacagtgga agatgtcaat     180
agagacatgc actctctcct gggtatgcgc aactga                               216
```

<210> SEQ ID NO 116
<211> LENGTH: 216
<212> TYPE: DNA
<213> ORGANISM: Mexico-Oaxaca-T80-PRSV

<400> SEQUENCE: 116

```
gctagatatg ctttcgattt ctatgaggtg aattcgaaaa cacctgatag ggctcgcgaa      60
gctcacatgc agatgaaggc tgcagcactg cgaaacacta gtcgcagaat gtttggtatg     120
gacggcagtg ttagtaacaa ggaagaaaac acggagagac acacagtgga agatgtcaat     180
agagacatgc actctctcct gggtaagcgc aactga                               216
```

<210> SEQ ID NO 117
<211> LENGTH: 216
<212> TYPE: DNA

<213> ORGANISM: Mexico-Potosi-27-PRSV

<400> SEQUENCE: 117

```
gctagatacg ctttcgattt ctatgaggtg aattcgaaaa cacctgatag ggctcgtgaa      60
gctcacatgc agatgaaagc tgcagcgctg cgaaacacta atcgcagaat gtttggcatg     120
gacggcagtg ttagtaacaa ggaagaaaat acggagagac acacagtgga agatgtcaac     180
agagacatgc actctctcct gggtatgcgc aactga                               216
```

<210> SEQ ID NO 118
<211> LENGTH: 216
<212> TYPE: DNA
<213> ORGANISM: Mexico-QuintanaRoo-FC-1-PRSV

<400> SEQUENCE: 118

```
gccagatacg ctttcgactt ctatgaggtg aattcgaaaa cacctgatag ggctcgcgaa      60
gcccacatgc agatgaaggc tgcagcgctg cgaagcacta gtcgcagaat gtttggtatg     120
gatggcagtg ttagtaacaa ggaagaaaac acggagagac acacagtgga agatgtcaat     180
agagacatgc actctctcct gggtatgcgc aactga                               216
```

<210> SEQ ID NO 119
<211> LENGTH: 216
<212> TYPE: DNA
<213> ORGANISM: Mexico-QuintanaRoo-FC-2-PRSV

<400> SEQUENCE: 119

```
gccagatacg ctttcgactt ctatgaggtg aattcgaaaa cacctgatag ggctcgcgaa      60
gcccacatgc agatgaaggc tgcagcgctg cgaagcacta gtcgcagaat gtttggtatg     120
gatggcagtg ttagtaacaa ggaagaaaac acggagagac acacagtgga agatgtcaat     180
agagacatgc actctctcct gggtatgcgc aactga                               216
```

<210> SEQ ID NO 120
<211> LENGTH: 216
<212> TYPE: DNA
<213> ORGANISM: Mexico-QuintanaRoo-FC-3-PRSV

<400> SEQUENCE: 120

```
gccagatacg ctttcgactt ctatgaggtg aattcgaaaa cacctgatag ggctcgcgaa      60
gcccacatgc agatgaaggc tgcagcgctg cgaagcacta gtcgcagaat gtttggtatg     120
gatggcagtg ttagtaacaa ggaagaaaac acggagagac acacagtgga agatgtcaat     180
agagacatgc actctctcct gggtatgcgc aactga                               216
```

<210> SEQ ID NO 121
<211> LENGTH: 216
<212> TYPE: DNA
<213> ORGANISM: Mexico-Tabasco-42-PRSV

<400> SEQUENCE: 121

```
gctagatacg ctttcgattt ctatgaggtt aattcgaaaa cacctgatag ggctcgcgaa      60
gctcacatgc agatgaaagc tgcagcgctg cgaaacacta gtcgcagaat gtttggtatg     120
gacggcagtg ttagtaacaa ggaagaaaac acggagagac acacagtgga agatgtcaat     180
agagacatgc actctctcct gggtatgcgc aactga                               216
```

<210> SEQ ID NO 122
<211> LENGTH: 216

```
<212> TYPE: DNA
<213> ORGANISM: Mexico-Tabasco-43-PRSV

<400> SEQUENCE: 122
gctagatacg ctttcgatt

```
<211> LENGTH: 216
<212> TYPE: DNA
<213> ORGANISM: Mexico-Veracruz-VrCa15-PRSV

<400> SEQUENCE: 127
gctagatacg ctttcgattt ctatgaggtt aattcgaaaa cacctgatag ggctcgcgaa      60
gctcacatgc agatgaaagc tgcagcgctg cgaaacacta gtcgcagatt gtttggtatg     120
gacggcagtg ttagtaacaa ggaagaaaac acggagagac acacagtgga agatgtcaat     180
agagacatgc actctctcct gggtatgcgc aactga                               216

<210> SEQ ID NO 128
<211> LENGTH: 216
<212> TYPE: DNA
<213> ORGANISM: Mexico-Veracruz-VrCo-7-PRSV

<400> SEQUENCE: 128
gctagatacg ctttcgattt ctatgaggtt aattcgaaaa cacctgatag ggctcgcgaa      60
gctcacatgc agatgaaagc tgcagcgctg cgaaacacta gtcgcagaat gtttggtatg     120
gacggcagtg ttagtaacaa ggaagaaaac acggaaagac acacagtgga agatgtcaat     180
agagacatgc actctctcct gggtatgcgc aactga                               216

<210> SEQ ID NO 129
<211> LENGTH: 216
<212> TYPE: DNA
<213> ORGANISM: Mexico-Veracruz-VrGZ18-PRSV

<400> SEQUENCE: 129
gctagatacg ctttcgattt ctatgaggtg aattcgaaaa cacctgatag ggctcgcgaa      60
gctcacatgc agatgaaagc tgcagcgctg cgaaacacta gtcgcagaat gtttggtatg     120
gacggcagtg ttagtaacga ggaagaaaac acggagagac acacagtgga agatgtcaat     180
agagacatgc actctctcct gggtatgcgt aactga                               216

<210> SEQ ID NO 130
<211> LENGTH: 216
<212> TYPE: DNA
<213> ORGANISM: Mexico-VeracruzVP28-PRSV

<400> SEQUENCE: 130
gctaggtacg ctttcgattt ctatgaggtt aattcgaaaa cacctgatag ggctcgcgaa      60
gctcacatgc agatgaaagc tgcagcgctg cgaaacacta gtcgcagaat gtttggtatg     120
ggcggcagtg ttagtaacaa ggaagaaaac acggaaagac acacagtgga agatgtcaat     180
agagacatgc actctctcct gggtatgcgc aactaa                               216

<210> SEQ ID NO 131
<211> LENGTH: 216
<212> TYPE: DNA
<213> ORGANISM: Mexico-VeracruzVTB-6-PRSV

<400> SEQUENCE: 131
gctagatacg ctttcgattt ctatgaggtt aattcgaaaa cacctgatag ggctcgcgaa      60
gctcacatgc agatgaaagc tgcagcgctg cgaaacacta gtcgcagaat gtttggtatg     120
gacggcagtg ttagtaataa ggaagaaaac acggagagac acacagtgga agatgtcaat     180
agagacatgc actctctcct gggtatgcgc aactga                               216
```

-continued

<210> SEQ ID NO 132
<211> LENGTH: 216
<212> TYPE: DNA
<213> ORGANISM: Mexico-Yucatan-15-PRSV

<400> SEQUENCE: 132

```
gctagatatg ctttcgattt ctatgaggtg aattcgaaaa cacctgatag ggctcgcgaa      60
gcacacatgc agatgaaagc tgcagcgctg cgaaacacta atcgcagaat gtttggtatg     120
gacggcagtg ttagtaacaa ggaagaaaac acggagagac acacagtgga agatgtcaat     180
agagacatgc actctctcct gggtatgcgc aactga                               216
```

<210> SEQ ID NO 133
<211> LENGTH: 216
<212> TYPE: DNA
<213> ORGANISM: Philippines-PRSV

<400> SEQUENCE: 133

```
gccagatatg ctttcgattt ctatgaagtg aattcaaaaa cacctgctag agctcgtgaa      60
gctcatacgc agatgaaagc tgcagcactg tgtaacgctg gccgcagaat gtttggcatg     120
gacggctctg tcagcaacaa agaagaaaac acagaacgcc acacagtgga agacgtaaac     180
agagacatga catctcttct gggcatgcga aactga                               216
```

<210> SEQ ID NO 134
<211> LENGTH: 216
<212> TYPE: DNA
<213> ORGANISM: Puerto-Rico-PRSV

<400> SEQUENCE: 134

```
gctagatacg ctttcgattt ctatgaggtg aattcaaaaa cacctgatag ggcgcgcgaa      60
gctcacatgc agatgaaagc tgcagcgctg cgaaatacta gtcgcaggat gtttggtata     120
gacggcagtg ttagtaacaa ggaagaaaac acggagagac acacagtgga agatgtcaat     180
agagacatgc actctctcct gggtatgcgc aactga                               216
```

<210> SEQ ID NO 135
<211> LENGTH: 216
<212> TYPE: DNA
<213> ORGANISM: SriLanka-PRSV

<400> SEQUENCE: 135

```
gctagatatg ctttcgactt ctatgaggtg aattcgaaaa cacccgatag agctcgtgaa      60
gctcacatgc agatgaaagc tgcagcactg cggagcacta accgtaggat gtttggtatg     120
gacggcagtg tcagtaacaa ggaagaaaac acggagagac acacagtgga agatgtcaat     180
agagacatgc actctctcct gggtatgcgc aactga                               216
```

<210> SEQ ID NO 136
<211> LENGTH: 216
<212> TYPE: DNA
<213> ORGANISM: Taiwan-YK-PRSV

<400> SEQUENCE: 136

```
gctagatacg ctttcgactt ctatgaggtg aattcgaaaa cacctgatag ggctcgcgaa      60
gcccacatgc agatgaaggc tgcagcactg cgaaacacta gtcgcagaat gtttggtatg     120
gacggcagtg ttagtaacaa ggaagaaaac acggagagac acacagtgga agacgtcaat     180
agagacatgc actctctcct gggtatgcgc aactaa                               216
```

<210> SEQ ID NO 137
<211> LENGTH: 216
<212> TYPE: DNA
<213> ORGANISM: Taiwan-Maoka-PRSV

<400> SEQUENCE: 137

| | | |
|---|---|---|
| gctagatatg ctttcgattt ctatgaggta aattcgaaaa cacctgatag ggctcgtgaa | 60 |
| gctcatatgc agatgaaggc tgcagcgcta cgcaatacta atcgcagaat gtttggaatg | 120 |
| gacggcagtg tcagtaacaa ggaagaaaac acggagagac acacagtgga agatgtcaac | 180 |
| agagacatgc actctctcct gggtatgcgc aattga | 216 |

<210> SEQ ID NO 138
<211> LENGTH: 216
<212> TYPE: DNA
<213> ORGANISM: Thailand(Geneva)-Sarindu-PRSV

<400> SEQUENCE: 138

| | | |
|---|---|---|
| gctagatatg ctttcgactt ctatgaggtg aactcaaaaa cacctgatag ggctcgtgaa | 60 |
| gctcatatgc agatgaaggc tgcagcgctg cgcaacactg atcgcagaat gtttggaatg | 120 |
| gacggcagtg tcagtaacaa ggaagaaaac acggagagac acacagtgga agatgtcaac | 180 |
| agagacatgc actctctcct aggtatgcgc aattga | 216 |

<210> SEQ ID NO 139
<211> LENGTH: 216
<212> TYPE: DNA
<213> ORGANISM: Thailand-Bangkok-PRSV

<400> SEQUENCE: 139

| | | |
|---|---|---|
| gctagatatg ctttcgactt ctatgaggtg aactcaaaaa cacctgatag ggctcgtgaa | 60 |
| gctcatatgc agatgaaggc tgcagcgctg cgaaacactg gtcgcagaat gtttggaatg | 120 |
| gacggcagtg tcagtaacaa ggaagaaaac acggagagac acacagtgga agatgtcaac | 180 |
| agagacatgc actctctcct gggtatgcgt aattga | 216 |

<210> SEQ ID NO 140
<211> LENGTH: 216
<212> TYPE: DNA
<213> ORGANISM: Thailand-Chonburi1-PRSV

<400> SEQUENCE: 140

| | | |
|---|---|---|
| gctagatatg ctttcgactt ctatgaggtg agctcaaaaa cacctgatag ggctcgtgaa | 60 |
| gctcatatgc agatgaaggc tgcagcgctg cgcaacactg gtcgcagaat gtttggaatg | 120 |
| gatggcagtg tcagtaacaa ggaagaaaac acggagagac acacagtgga agatgtcaac | 180 |
| agagacatgc actctctcct gggtatgcgc aattga | 216 |

<210> SEQ ID NO 141
<211> LENGTH: 216
<212> TYPE: DNA
<213> ORGANISM: Thailand-Chonburi2-PRSV

<400> SEQUENCE: 141

| | | |
|---|---|---|
| gctagatatg ctttcgactt ctatgaggtg aactcaaaaa cacctgatag ggctcgtgaa | 60 |
| gctcatatgc agatgaaggc tgcagcgctg cgcaacactg gtcgcagaat gtttggaatg | 120 |
| gatggcagtg tcagtaacaa ggaagaaaac acggagagac acacagtgga agatgtcaac | 180 |
| agagacatgc actctctcct gggtatgcgc aattga | 216 |

<210> SEQ ID NO 142
<211> LENGTH: 216
<212> TYPE: DNA
<213> ORGANISM: Thailand-Chumporn-PRSV

<400> SEQUENCE: 142

| | | | |
|---|---|---|---|
| gctagatatg ctttcgactt ctatgaggtg aactcaaaaa cacctgatag ggctcgtgaa | 60 |
| gctcatatgc agatgaaggc tgcagcgctg cgcaacactg gtcgcagaat gtttggaatg | 120 |
| gacggcagtg tcagtaacaa ggaagaaaac acggagagac acacagtgga agatgtcaac | 180 |
| agagacatgc actctctcct aggtatgcgc aattga | 216 |

<210> SEQ ID NO 143
<211> LENGTH: 216
<212> TYPE: DNA
<213> ORGANISM: Thailand-KnonKhen-PRSV

<400> SEQUENCE: 143

| | | | |
|---|---|---|---|
| gctagatatg ctttcgactt ctatgaggtg aactcaaaaa cacctgatag ggctcgtgaa | 60 |
| gctcatatgc agatgaaggc tgcagcgctg cgcaacactg gtcgcagaat gtttggaatg | 120 |
| gacggcagtg tcagtaacaa ggaagaaaac acggagagac acacagtgga agatgtcaac | 180 |
| agagacatgc actctctcct aggtatgcgc aattga | 216 |

<210> SEQ ID NO 144
<211> LENGTH: 216
<212> TYPE: DNA
<213> ORGANISM: Thailand-KPS-PRSV

<400> SEQUENCE: 144

| | | | |
|---|---|---|---|
| gctagatatg ctttcgattt ctatgaggtg aattcaaaaa cacctgatag ggctcgtgaa | 60 |
| gctcatatgc agatgaaggc tgcagcgctg cgcaacacta gtcgcagaat gtttggaatg | 120 |
| gacggcagtg tcagtaacaa ggaagaaaac acggagagac acacagtgga agatgtcaat | 180 |
| agagacatgc actctctcct gggtatgcgc aattga | 216 |

<210> SEQ ID NO 145
<211> LENGTH: 216
<212> TYPE: DNA
<213> ORGANISM: Thailand-LabMild-PRSV

<400> SEQUENCE: 145

| | | | |
|---|---|---|---|
| gctagatacg ctttcgattt ctatgaggtc aattcaaaaa cgcctgatag agctcgtgaa | 60 |
| gctcatatgc agatgaaagc tgcagcgctg cgcaatgcta gtcgcagaat gtttggaatg | 120 |
| gacggcagtg tcagtaacaa ggaagaaaac acggagagac acacagtgga agatgtcaac | 180 |
| agagacatgc actctctcct gggtatgcgc aattga | 216 |

<210> SEQ ID NO 146
<211> LENGTH: 216
<212> TYPE: DNA
<213> ORGANISM: Thailand-LabSevere-PRSV

<400> SEQUENCE: 146

| | | | |
|---|---|---|---|
| gctagatacg ctttcgattt ctatgaggtc gattcaaaaa cgcctgatag agctcgtgaa | 60 |
| gctcatatgc agatgaaagc tgcagcgctg cgcaatgcta gtcgcagaat gtttggaatg | 120 |
| gacggcagtg tcagtaacaa ggaagaaaac acggagagac acacagtgga agatgtcaac | 180 |

```
agagacatgc actctctcct gggtatgcgc aattga                                  216
```

<210> SEQ ID NO 147
<211> LENGTH: 216
<212> TYPE: DNA
<213> ORGANISM: Thailand-Maoka-PRSV

<400> SEQUENCE: 147

```
gctagatatg ctttcgactt ctatgaggtg aactcaaaaa cacctgatag agctcgtgaa    60
gctcatatgc agatgaaggc tgcagcgctg cgcaacactg gtcgcagaat gtttgggatg   120
gacggcagtg tcagtaacaa ggaagaaaac acggagagac acacagtgga agatgtcaac   180
agagacatgc actctctcct gggtatgcgc aattga                             216
```

<210> SEQ ID NO 148
<211> LENGTH: 216
<212> TYPE: DNA
<213> ORGANISM: Thailand-PRSV

<400> SEQUENCE: 148

```
gctagatatg ctttcgactt ctatgaggtg aattcaaaaa cacctgatag ggctcgtgaa    60
gctcatacgc agatgaaggc tgcagcgctg cgcaacacta gtcgcagaat gtttggaatg   120
gacggcagtg tcagtaacaa ggaagaaaac acggagagac acacagtgga agatgtcaac   180
agagacatgc actctctcct gggtatgcgc aattga                             216
```

<210> SEQ ID NO 149
<211> LENGTH: 216
<212> TYPE: DNA
<213> ORGANISM: Venezuela-El-Vigia(Geneva)-PRSV

<400> SEQUENCE: 149

```
gctcgatacg cttttgattt ctatgaggtg aattcgaaaa cmcctgatag ggctcgtgaa    60
gctcacatgc agatgaaggc tgcagctttg cgaaacacta atcgcagaat gtttggtatc   120
gacggcagtg ttagcaacaa ggaagaaaac acggagagac acacagtgga tgatgtcaat   180
agagacatgc actctctcct gggtatgcgc aactaa                             216
```

<210> SEQ ID NO 150
<211> LENGTH: 216
<212> TYPE: DNA
<213> ORGANISM: Artificial Sequence
<220> FEATURE:
<223> OTHER INFORMATION: Description of Artificial Sequence: Consensus
      Sequence for Synthetic Australia-Hawaii (Pacific)
      PRSV-CP

<400> SEQUENCE: 150

```
gctagatacg ctttcgattt ctatgaggtg aattcgaaaa cacctgatag ggctcgcgaa    60
gctcacatgc agatgaaagc tgcagcgctg cgaaacacta gtcgcagaat gtttggtatg   120
gacggcagtg ttagtaacaa ggaagaaaac acggagagac acacagtgga agatgtcaat   180
agagacatgc actctctcct gggtatgcgc aactga                             216
```

<210> SEQ ID NO 151
<211> LENGTH: 216
<212> TYPE: DNA
<213> ORGANISM: Artificial Sequence
<220> FEATURE:
<223> OTHER INFORMATION: Description of Artificial Sequence:
      Australia-Hawaii(Pacific) PRSV-CP Synthetic
      Sequence

<400> SEQUENCE: 151
gctagatatg ctttcgattt ttatgaggtg aattcgaaaa cacctgatag ggctcgcgaa    60
gctcacatgc agatgaaagc tgcagcgctg cgaaacacta gtcgcagaat gtttggtatg   120
gacggcagtg ttagtaacaa ggaagaaaac acggagagac acacagtgga agatgtcaat   180
agagacatgc actctctcct gggtatgcgc aactaa                             216

<210> SEQ ID NO 152
<211> LENGTH: 216
<212> TYPE: DNA
<213> ORGANISM: Artificial Sequence
<220> FEATURE:
<223> OTHER INFORMATION: Description of Artificial Sequence:  Consensus
      Sequence for Americas Synthetic PRSV-CP

<400> SEQUENCE: 152
gctagatacg ctttcgattt ctatgaggtg aattcgaaaa cacctgatag ggctcgcgaa    60
gctcacatgc agatgaaagc tgcagcgctg cgaaacacta gtcgcagaat gtttggtatg   120
gacggcagtg ttagtaacaa ggaagaaaac acggagagac acacagtgga agatgtcaat   180
agagacatgc actctctcct gggtatgcgc aactga                             216

<210> SEQ ID NO 153
<211> LENGTH: 216
<212> TYPE: DNA
<213> ORGANISM: Artificial Sequence
<220> FEATURE:
<223> OTHER INFORMATION: Description of Artificial Sequence:  Americas
      PRSV-CP Synthetic Sequence

<400> SEQUENCE: 153
gccagatacg cttttgattt ctatgaggtg aattcaaaaa cacctgatag agctcgtgaa    60
gctcacatgc agatgaaggc tgcagcgctg cgaaacacta atcgtagaat gtttggtatg   120
gacggcagtg ttagcaacaa tgaagaaaac acggagagac acacagtgga agatgtcaat   180
agagacatgc actctctcct gggtatgcgc aactaa                             216

<210> SEQ ID NO 154
<211> LENGTH: 216
<212> TYPE: DNA
<213> ORGANISM: Artificial Sequence
<220> FEATURE:
<223> OTHER INFORMATION: Description of Artificial Sequence:  Asian
      PRSV-CP Synthetic Sequence

<400> SEQUENCE: 154
gccagatatg ctttcgattt ctatgaagtg aattcaaaaa cacctgatag agctcgtgaa    60
gctcacatgc agatgaaagc tgcagcactg cgtaacgcta atcgcagaat gtttggaatg   120
gacggcactg tcagtaacaa agaagaaaac acagaaagac acacagtgga agatgtaaac   180
agagacatgc aatctctcct gggtatgcgc aactga                             216

<210> SEQ ID NO 155
<211> LENGTH: 216
<212> TYPE: DNA
<213> ORGANISM: Artificial Sequence
<220> FEATURE:
<223> OTHER INFORMATION: Description of Artificial Sequence:  Consensus
      Sequence for Synthetic Asian PRSV-CP

<400> SEQUENCE: 155

-continued

```
gctagatatg ctttcgactt ctatgaggtg aattcaaaaa cacctgatag ggctcgtgaa      60
gctcatatgc agatgaaggc tgcagcgctg cgcaacacta gtcgcagaat gtttggaatg     120
gacggcagtg tcagtaacaa ggaagaaaac acggagagac acacagtgga agatgtcaac     180
agagacatgc actctctcct gggtatgcgc aattga                               216
```

```

<210> SEQ ID NO 156
<211> LENGTH: 216
<212> TYPE: DNA
<213> ORGANISM: Artificial Sequence
<220> FEATURE:
<223> OTHER INFORMATION: Description of Artificial Sequence:  Universal
      PRSV-CP Synthetic Sequence

<400> SEQUENCE: 156
gccagatacg ctttcgattt ctatgaggtg aattcaaaaa cacctgatag agctcgtgaa      60
gctcacacgc agatgaaagc tgcagcactg cgtaacacta atcgcagaat gtttggaatg     120
gacggcagtg tcagtaacaa agaagaaaac acagaaagac acacagtgga agatgtaaac     180
agagacatgc actctctcct gggtatgcgc aactga                               216
```

```
<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence:  PRSV-CP
      Homologous Starting Sequence

<400> SEQUENCE: 157
atagcgtagc tagctcgaga                                                   20
```

```
<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence:  PRSV-CP
      Homologous Starting Sequence

<400> SEQUENCE: 158
ctggcgtatc taggtcgaga                                                   20
```

```
<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence:  PRSV-CP
      Homologous Starting Sequence

<400> SEQUENCE: 159
atagcgtaac tagctcgaga                                                   20
```

```
<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence:  PRSV-CP
      Homologous Starting Sequence

<400> SEQUENCE: 160
atggcgtagc taggtcgaga                                                   20
```

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: PRSV-CP
      Homologous Consensus Sequence

<400> SEQUENCE: 161
atggcgtagc taggtcgaga 20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: PRSV-CP Synthetic Starting Sequence

<400> SEQUENCE: 162
atggcgtatc tagctcgaga 20

<210> SEQ ID NO 163
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 163
atcattctcg aggcaaagtc tgtgaggc 28

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 164
ttgccataat gctgggaggt agcttacctc ttattgcttc 40

<210> SEQ ID NO 165
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 165
agttgatagc tttgagatga tcagtgttgt cttggctata 40

<210> SEQ ID NO 166
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 166
tatcaggatg caaaatacaa ggatctcggg atcgacccaa 40

<210> SEQ ID NO 167
<211> LENGTH: 40
<212> TYPE: DNA
<213> ORGANISM: Artificial Sequence

```
<220> FEATURE:
<223> OTHER INFORMATION: Description of Artificial Sequence: Primer

<400> SEQUENCE: 167
agaagtatga caccagggaa gccttaggaa aagtttgcac                    40

<210> SEQ ID NO 168
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 168
tgtgctgaaa agaaaagcat ttgaaatgaa tgaagatcag                    40

<210> SEQ ID NO 169
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 169
agctaaggat ccctgatctt cattcatttc aa                            32

<210> SEQ ID NO 170
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 170
atgcttttct tttcagcaca gtgcaaactt ttcctaaggc                    40

<210> SEQ ID NO 171
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 171
ttccctggtg tcatacttct ttgggtcgat cccgagatcc                    40

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 172
ttgtattttg catcctgata tatagccaag acaacactga                    40

<210> SEQ ID NO 173
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 173
tcatctcaaa gctatcaact gaagcaataa gaggtaagct                    40
```

<210> SEQ ID NO 174
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 174
acctcccagc attatggcaa gcctcacaga ctttgcctcg                           40

<210> SEQ ID NO 175
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 175
ttcccataat gctgggaggt atcttacctc ttattgcttc                           40

<210> SEQ ID NO 176
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 176
tgttgatagc tttgagatgt tcagtgttgt cttggctaaa                           40

<210> SEQ ID NO 177
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 177
tatcaggatg caaatagaa ggatctcggg atcgacgcaa                            40

<210> SEQ ID NO 178
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 178
agaagtatga caccacggaa gccttaggaa aagtatgcac                           40

<210> SEQ ID NO 179
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 179
tgtgctgaaa agataagcat ttgaaatgaa tgtagatcag                           40

<210> SEQ ID NO 180
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 180
agctaaggat ccctgatcta cattcatttc aa                                  32

<210> SEQ ID NO 181
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 181
atgcttatct tttcagcaca gtgcatactt ttcctaaggc                          40

<210> SEQ ID NO 182
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 182
ttccgtggtg tcatacttct ttgcgtcgat cccgagatcc                          40

<210> SEQ ID NO 183
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 183
ttctattttg catcctgata tttagccaag acaacactga                          40

<210> SEQ ID NO 184
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 184
acatctcaaa gctatcaaca gaagcaataa gaggtaagat                          40

<210> SEQ ID NO 185
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 185
acctcccagc attatgggaa gcctcacaga ctttgcctcg                          40

<210> SEQ ID NO 186
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 186
atcattctcg agcgtttcag acagaggc                                       28

<210> SEQ ID NO 187

<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 187
acctcccagc attatggcaa gcctctgtct gaaacgctcg    40

<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 188
tgtgctgaaa agaaaagcat ttgaaatgat acttctagtc    40

<210> SEQ ID NO 189
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 189
agctaaggat ccgactagaa gtatcatttc aa    32

<210> SEQ ID NO 190
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 190
atagtcctac gaaaatacaa ggatctcggg atcgacccaa    40

<210> SEQ ID NO 191
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 191
ttgtattttc gtaggactat tatagccaag acaacactga    40

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 192
atcattctcg agcgtttcag acactccg    28

<210> SEQ ID NO 193
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 193
aacataaaac gtaggactat tatagccaag acaacactga                           40

<210> SEQ ID NO 194
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 194
agctaaggat ccgactagaa gtaagtaaag tt                                  32

<210> SEQ ID NO 195
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 195
atcattctcg agccaaagac tgtgacgc                                       28

<210> SEQ ID NO 196
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 196
ttgcgataat ggtgggagct agctttcctc tttttgcttg                          40

<210> SEQ ID NO 197
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 197
agttgacagc tttcagatga acagtgtagt cttgcctata                          40

<210> SEQ ID NO 198
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 198
tttcaggaag caaaaaacaa ggttctcggc atcgacgcaa                          40

<210> SEQ ID NO 199
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 199
agatgtatga gaccaggcaa gcctaaggaa atgtttgctc                          40

<210> SEQ ID NO 200
<211> LENGTH: 40
<212> TYPE: DNA

```
<213> ORGANISM: Artificial Sequence
<220> FEATURE:
<223> OTHER INFORMATION: Description of Artificial Sequence: Primer

<400> SEQUENCE: 200
tgtgctcaaa agataagcat atgaaatcaa tgaacatcac                           40

<210> SEQ ID NO 201
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 201
agctaaggat ccgtgatgtt cattgatttc at                                  32

<210> SEQ ID NO 202
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 202
atgcttatct tttgagcaca gagcaaacat ttccttaggc                           40

<210> SEQ ID NO 203
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 203
ttgcctggtc tcatacatct ttgcgtcgat gccgagaacc                           40

<210> SEQ ID NO 204
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 204
ttgttttttg cttcctgaaa tataggcaag actacactgt                           40

<210> SEQ ID NO 205
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 205
tcatctgaaa gctgtcaact caagcaaaaa gaggaaagct                           40

<210> SEQ ID NO 206
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 206
agctcccacc attatcgcaa gcgtcacagt ctttggctcg                           40
```

<210> SEQ ID NO 207
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 207
acctgggtcg taataccgtt cggagtgtct gaaacgctcg                     40

<210> SEQ ID NO 208
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 208
tgtgctgatt tcttttcgta aactttactt acttctagtc                     40

<210> SEQ ID NO 209
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 209
tacgaaaaga aatcagcaca gtgcaaactt ttcctaaggc                     40

<210> SEQ ID NO 210
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 210
atagtcctac gttttatgtt cctagagccc tacgacccaa                     40

<210> SEQ ID NO 211
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 211
ttccctggtg tcatacttct ttgggtcgta gggctctagg                     40

<210> SEQ ID NO 212
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 212
atcattctcg aggcaatgtc tctgagcc                                  28

<210> SEQ ID NO 213
<211> LENGTH: 40
<212> TYPE: DNA
<213> ORGANISM: Artificial Sequence
<220> FEATURE:

<223> OTHER INFORMATION: Description of Artificial Sequence: Primer

<400> SEQUENCE: 213
ttggcatatt gctcggagct agcataccac ttaatgctac                               40

<210> SEQ ID NO 214
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 214
agtagatacc tttcagatca tcactgttct cttcgctaaa                               40

<210> SEQ ID NO 215
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 215
tatgaggaag caatatacta ggaactcgcg atccaccta                                40

<210> SEQ ID NO 216
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 216
agatgtatca cacgagggta gccataggta aagattgctc                               40

<210> SEQ ID NO 217
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 217
tgtcctgata agataagctt ttgtaatgta tgatgatctg                               40

<210> SEQ ID NO 218
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 218
agctaaggat cccagatcat catacattac aa                                       32

<210> SEQ ID NO 219
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 219
aagcttatct tatcaggaca gagcaatctt tacctatggc                               40

<210> SEQ ID NO 220
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 220
taccctcgtg tgatacatct tagggtggat cgcgagttcc                40

<210> SEQ ID NO 221
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 221
tagtatattg cttcctcata tttagcgaag agaacagtga                40

<210> SEQ ID NO 222
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 222
tgatctgaaa ggtatctact gtagcattaa gtggtatgct                40

<210> SEQ ID NO 223
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 223
agctccgagc aatatgccaa ggctcagaga cattgcctcg                40

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 224
atcattctcg aggcaaaatc tgtgagac                             28

<210> SEQ ID NO 225
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 225
ttgccataat gctgggaggt agtatccctc ttattgcttc                40

<210> SEQ ID NO 226
<211> LENGTH: 40
<212> TYPE: DNA
<213> ORGANISM: Artificial Sequence
<220> FEATURE:
<223> OTHER INFORMATION: Description of Artificial Sequence: Primer

```
<400> SEQUENCE: 226
tgttgacagc tttgaaatga tcagtgttgt ccttgctata                    40

<210> SEQ ID NO 227
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 227
tatcaagatg caaaatacaa ggatctcggg attgaaccaa                    40

<210> SEQ ID NO 228
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 228
cgaagtataa cactaaggaa gccttaggaa aagtttgcac                    40

<210> SEQ ID NO 229
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 229
tgtgctgaaa agcaaaggat ttacaatgga tgaagatcag                    40

<210> SEQ ID NO 230
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 230
agctaaggat ccctgatctt catccattgt aa                            32

<210> SEQ ID NO 231
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 231
atcctttgct tttcagcaca gtgcaaactt ttcctaaggc                    40

<210> SEQ ID NO 232
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 232
ttccttagtg ttatacttcg ttggttcaat cccgagatcc                    40

<210> SEQ ID NO 233
<211> LENGTH: 40
```

```
<212> TYPE: DNA
<213> ORGANISM: Artificial Sequence
<220> FEATURE:
<223> OTHER INFORMATION: Description of Artificial Sequence:  Primer

<400> SEQUENCE: 233
ttgtattttg catcttgata tatagcaagg acaacactga                              40

<210> SEQ ID NO 234
<211> LENGTH: 40
<212> TYPE: DNA
<213> ORGANISM: Artificial Sequence
<220> FEATURE:
<223> OTHER INFORMATION: Description of Artificial Sequence:  Primer

<400> SEQUENCE: 234
tcatttcaaa gctgtcaaca gaagcaataa gagggatact                              40

<210> SEQ ID NO 235
<211> LENGTH: 40
<212> TYPE: DNA
<213> ORGANISM: Artificial Sequence
<220> FEATURE:
<223> OTHER INFORMATION: Description of Artificial Sequence:  Primer

<400> SEQUENCE: 235
acctcccagc attatggcaa gtctcacaga ttttgcctcg                              40
```

SYNTHETIC NUCLEIC ACID MOLECULE FOR IMPARTING MULTIPLE TRAITS

This application claims the benefit of U.S. Provisional Patent Application Ser. No. 60/286,075, filed Apr. 24, 2001.

FIELD OF THE INVENTION

The present invention relates to DNA constructs containing a modified nucleic acid molecule capable of imparting multiple desired traits to a plant, as well as host cells, plant cells, transgenic plants, and transgenic plant seeds containing such DNA constructs. The present invention also relates to a method of preparing a modified nucleic acid molecule capable of imparting multiple traits to a plant, a method of determining whether multiple desired traits can be imparted to plants by a single modified DNA molecule, and a method for imparting traits to plants.

BACKGROUND OF THE INVENTION

Control of plant virus diseases took a major step forward when it was shown that the tobacco mosaic virus ("TMV") coat protein ("CP") gene that was expressed in transgenic tobacco conferred resistance to TMV (Powell-Abel et al., "Delay of Disease Development in Transgenic Plants that Express the Tobacco Mosaic Virus Coat Protein Gene," Science 232:738–43 (1986)). The concept of pathogen-derived resistance ("PDR"), which states that pathogen genes that are expressed in transgenic plants will confer resistance to infection by the homologous or related pathogens (Sanford et al., "The Concept of Parasite-Derived Resistance—Deriving Resistance Genes from the Parasite's Own Genome," J. Theor. Biol., 113:395–405 (1985)) was introduced at about the same time. Since then, numerous reports have confirmed that PDR is a useful strategy for developing transgenic plants that are resistant to many different viruses (Lomonossoff, G. P., "Pathogen-Derived Resistance to Plant Viruses," Ann. Rev. Phytopathol., 33:323–43 (1995)).

Remarkable progress has been made in developing virus resistant transgenic plants despite a poor understanding of the mechanisms involved in the various forms of pathogen-derived resistance (Lomonossoff, G. P., "Pathogen-Derived Resistance to Plant Viruses," Ann. Rev. Phytopathol. 33:323–43 (1995)). Although most reports deal with the use of coat protein genes to confer resistance, a growing number of reports have shown that viral replicase (Golemboski et al., "Plants Transformed with a Tobacco Mosaic Virus Non-structural Gene Sequence are Resistant to the Virus," Proc. Natl. Acad. Sci. USA 87:6311–15 (1990)), movement protein (Beck et al., "Disruption of Virus Movement Confers Broad-Spectrum Resistance Against Systemic Infection by Plant Viruses with a Triple Gene Block," Proc. Natl. Acad. Sci. USA, 91:10310–14 (1994)), NIa proteases of potyviruses (Maiti et al., "Plants that Express a Potyvirus Proteinase Gene are Resistant to Virus Infection," Proc. Natl. Acad. Sci. USA, 90:6110–14 (1993)), and other viral genes are effective. This led to the conclusion that any part of a plant viral genome may give rise to PDR. Furthermore, the viral genes can be effective in the translatable and nontranslatable sense forms, and less frequently, antisense forms (Baulcombe, "Mechanisms of Pathogen-Derived Resistance to Viruses in Transgenic Plants," Plant Cell 8:1833–44 (1996); Dougherty et al., "Transgenes and Gene Suppression: Telling us Something New?," Current Opinion in Cell Biology 7:399–05 (1995); Lomonossoff, G. P., "Pathogen-Derived Resistance to Plant Viruses," Ann. Rev. Phytopathol. 33:323–43 (1995)).

RNA-mediated resistance is the form of PDR where there is clear evidence that viral proteins do not play a role in conferring resistance to the transgenic plant. The first clear cases for RNA-mediated resistance were reported in 1992 for tobacco etch ("TEV") potyvirus (Lindbo et al., "Pathogen-Derived Resistance to a Potyvirus Immune and Resistance Phenotypes in Transgenic Tobacco Expressing Altered Forms of a Potyvirus Coat Protein Nucleotide Sequence," Mol. Plant Microbe Interact. 5:144–53 (1992)), potato virus Y ("PVY") potyvirus (Van Der Vlugt et al., "Evidence for Sense RNA-Mediated Protection to PVY in Tobacco Plants Transformed with the Viral Oat Protein Cistron," Plant Mol. Biol., 20:631–39 (1992), and for tomato spotted wilt ("TSWV") tospovirus (de Haan et al., "Characterization of RNA-Mediated Resistance to Tomato Spotted Wilt Virus in Transgenic Tobacco Plants," Bio/Technology 10:1133–37 (1992)).

Other workers confirmed the occurrence of RNA-mediated resistance with potyviruses (Smith et al., "Transgenic Plant Virus Resistance Mediated by Untranslatable Sense RNAs: Expression, Regulation, and Fate of Nonessential RNAs," Plant Cell 6:1441–53 (1994)), potexviruses ("PXV") (Mueller et al., "Homology-Dependent Resistance: Transgenic Virus Resistance in Plants Related to Homology-Dependent Gene Silencing," Plant Journal 7:1001–13 (1995)), and TSWV and other tospoviruses (Pang et al., "Resistance of Transgenic Nicotiana Benthamiana Plants to Tomato Spotted Wilt and Impatiens Necrotic Spot Tospoviruses: Evidence of Involvement of the N Protein and N Gene RNA in Resistance," Phytopathology 84:243–49 (1994); Pang et al., "Different Mechanisms Protect Transgenic Tobacco Against Tomato Spotted Wilt Virus and Impatiens Necrotic Spot Tospoviruses," Bio/Technology 11:819–24 (1993)). More recent work has shown that RNA-mediated resistance also occurs with the comovirus cowpea mosaic virus (Sijen et al., "RNA-Mediated Virus Resistance: Role of Repeated Transgene and Delineation of Targeted Regions," Plant Cell 8:2227–94 (1996)) and squash mosaic virus (Pang et al., "Resistance to Squash Mosaic Comovirus in Transgenic Squash Plants Expressing its Coat Protein Genes," Molecular Breeding 6:87–93 (2000)).

Major advances towards understanding the mechanism(s) of RNA-mediated resistance were made by Dougherty and colleagues in a series of experiments with TEV and PVY. Using TEV, this group showed that transgenic plants expressing translatable full length coat protein, truncated translatable coat protein, antisense coat protein genes, and nontranslatable coat protein genes had various phenotypic reactions after inoculation with TEV (Lindbo, J. A., "Pathogen-Derived Resistance to a Potyvirus Immune and Resistant Phenotypes in Transgenic Tobacco Expressing Altered Forms of a Potyvirus Coat Protein Nucleotide Sequence," Mol. Plant Microbe Interact. 5:144–53 (1992) and Lindbo et al., "Untranslatable Transcripts of the Tobacco Etch Virus Coat Protein Gene Sequence Can Interfere with Tobacco Etch Virus Replication in Transgenic Plants and Protoplasts," Virology 189:725–33 (1992)). Transgenic plants displayed resistance, recovery (inoculated plants initially show systemic infection but younger leaves that develop later are symptomless and resistant to the virus), or susceptible phenotypes. Furthermore, they showed that leaves of resistant plants and asymptomatic leaves of recovered plants had relatively low levels of steady state RNA when compared to those in leaves of susceptible plants (Lindbo et al., "Induction of a Highly Specific Antiviral State in Transgenic Plants: Implications for Regulation of Gene Expression and Virus Resistance," *Plant Cell* 5:1749–59 (1993)). However, nuclear run off experiments showed that those plants with low levels of steady state RNA had higher transcription rates of the viral transgene than those plants that were susceptible (and had high steady state RNA levels). To account for these observations, it was proposed "that the resistant state and reduced steady state levels of transgene transcript accumulation are mediated at the cellular level by a cytoplasmic activity that targets specific RNA sequences for inactivation" (Lindbo et al., "Induction of a Highly Specific Antiviral State in Transgenic Plants: Implications for Regulation of Gene Expression and Virus Resistance," *Plant Cell* 5:1749–59 (1993)). It was also suggested that the low steady state RNA levels may be due to post-transcriptional gene silencing ("PTGS"), causing a lack of expression of the transcribed gene, a phenomenon that was first proposed by de Carvalho et al., "Suppression of Beta-1,3-glucanase Transgene Expression in Homozygous Plants," *EMBO J.* 11:2595–602 (1992) for the suppression of β-1,3-glucanase transgene in homozygous transgenic plants.

An RNA threshold model was proposed to account for these observations (Lindbo et al., "Induction of a Highly Specific Antiviral State in Transgenic Plants: Implications for Regulation of Gene Expression and Virus Resistance," *Plant Cell,* 5:1749–59 (1993)). This model states that there is a cytoplasmic cellular degradation mechanism that acts to limit the RNA levels in plant cells, and that this mechanism is activated when the transgenic RNA transcript goes above a threshold level. The degradation mechanism is specific for the transcript that goes above the threshold level; and if the transcript that goes above a certain threshold is a viral transgene, the virus resistance state is observed in the plant, because the degradation mechanism also targets, for inactivation, the specific sequences of the incoming virus. The model also accounts for the 'recovery' of transgenic plants by suggesting that viral RNA from the systemically invading virus triggers the phenomenon in some transgenic plants that have two copies of the transgenes. Plants that had more than three copies of the transgenes caused the threshold level to be surpassed without the invasion of virus (Goodwin et al., "Genetic and Biochemical Dissection of Transgenic RNA-Mediated Virus Resistance," *Plant Cell* 8:95–105 (1996); Smith et al., "Transgenic Plant Virus Resistance Mediated by Untranslatable Sense RNAs: Expression, Regulation, and Fate of Nonessential RNAs," *Plant Cell* 6:1441–53 (1994)). Although the degradation mechanism is not clear, it is proposed that a cellular RNA dependent RNA polymerase ("RdRp") binds to the transcript and produces small fragments of antisense RNA which then bind to other transcripts to form duplexes which are then degraded by nucleases that specifically recognize RNA—RNA duplexes. This degradation mechanism is sequence specific, which accounts for the specificity of RNA-mediated resistance.

Work on PVX by Baulcombe and colleagues (English et al., "Suppression of Virus Accumulation in Transgenic Plants Exhibiting Silencing of Nuclear Genes," *Plant Cell* 8: 179–88 (1996); Mueller et al., "Homology-Dependent Resistance: Transgenic Virus Resistance in Plants Related to Homology-Dependent Gene Silencing," *Plant Journal* 7:1001–13 (1995)) confirmed and extended the results by Dougherty and colleagues. An aberrant RNA model which is a modification of the RNA threshold model of Dougherty was proposed. The features of the model are similar to the Dougherty model except that it states that the RNA level is not the sole trigger to activate the cellular degradation mechanism, but instead aberrant RNAs that are produced during the transcription of the transgene play an important part in activating the cytoplasmic cellular mechanism that degrades specific RNA. The production of aberrant RNA may be enhanced by positional affects of the transgene on the chromosome and by methylation of the transgene DNA. The precise nature of the aberrant RNA is not defined, but it may contain a characteristic that makes it a preferred template for the production of antisense RNA by the host encoded RdRp (Baulcombe, D. C., "Mechanisms of Pathogen-Derived Resistance to Viruses in Transgenic Plants," *Plant Cell* 8:1833–44 (1996); English et al., "Suppression of Virus Accumulation in Transgenic Plants Exhibiting Silencing of Nuclear Genes," *Plant Cell* 8: 179–88 (1996)). Thus, the model also proposes that RdRp and antisense molecules are involved in the degradation mechanism. Baulcombe and colleagues confirmed that plants which show low steady state transgene levels have multiple copies of transgenes and that the low steady state RNA and the accompanying resistant state is due to post-transcriptional gene silencing. The term homology-dependent resistance was proposed to describe the resistance in plants that show homology-dependent gene silencing (Mueller et al., "Homology-Dependent Resistance: Transgenic Virus Resistance in Plants Related to Homology-Dependent Gene Silencing," *Plant Journal* 7:1001–13 (1995)).

Numerous reports have been published on critical advances in the understanding of the biochemistry and genetics of both gene silencing and RNA-interference. Similarities between RNA-interference ("RNAi") and post-transcriptional gene silencing are astonishing, and point all to the crucial role played by sequence homology in triggering these two mechanistically related phenomena (Matzke et al., "RNA-Based Silencing Strategies in Plants," *Curr. Opin. Genet. Dev.* 11(2):221–227 (2001)). In RNAi, the introduction of double stranded RNA into animal or plant cells leads to the destruction of the endogenous, homologous mRNA, phenocopying a null mutant for that specific gene. In both post-transcriptional gene silencing and RNAi, the dsRNA is processed to short interfering molecules of 21-, 22- or 23-nucleotide RNAs ("siRNA") by a putative RNAaseIII-like enzyme (Tuschl T., "RNA Interference and Small Interfering RNAs," *Chembiochem* 2: 239–245 (2001); Zamore et al., "RNAi: Double Stranded RNA Directs the ATP-Dependent Cleavage of mRNA at 21 to 23 Nucleotide Intervals," *Cell* 101, 25–3, (2000)). The endogenously generated siRNAs mediate and direct the specific degradation of the target mRNA. In the case of RNAi the cleavage site in the mRNA molecule targeted for degradation is located near the center of the region covered by the siRNA (Elbashir et al., "RNA Interference is Mediated by 21- and 22-Nucleotide RNAs," *Gene Dev.* 15(2):188–200 (2001)).

Whether the same model applies for post-transcriptional gene silencing is still under debate (however, see Thomas et al., "Size Constraints for Targeting Post-Transcriptional Gene Silencing and for RNA-Directed Methylation in Nicotiana Benthamiana Using a Potato Virus X Vector," *Plant J.* 25(4):417–425 (2001)).

Tomato Spotted Wilt Virus ("TSWV") is a very damaging virus of worldwide distribution that attacks ornamentals and vegetable crops, causing multimillion-dollar losses annually. TSWV belongs to the Tospoviridae family (Bunyavirus group), has a tripartite genome composed of sense and antisense RNA, and is transmitted by thrips in a persistent manner. Tobacco plants have been engineered to express full or partial version of the nucleocapsid ("N") gene of TSWV-BL. It has been clearly demonstrated that any single fragment of the TSWV-BL N gene is able to confer resistance against the virus by post-transcriptional gene silencing (Pang et al., "Nontarget DNA Sequences Reduce the Transgene Length Necessary for RNA-Mediated Tospovirus Resistance in Transgenic Plants," *Proc. Natl. Acad. Sci. USA,* 94:8261–66 (1997)). Moreover, the fragments can be reduced to a minimum of 100 nt long and still trigger post-transcriptional gene silencing if transcriptionally fused to a non-related, carrier DNA (Pang et al., "Nontarget DNA Sequences Reduce the Transgene Length Necessary for RNA-Mediated Tospovirus Resistance in Transgenic Plants," *Proc. Natl. Acad. Sci. USA,* 94:8261–66 (1997) ("Pang 1997")). Furthermore, it has been shown that the use of short fragments allowed the incorporation of viral gene fragments from multiple viral sources, imparting resistance to the plant against a plurality of viral pathogens (Jan, Doctor in Philosophy Thesis Dissertation, "Roles of Non-Target DNA and Viral Gene Length in Influencing Multivirus Resistance Through Homology-Dependent Gene Silencing," Cornell University, p. 286 (1988)). These short fragments, which individually have insufficient length to impart such resistance, are more easily and cost effectively produced than full length genes. Furthermore, there is no need to include in the plant separate promoters for each of the fragments; only a single promoter is required.

Two important, and heretofore unanswered questions related to genetically engineered viral resistance using short viral DNA fragments are: 1) how do changes in sequence homology of the transgene affect its effectiveness in conferring resistance, and 2) can a synthetic DNA be produced with sufficient sequence homology such that the synthetic DNA would confer resistance against multiple viruses. While great strides have been made in PDR methodology, such as imparting resistance to multiple viral pathogens, even Pang's method involves time-consuming and expensive steps required to isolate and manipulate multiple viral DNAs for transformation purposes. What is needed now is a method for utilizing sequence homology information to design and create a single, short synthetic transgene that will impart multiple traits, thereby significantly reducing the labor and materials currently invested in cloning and subcloning procedures directed to imparting pathogen resistance and other traits.

The present invention is directed to overcoming these and other deficiencies in the art.

SUMMARY OF THE INVENTION

The present invention relates to a DNA construct containing a modified nucleic acid molecule with a nucleotide sequence which is at least 80%, but less than 100%, homologous to two or more desired trait DNA molecules. Each of the desired trait DNA molecules, relative to the modified nucleic acid molecule, have a nucleotide sequences similarity value and each of these similarity values differs by no more than 3 percentage points. The modified nucleic acid molecule imparts the desired trait to plants transformed with the DNA construct.

The present invention also relates to a DNA construct containing a plurality of modified nucleic acid molecules, at least some of which have a nucleotide sequence which is at least 80%, but less than 100%, homologous to one or more desired trait DNA molecules. This plurality of modified nucleic acid molecules collectively impart their plurality of traits to plants transformed with the DNA construct. At least some of the desired trait DNA molecules relative to their respective modified nucleic acid molecule have a nucleotide sequence similarity value and each of these similarity values differs by no more than 3 percentage points.

The present invention also relates to expression vectors, host cells, plant cells, transgenic plants, and transgenic plant seeds containing the DNA construct of the present invention. Methods of imparting one or more traits to plants with the DNA construct of the present invention are also disclosed.

The present invention also relates to a method of preparing a modified nucleic acid molecule suitable to impart multiple traits to a plant. This involves identifying a plurality of desired traits to be imparted to plants, where the desired traits are imparted by desired DNA molecules having nucleotide sequences. This method also involves selecting, as a reference nucleotide sequence, one nucleotide sequence from among the desired trait DNA molecules identified. The reference nucleic acid molecule is then modified to be at least 80%, but less than 100%, homologous to the nucleotide sequences of the desired DNA molecules identified. Each of the desired trait DNA molecules, relative to the modified nucleic acid molecule, have a nucleotide sequence similarity value and each of these similarity values differs by 3 percentage points or less.

The present invention also relates to a method of determining whether multiple desired traits can be imparted to plants by a single modified DNA molecule. This involves identifying a plurality of desired traits to be imparted to plants, where the desired traits are imparted by desired trait DNA molecules, having nucleotide sequences. One nucleotide sequence from among the desired trait DNA molecules identified is selected as a reference nucleotide sequence, and the reference nucleotide sequence is modified. A determination is then made whether the modified nucleic acid molecule is at least 80%, but less than 100%, homologous to the desired trait DNA molecules identified and whether each of the desired trait DNA molecules, relative to the modified nucleic acid molecule, have a nucleotide sequence similarity value and whether each of these similarity values differs by no more than 3 percentage points.

Post-transcriptional silencing influences traits (including viral resistance) in transgenic plants and its effect is sequence homology dependent. For example, a transgene will confer resistance to a virus if it has a homology of 80% or greater to that virus. Applicants have taken advantage of the sequence homology dependent characteristic of post-transcriptional silencing. Previously, it was shown that linking a trait DNA to a silencer DNA which triggers post-transcriptional silencing allows the use of trait DNA molecules that are shorter than required if the trait DNA was used alone. For example, a 200 bp segment of the N gene of TSWV does not confer resistance to transgenic plants when used alone as the transgene, but does confer resistance when linked to a silencer DNA such as a green fluorescent protein. Thus, transgenic plants were obtained with multiple traits by linking short DNA trait molecules to a silencer DNA. Two advantages of this previous finding are that a single transgene with only one promoter could impart multiple traits, and that the length of the trait DNA could be considerably shortened by linking them to a silencer DNA.

In accordance with the present invention, short synthetic DNAs can impart multiple traits by simply making the synthetic DNA so that it has sufficient sequence homology to the individual DNA molecules to impart the traits. For example, TSWV and groundnut ringspot virus ("GRSV") are two tosposviruses that share only 76% homology within their N gene. Applicants synthesized a 216 bp DNA that has 90% homology to both viruses and that DNA conferred resistance to both viruses when linked to the silencer DNA.

Compared to the previous finding: 1) this synthetic DNA was only 216 bp long (whereas, using the previous approach would need to link a 216 bp segment of TSWV to a 216 bp segment of GRSV to impart resistance to both viruses); 2) this synthetic DNA could easily be synthesized without using any DNA from the virus as a template for generating the trait DNA whereas the latter had to be done when the previous approach was used; 3) homology of the DNA to the trait DNA molecules could be obtained by simply designing a synthetic DNA that showed at least 80% homology to the target trait molecules; and 4) this invention could be applied to any trait that is affected by post-transcriptional silencing (and thus is sequence homology dependent). In short, synthetic genes that impart multiple traits can be custom designed by simply comparing nucleotide sequences of DNAs that confer separate traits and synthesizing a short DNA that has at least 80% homology to each of the target trait DNAs. The number of traits can be expanded by linking these synthetic DNA molecules.

BRIEF DESCRIPTION OF THE DRAWINGS

FIGS. 4A–B show PCR analysis of some resulting transgenic lines. FIG. 4A shows PCR analysis of the nptII gene; FIG. 4B shows PCR analysis of ¾ N gene. Genomic DNA was isolated from independent transgenic lines as indicated. The examples shown here correspond to some plants transformed with a gene with 5% changes scattered (5) or clustered at the 3' end (5-3'). As a control, seed-derived plants from lines FJ-5 and FJ-22 transformed with the native ⅔N gene were used, as well as non-transgenic *N. benthamiana* DNA (C⁻). An additional positive control (C⁺) was DNA from the corresponding 5%-modified synthetic gene fragment clones in pGA482G.

FIG. 6 shows a comparison of the ¾N gene of three different Tospoviruses: Tomato Spotted Wilt Virus ("TSWV") (SEQ ID NO: 1), Groundnut Ringspot Virus ("GRSV") (SEQ ID NO: 2), and Tomato Chlorotic Spot Virus ("TCSV") (SEQ ID NO: 3), and the Rec2 synthetic gene (SEQ ID NO: 4). Nucleotides that differ from Rec2 are shown in lower case.

FIG. 7 shows the starting sequences for the conserved regions of the coat protein (CP) gene of the TH (SEQ ID NO: 6), KE (SEQ ID NO: 7) and YK (SEQ ID NO: 8) sequences from papaya ringspot virus compared to each other and to the sequence of the modified synthetic nucleic acid (SEQ ID NO: 5) generated for targeting these PRSV isolates. The underlined portions identify segments of more than 20 nt long of perfect similarity. The nucleotide changes differing from the synthetic sequence are shown in lowercase.

FIG. 8 shows the distribution of dissimilar nucleotides compared to the synthetic gene (SEQ ID NO: 9) for the variable regions of the of the CP gene of TH (SEQ ID NO: 10), KE (SEQ ID NO: 11) and YK (SEQ ID NO: 12). The underlined portions identify segments of more than 20 nt long of perfect similarity. The nucleotide changes differing from the synthetic sequence are shown in lowercase.

FIG. 10 shows the CLUSTALW alignment of the nine selected potyvirus sequences and their consensus sequence from FIG. 9 after modification in comparison to the synthetic modified sequence (SEQ ID NO: 23).

FIG. 11 shows the CLUSTALW alignment of the five selected tomato polygalacturonase sequences (SEQ ID NO: 24–SEQ ID NO: 29) before modification.

FIG. 14 shows the CLUSTALW alignment of the of the six selected Petunia chalcone synthase ("CHS") and their consensus sequence from FIG. 13 after modification in comparison to the synthetic modified Petunia CHS sequence (SEQ ID NO: 38).

FIG. 17 shows the CLUSTALW alignment of the nineteen selected ACC-oxidase ("ACC") sequences from various plants and their consensus sequence (SEQ ID NO: 48–SEQ ID NO: 67) before modification.

FIG. 18 shows the CLUSTALW alignment of the nineteen selected ACC-oxidase ("ACC") sequences from various plants and their consensus sequence from FIG. 17 after modification in comparison to the synthetic modified ACC sequence (SEQ ID NO: 68).

FIG. 20 shows the CLUSTALW alignment of the resulting synthetic modified "Universal Americas" PRSV isolate sequence in comparison with the starting sequences, the consensus sequence, and synthetic gene sequence from FIG. 19.

FIG. 21 shows the CLUSTALW alignment of the resulting synthetic modified "Universal Asia" PRSV isolate sequence in comparison with the starting sequences, the consensus sequence, and synthetic gene sequence from FIG. 19.

FIG. 22 shows the CLUSTALW alignment of the resulting synthetic modified "Universal Pacific" PRSV isolate sequence in comparison with the starting sequences, the consensus sequence, and synthetic gene sequence from FIG. 19.

DETAILED DESCRIPTION OF THE INVENTION

Figure 1:
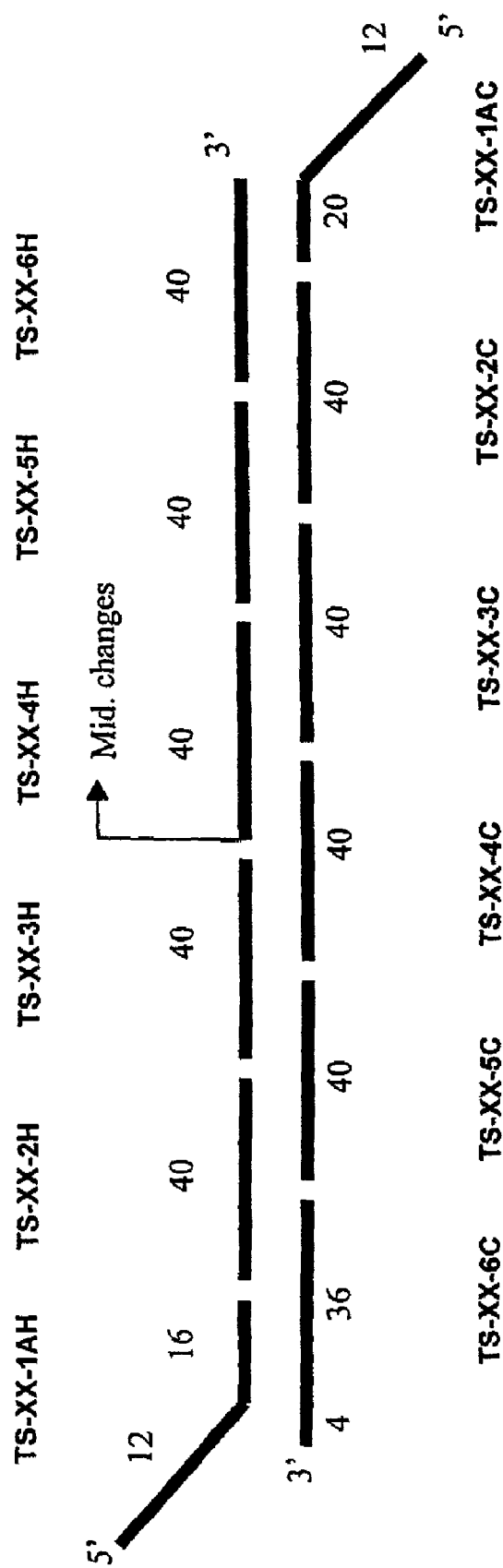
FIG. 1 shows the scheme of the 216 bp TSWV fragment and the corresponding primers to be named to be used for its synthesis. The diagonal lines indicate the place in the oligonucleotides ("oligos") where six random nucleotides and six nucleotides corresponding to restriction sites are located: XhoI for the 5' end (left) and BamHI for the 3' end (right). The XX in the middle of the oligo name refers to the percentage of change for every single construct according to Tables 3 and 4. The fragment is shown in the sense orientation.

The present invention relates to a DNA construct containing a modified nucleic acid molecule with a nucleotide sequence which is at least 80%, but less than 100%, homologous to two or more desired trait DNA molecules. Each of the desired trait DNA molecules relative to the modified nucleic acid molecule have a nucleotide sequence similarity value and each of these similarity values differs by no more than 3 percentage points. The modified nucleic acid molecule imparts the desired trait to plants transformed with the DNA construct.

In one aspect of the present invention, the construct also includes a silencer DNA molecule operatively coupled to the modified nucleic acid molecule. In this embodiment, the modified nucleic acid molecule and silencer DNA molecule collectively impart the desired trait to plants transformed with the DNA construct.

In another aspect of the present invention, the DNA construct can be a fusion gene (chimera) which includes a plurality of modified DNA molecules at least some of which have a nucleotide sequence that is at least 80%, but less than 100%, homologous to the two or more desired trait DNA molecules. The plurality of trait molecules may be directed to one or more desired traits, and collectively impart the plurality of traits to plants transformed with the DNA construct. At least some of the desired trait DNA molecules, relative to their respective modified nucleic acid molecule, have a nucleotide sequence similarity value and each of these similarity values differs by no more than 3 percentage points.

"Trait" as used herein refers to any characteristic genetically determined in a given organism, as well as any characteristic that may be imparted by transformation and regulated by post-transcriptional gene silencing. Therefore, the DNA molecules of the present invention may be endogenous (normally occurring), or exogenous (not normally occurring) in an organism.

The terms "homologous" and "homology" are used herein to mean a structural similarity between or among nucleic acid sequences, measured as percent of similarity of corresponding deoxyribonucleotide bases (a, t, c, g) in two or more nucleic acid sequences compared to one another by any method. For example, once desired trait sequences are identified, they may be used to perform a BLAST search for further homologous nucleic acids in the GenBank database, or any other gene database. For the design, virtual assembly, and alignment of all synthetic and native sequences, a computer program, such as DNAStar (LaserGene Software, Madison, Wis.), or the GeneDoc software ((Nicholas et al., "GeneDoc: A Tool For Editing and Annotating Multiple Sequence Alignments" Software Ver. 2.6.002 (1997), and similarity trees can be generated with the Tree View software (Page, Software version 1.6. (2001), and both of these programs are freely available on the web and are suitable and hereby incorporated by reference in their entirety).

Percent similarity and percent identity are values used interchangeably in the art as measures of nucleotide homology. For example, two sequences having perfect identity would have 100% similarity and, therefore, would be described as having perfect, or 100%, homology to one another.

One aspect of the present invention relates to the use of trait DNA molecules which are exogenous to the plant, for example, DNA molecules that confer disease resistance to plants transformed with the DNA construct. The present invention is useful in plants for imparting resistance to a wide variety of pathogens including viruses, bacteria, fungi, viroids, phytoplasmas, nematodes, and insects. Resistance, inter alia, to the following viruses can be achieved by the method of the present invention: tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, or combinations thereof. Resistance, inter alia, to the following bacteria can also be imparted to plants in accordance with present invention: *Pseudomonas solancearum*, *Pseudomonas syringae* pv. *tabaci*, *Xanthomonas campestris* pv. *pelargonii*, and *Agrobacterium* spp., including *Agrobacterium tumefaciens*. Plants can be made resistant, inter alia, to the following fungi by use of the method of the present invention: *Fusarium oxysporum* and *Phytophthora infestans*. Suitable DNA molecules include a DNA molecule encoding any gene of the viral genome, including a coat protein, a replicase, a DNA molecule not encoding protein, a DNA molecule encoding a viral gene product, or combinations thereof. Furthermore, the present invention may also be used to impart genetic traits in many organisms, including, but not limited to, bacteria, plants, and mammals.

The present invention is also used to confer traits other than disease resistance on plants. For example, DNA molecules which impart a genetic trait can be used as the desired trait molecule of the present invention. In this aspect of the present invention, suitable trait molecules encode for desired color, enzyme production (or cessation of production), plant hormones, or combinations thereof. Enzymes include those involved in fruit development, such as ripening, or in any developmental or metabolic pathway.

In one aspect of the present invention, the DNA construct of the present invention contains a plurality of modified trait DNA molecules operably linked together. In this embodiment, each single modified trait molecule is designed to impart a different collection of desired traits. For each set of desired traits, a plurality of trait DNA molecules are identified. From this plurality of trait DNA molecules, one is selected as a reference sequence. This reference sequence is used to design a modified nucleic acid which is ultimately at least 80% (but less than 100%) homologous to the trait DNA molecules. Each of these trait DNA molecules, relative to the final modified nucleic acid molecule has a nucleotide sequence similarity value and each of these similarity values differs by no more than 3 percentage points. This to render dsRNAs only in this cellular compartment. New vectors have been developed elsewhere that might facilitate this task (Wesley et al., "Construct Design For Efficient, Effective and High-Throughput Gene Silencing in Plants," *The Plant Journal* 27: 581–590 (2001), which is hereby incorporated by reference in its entirety).

The DNA constructs of the present invention also may be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference in its entirety), and any derivatives thereof, as well as those mentioned above for producing dsRNA in the cell. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, NY (1989), and Ausubel, F. M. et al. (1989) *Current Protocols in Molecular Biology*, John Wiley & Sons, New York, N.Y., which are hereby incorporated by reference in their entirety.

In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and, generally, one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803–4807 (1983), which is hereby incorporated by reference in its entirety).

Further improvement of this technique led to the development of the binary vector system (Bevan, M., "Binary Agrobacterium Vectors for Plant Transformation," *Nucleic Acids Res.* 12:8711–8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch, et al., "Complete Sequence of the Binary Vector Bin19," *Plant Molec. Biol.* 27:405–409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens* (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 issued to Shewmaker et al., which is hereby incorporated by reference in its entirety). In the preferred embodiment of the present invention, an exogenous promoter is linked to the nucleic acid of the construct, where "exogenous promoter" is defined as a promoter to which the nucleic acid of the construct is not linked in nature.

The nucleic acid construct of the present invention also includes an operable 3' regulatory region, selected from among those which are capable of providing correct transcription termination and polyadenylation of mRNA for expression in the host cell of choice, operably linked to a modified trait DNA molecule of the present invention. A number of 3' regulatory regions are known to be operable in plants. Exemplary 3' regulatory regions include, without limitation, the nopaline synthase ("nos") 3' regulatory region (Fraley, et al., "Expression of Bacterial Genes in Plant Cells," *Proc. Nat'l Acad. Sci. USA* 80:4803–4807 (1983), which is hereby incorporated by reference in its entirety) and the cauliflower mosaic virus ("CaMV") 3' regulatory region (Odell, et al., "Identification of DNA Sequences Required for Activity of the Cauliflower Mosaic Virus 35S Promoter," *Nature* 313(6005):810–812 (1985), which is hereby incorporated by reference in its entirety). Virtually any 3' regulatory region known to be operable in plants would suffice for proper expression of the coding sequence of the nucleic acid of the present invention.

The modified trait DNA molecule(s), a suitable promoter, silencing gene if included, and an appropriate 3' regulatory region can be ligated together to produce the expression systems which contain the DNA constructs of the present invention, using well known molecular cloning techniques as described in Sambrook et al., *Molecular Cloning: A Laboratory Manual*, Second Edition, Cold Spring Harbor Press, NY (1989), and Ausubel et al. (1989) *Current Protocols in Molecular Biology*, John Wiley & Sons, New York, N.Y., which are hereby incorporated by reference in their entirety.

In any of the constructs of the present invention, the DNA molecule imparting the desired trait can be positioned within the DNA construct in the sense (5'→3') orientation. Alternatively, it can have an antisense (3'→5') orientation. Antisense RNA technology involves the production of an RNA molecule that is complementary to the messenger RNA molecule of a target gene. The antisense RNA can potentially block all expression of the targeted gene. In the anti-virus context, plants are made to express an antisense RNA molecule corresponding to a viral RNA (that is, the antisense RNA is an RNA molecule which is complementary to a plus sense RNA species encoded by an infecting virus). Such plants may show a slightly decreased susceptibility to infection by that virus. Such a complementary RNA molecule is termed antisense RNA.

It is possible for the DNA construct of the present invention to be configured so that the trait and silencer DNA molecules encode RNA molecules which are translatable. As a result, that RNA molecule will be translated at the ribosomes to produce the protein encoded by the DNA construct. Production of proteins in this manner can be increased by joining the cloned gene encoding the DNA construct of interest with synthetic double-stranded oligonucleotides which represent a viral regulatory sequence (i.e., a 5' untranslated sequence) (U.S. Pat. No. 4,820,639 to Gehrke, and U.S. Pat. No. 5,849,527 to Wilson, which are hereby incorporated by reference in their entirety).

Alternatively, the DNA construct of the present invention may be configured so that the modified trait and silencer molecules encode an mRNA which is not translatable, i.e., does not result in the production of a protein or polypeptide. This is achieved, for example, by introducing into the modified DNA sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAATGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid. Constructs containing nontranslatable DNA molecules may be particularly useful for results which employ post-transcriptional gene silencing as a mechanism to achieve viral resistance in plants transformed with the DNA constructs of the present invention.

Once the DNA construct of the present invention has been prepared, it is ready to be incorporated into a host cell. Accordingly, another aspect of the present invention relates to a recombinant host cell containing one or more of the DNA constructs of the present invention. Basically, this method is carried out by transforming a host cell with a DNA construct of the present invention under conditions effective to yield transcription of the DNA molecule in the host cell, using standard cloning procedures known in the art, such as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Preferably the host cells are either a bacterial cell or a plant cell. Methods of transformation may result in transient or stable expression of the DNA under control of the promoter. Preferably, a DNA construct of the present invention is stably inserted into the genome of the recombinant plant cell as a result of the transformation, to produce a heritable trait, although transient expression can serve an important purpose, particularly when the plant under investigation is slow-growing.

Plant tissue suitable for transformation include leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue is often achieved by particle bombardment (Klein et al., "High-Velocity Microprojectiles for Delivering Nucleic Acids Into Living Cells," *Nature* 327:70–73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used.

An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Another approach to transforming plant cells with a gene which imparts resistance to pathogens is particle bombardment (also known as biolistic transformation) of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6–12 (1995), which are hereby incorporated by reference in their entirety. Yet another method of introduction is fusion of protoplasts with other entities, either minicells, cells, lysosomes, or other fusible lipid-surfaced bodies (Fraley, et al., *Proc. Natl. Acad. Sci. USA* 79:1859–63 (1982), which is hereby incorporated by reference in its entirety). The DNA molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures, Vol. 1*: (MacMillan Publishing Co., New York, 1983); Vasil I. R. (ed.), *Cell Culture and Somatic Cell Genetics of Plants*, Acad. Press, Orlando, Vol. I, 1984, and Vol. III (1986), and Fitch et al., "Somatic Embryogenesis and Plant Regeneration from Immature Zygotic Embryos of Papaya (*Carica papaya L.*)," *Plant Cell Rep.* 9:320 (1990), which are hereby incorporated by reference in its entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley, et al., *Proc. Natl. Acad. Sci. USA* 80:4803–4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099–1104 (1983), which is hereby incorporated by reference in its entirety). Similarly, "reporter genes," which encode for enzymes providing for production of a compound identifiable are suitable. The most widely used reporter gene for gene fusion experiments has been uidA, a gene from *Escherichia coli* that encodes the β-glucuronidase protein, also known as GUS. Jefferson et al., "GUS Fusions: β Glucuronidase as a Sensitive and Versatile Gene Fusion Marker in Higher Plants," *EMBO J.* 6:3901–3907 (1987), which is hereby incorporated by reference in its entirety. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the viral gene by Southern blot hybridization analysis, using a probe specific to the viral genes contained in the given cassette used for transformation (Sambrook et al., "Molecular Cloning: A Laboratory Manual," Cold Spring Harbor, N.Y.: Cold Spring Harbor Press (1989), which is hereby incorporated by reference in its entirety).

After the DNA construct of the present invention is stably incorporated in transgenic plants, the transgene can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

The present invention can be utilized in conjunction with a wide variety of plants or their seeds. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, and sugarcane. Examples of suitable ornamental plants are: *Arabidopsis thaliana, Saintpaulia*, petunia, pelargonium, poinsettia, chrysanthemum, carnation, and zinnia.

Another aspect of the present invention is a method of imparting one or more desired traits to plants. This may involve transforming a plant with a DNA construct of the present invention containing a modified synthetic nucleic acid molecule of the present invention, regenerating the transgenic plant, and propagating the progeny of the transgenic plant. Alternatively, the seed of the transgenic plant containing the construct of the present invention may be collected, and a transgenic plant propagated from the transgenic plant seed.

The present invention also relates to a method of preparing a modified nucleic acid molecule suitable to impart multiple traits to a plant. This generally involves identifying a plurality of desired traits to be imparted to plants, where the desired traits are imparted by desired trait DNA molecules having nucleotide sequences. This method also involves selecting, as a reference nucleotide sequence, one nucleotide sequence from among the desired trait DNA molecules identified. The nucleotide sequence of the reference nucleic acid molecule is then modified to form a modified nucleic acid molecule which is at least 80% homologous to the nucleotide sequences of the desired DNA molecules identified. Each of the desired trait DNA molecules, relative to the modified nucleic acid sequence, have a nucleotide sequence similarity value and each of these similarity values differs by 3 percentage points or less. This is an important attribute of the modified nucleic acid molecule of the present invention. A synthetic nucleic acid molecule that has a degree of homology within 3 percentage points of each desired trait DNA molecule can be expected to be an effector of RNA degradation in the host cell of a variety of plants. This is because the modified nucleic acid molecule is more similar, on average, than many of the target starting sequences were to one another, or to the consensus sequence. Therefore, it is the combined effect of a high similarity value (i.e., ≧80%) and a low range of variation in similarity relative to the modified nucleic acid, that makes the synthetic molecule of the present invention an effective universal trigger of RNA degradation for the desired trait molecules.

Trait nucleic acid sequences are obtained either from a public database, e.g., GenBank, from a commercial source, or may be known to those who intend to carry out this aspect of the present invention. Once desired trait sequences are identified, they may be used to perform a BLAST search for further homologous nucleotides at the GenBank database, or any other gene database. It is preferable that the nucleic acid sequence selected as a trait molecule be selected from those known to encode full-length, not partial mRNA, and areas of a genome including 5' or 3' untranslated regions and introns be avoided.

Once the desired trait nucleic acid sequences are obtained, the potential locations of sequences amenable to be manipulated to generate a short synthetic sequence are identified. This involves comparing the trait sequences for sequence similarity ("homologizing") to find a common region of high homology among the trait sequences. Any commercially or publicly available software can be used for analysis of the nucleotide sequences in this aspect of the present invention. For example, the comparative analysis of selected DNA sequences the DNAStar package (LaserGene Software, Madison, Wis.) can be used for aligning and editing. DNAStar and the Blast 2 Sequences from NCBI can be used to compare sequences by pairs. To compare the sequence of interest with the GenBank database the Blast program is commonly used (Altschul et al., "Gapped BLAST and PSI-BLAST: A New Generation of Protein Database Search Programs," *Nucleic Acid Research* 25:3389–3402(1997), which is hereby incorporated by reference in its entirety).

For multiple alignment, both ClustalW and Map are suitable (both of them freely available), whereas for searching motifs MEME and MAST programs yield the best results (Bailey et al., "Family Pairwise Search with Embedded Motif Models," *Bioinformatics* 15(6):463–470 (1999); and Bailey et al., "Methods and Statistics for Combining Motif Match Scores," *J. Comput. Biol.* 5(2):211–221 (1998), which are hereby incorporated by reference in their entirety). DNAStar is also capable of generating phylogenetic trees and sequence similarity matrixes. Alignments can also be analyzed with the GeneDoc software (Nicholas et al., "GeneDoc: A Tool For Editing and Annotating Multiple Sequence Alignments" *Software Ver.* 2.6.002 (1997) and similarity trees generated with the Tree View software (Page, Software version 1.6. (2001) both of them freely available on the web and hereby incorporated by reference in their entirety).

A suitable length for the starting sequence of a homologized native DNA, in accordance with the present invention is in the range of 100–200 nts. By using small synthetic sequences, even in multiples, in a transgene, the amount of foreign DNA that is delivered to the plant is minimized. However, this is not meant in any way to set a minimum or maximum limit on the size of starting sequences or the size of the synthetic modified nucleic acid sequence of the present invention. If two sequences are found to be identical, one is discarded. If a region, or block of sequences, of interest can be identified as having at least 80% but less than 100% homology, that block is chosen as the "starting sequence" for each of the desired traits.

From this block of similar nucleotides, a single synthetic (meaning "not naturally occurring") nucleotide sequence with at least 80% homology and a low range of variation in similarity to each of the identified DNA sequences is formed. It is likely that a single synthetic sequence will not be found that has the same percent similarity to each of the starting sequence, and this is acceptable. However, the synthetic modified sequence of the present invention will preferably not vary in percent similarity by more than 3 percentage points when compared to the least and most similar starting sequences. Even more preferably, this variation is no more than 2 percentage points, and most preferably, less than 1 percentage points. In theory, it is possible to create a synthetic sequence that has a 0% variation when compared to all starting sequences. Variations of 5% percentage points in the similarity values between each of the trait DNA molecules and the modified nucleic acid molecule can also be useful.

The reference sequence used for modification to the final synthetic sequence may be any of the starting sequences or the consensus sequence. Preferably, the consensus sequence will not be chosen as the reference sequence when it contains any "N," i.e., any unknown or unidentified nucleotide in the alignment sequence, or when there is no consensus for that position. Two other suitable choices are 1) the starting sequence most similar to all other starting sequences (i.e., having the highest similarity value in comparison to all other trait nucleotides) or 2) the starting sequence most dissimilar to all other starting sequences (i.e., having the lowest similarity value in comparison to all other trait nucleotides). The process is the same regardless of the choice of reference sequence. Nucleotide modifications are made step-wise within the reference sequence, changing those nucleotides that are most different from the other sequences to make the reference sequence more similar to the other starting sequences. The modifications made to the reference sequence will depend on the degree of similarity (or lack thereof) among the starting sequences, and between the starting sequences and the reference sequence. However, in no case is an individual nucleotide that is 100% shared among the homologized sequences modified. The reference sequence may, in some situations (e.g., when the consensus sequence or the most similar sequence, is used as the reference sequence) need to be modified in such a way as to decrease the similarity between it and a potential final synthetic sequence in order to create a synthetic sequence that has a narrow range of variation when comparing the similarity of the synthetic sequence to the least and most similar of the starting sequences. During the modification process, the reference sequence, having been modified as a potential synthetic sequence, will be analyzed against the other starting sequences to assess homology and range of homology. This process of modification of nucleotides followed by similarity analysis may need to be repeated numerous times to achieve a synthetic nucleotide sequence that has a narrow range of variation in similarity, if not 0%, to all the starting trait molecules. A "second" reference sequence can be identified each time the process is repeated, so as to have a second sequence to use for progressive comparative analysis during the process. The second reference sequence can be any of the trait sequences, the consensus sequence from any of the comparisons, or it can be the same sequence chosen as the first reference sequence and previously modified.

When a modified synthetic nucleotide sequence is selected as having the attributes of a synthetic nucleic acid sequence of the present invention and, therefore, is identified as suitable for use in imparting a trait, the synthetic nucleic acid may be prepared by recombinant methodologies including, without limitation, site mutagenesis of one of the original trait nucleic acids; polymerase chain reaction, using an available original nucleic acid and suitable primers, or other methods of nucleic acid manipulation known in the art. As a preferable alternative, the identified homologized nucleotide sequence of present invention can be synthesized using any DNA synthesizer capable of producing an oligonucleotide of the desired size. Thus, the present invention can be carried out without handling the actual source organism for the trait DNA. This eliminates the need for time-consuming recombinant manipulations, significantly reducing both the effort and cost of producing a suitable modified nucleic acid sequence. The resulting modified nucleotide is subsequently cloned into an expression vector suitable for transformation into a chosen host, as described above.

The present invention also relates to a method of determining whether multiple desired traits can be imparted to plants by a single modified DNA molecule. This involves identifying a plurality of desired traits to be imparted to plants, where the desired traits are imparted by desired trait DNA molecules having nucleotide sequences. One nucleotide sequence from among the desired trait DNA molecules identified is selected as a reference nucleotide sequence, and the reference nucleotide sequence is modified. A determination is then made regarding whether the modified nucleic acid molecule is at least 80% homologous to the desired trait DNA molecules identified relative to the modified nucleic acid molecule and whether each of these similarity values differs by no more than 3 percentage points.

As noted above in the Background of the Invention, if sufficient similarity exists between siRNAs and the RNA target, degradation of the RNA ensues and gene silencing occurs. The determination of homology among the various trait nucleotide sequences may be made using any computer program capable of performing nucleotide homology analysis, for example, the DNAStar alignment program. A modified DNA molecule which is determined to have an 80% or greater homology to each of the other identified trait nucleic acid sequences can be expected to impart the desired trait to the transformed plant. The higher the homology over 80%, the greater the expectation that modified nucleotide will impart the desired multiple traits. In addition, the range of variability in homology can be determined (by software analysis) that exists between the modified trait DNA molecule and the nucleotide sequence of the further trait molecules. The less variation in the percent similarity (homology) to the synthetic sequence in comparison to all the starting sequences, the more efficient the DNA construct of the present invention will be in targeting all starting sequences for degradation.

This aspect of the present invention is illustrated in the generalized description that follows.

Four nucleotide sequences having 20 nts each are used here to create a synthetic modified gene which is 80–100% homologous to each of the four chosen nucleic acid sequences, in accordance with the present invention. Each of the starting sequences have only a narrow variation in homology relative to final synthetic sequence.

First, the desired nucleotide sequences are identified and obtained. An alignment is carried out to find a region of high homology among the trait DNA sequences, which can be manipulated to create a synthetic sequence. This is done using any commercially available computer software. In this example, a region of 20 nucleotides was found to be a likely region for this purpose. These "starting sequences" are as follows:

Seq 1 ATAGCGTAGCTAGCTCGAGA (SEQ ID NO: 157)

Seq 2 CTGGCGTATCTAGGTCGAGA (SEQ ID NO: 158)

Seq 3 ATAGCGTAACTAGCTCGAGA (SEQ ID NO: 159)

Seq 4 ATGGCGTAGCTAGGTCGAGA (SEQ ID NO: 160)

Next, the homology, or degree of similarity, among the selected 20 nucleotide starting sequences is determined by performing another alignment using a commercially available computer software. The results of the alignment for Seqs 1–4, showing nucleotide positions that are different from among the sequences in boldfaced type, are as follows:

Seq 1 ATAGCGTAGCTAGCTCGAGA (SEQ ID NO: 157)

Seq 2 CTGGCGTATCTAGGTCGAGA (SEQ ID NO: 158)

Seq 3 ATAGCGTAACTAGCTCGAGA (SEQ ID NO: 159)

Seq 4 ATGGCGTAGCTAGGTCGAGA (SEQ ID NO: 160)

Consensus ATGGCGTAGCTAGGTCGAGA (SEQ ID NO: 161)

The percent of similarity by pairs determined by the alignment software is shown for the four starting nucleotides in Table 1, below.

TABLE 1

| | 1 | 2 | 3 | 4 |
|---|---|---|---|---|
| 1 | | 75% | 95% | 90% |
| 2 | | | 75% | 90% |
| 3 | | | | 85% |

The alignment information becomes the basis of the next step in the process of creating a synthetic nucleotide. Using the values of similarity found by aligning the sequences, a single nucleotide sequence is chosen as a reference sequence which will be manipulated to achieve the synthetic nucleotide. It may also be the consensus sequence (not shown here for Seq. 1–4) as ascertained by the alignment. It is preferable, however, that the reference sequence be the sequence that is most dissimilar from the other sequences.

Next, an approximation is made of how many nucleotides will need to be changed to create the synthetic sequence. The initial assessment uses the Formula as follows:

Nucleotides to be changed=[(range of variation in homology)/2]× average starting sequence length    Formula I where the range of variation is taken from the alignment data. Here, for example, the highest and lowest percentage of homology in the pair-wise alignment, shown in Table 1, above, are 95% and 75%, respectively, for a total variation in homology 20%. Because one of the attributes of the synthetic gene is a sequence with an even distribution of dissimilarity, the variation is divided by two, and then multiplied by the average number of nucleotides in the starting sequences. Here, the average starting sequence number is 20 nt. Formula I is then applied as follows:

$$[(95\%-75\%)/2\times 20\ nt]=2nt$$

Therefore, the number of nucleotides that can be expected to be modified to create a synthetic gene of the present invention is approximately two.

Nucleotide changes are then made in the reference sequence using the alignment charts to determine which changes will bring the reference sequence to a nucleotide composition that is within the goal of greater than 80%, and less than 100%, homology to all the starting sequences. In this example, Seq. 2 is a good choice as a reference sequence, because it has only a 75% similarity to Seq. 1 and Seq. 3, while all other homologies, pair-wise, are higher than 80%. To create a suitable synthetic nucleotide sequence from the reference sequence, it is preferable to avoid making a change to any nucleotide that is identical in all sequences. A suitable starting point for making changes to nucleotides is to identify a position with a nucleotide that is shared by more than two starting sequences, and change the reference sequence to match at that position. For example, in Seq. 2, the reference sequence here, position 1 is “A” in three of the starting sequences, but “C” in Seq. 2. Therefore, modifying position 1 to an “A” in the reference sequence is the first change made here. Next, looking at the alignment data again, it is noted that in Seq. 2, the reference sequence here, position 14 is “G.” Seq. 4 also has a “G” at position 14, while Seq. 1 and 3 have “C” at position 14. Therefore, the starting sequence of Seq. 2 is similar to one of the other four sequences at position 14, and dissimilar to two other sequences (25% similar overall). Changing the “G” in position 14 of Seq. 2 to a “C” will raise the level of homology of the modified Seq. 2, i.e., the reference sequence above that of the starting sequence of Seq. 2, because the reference sequence now is similar at position 14 to 3 out of 5 sequences (the 4 starting sequences and the Reference seq now being a pool of 5), and dissimilar to 2 out 5 other sequences at that position (60% similar). In addition, a change to a “C” at position 14 makes “C” the nucleotide present at 75% of the sequences compared, as opposed to only 50% of the starting sequences.

Step-wise modifications in nucleotides are made in this fashion. Following the initial number of nucleotide changes in a given reference sequence suggested by the application of Formula I above, alignment determinations are made to check if the modification(s) are bringing the reference sequence towards the goal of greater than 80, but less than 100% homology in comparison to each of the starting sequences, and varying in similarity by no more than 3% from each starting trait sequence. This process may need to be repeated a number of times for larger sequences. Modifications can be considered complete when a modified sequence is determined to be at least 80, but less than 100% homologous to all the starting sequences, with the sequences also having a narrow range of variance in percent homology (preferably 3% or less) among the starting sequences in comparison to the synthetic sequence.

For the four starting sequences in this example, the two modifications made at positions 1 and 14, respectively, resulted in the following synthetic sequence:

Synthetic ATGGCGTATCTAGCTCGAGA (SEQ ID NO: 162)

The synthetic sequence compared to the starting sequences and the consensus sequence for the starting sequences are below:

Seq 1 ATAGCGTAGCTAGCTCGAGA (SEQ ID NO: 157)

Seq 2 CTGGCGTATCTAGGTCGAGA (SEQ ID NO: 158)

Seq 3 ATAGCGTAACTAGCTCGAGA (SEQ ID NO: 159)

Seq 4 ATGGCGTAGCTAGGTCGAGA (SEQ ID NO: 160)

Consensus ATGGCGTAGCTAGGTCGAGA (SEQ ID NO: 161)

Synthetic ATGGCGTATCTAGCTCGAGA (SEQ ID NO: 162)

Nucleotides that differ from the synthetic sequence are bolded. This example also demonstrates that a classic consensus sequence is not the same as the synthetic sequence of the present invention. Consensus sequence software is designed to choose the nucleotide that is most frequently repeated in a given position when comparing two or more sequences. Because the synthetic sequence of the present invention requires not only high similarity, but a narrow range of variation, the consensus sequence may vary (even considerably) from the synthetic gene of the present invention.

The homology of the final synthetic sequence compared to the starting sequences is shown in Table 2.

TABLE 2

| | 1 | 2 | 3 | 4 | Cons. | Sync. |
|---|---|---|---|---|---|---|
| 1 | | 75 | 95 | 90 | 90 | 90 |
| 2 | | — | 75 | 90 | 90 | 90 |
| 3 | | | — | 85 | 85 | 90 |
| 4 | | | | — | 100 | 90 |
| Cons. | | | | | | 90 |

In this illustration, each of the starting sequences has a similarity value of 90% in comparison to the modified sequence (i.e., each starting sequence differs from the modified nucleotide sequence by 2 out of 20). Therefore, the difference in the similarity value among the starting sequences relative to the modified sequence is 0%. This is an “ideal” modified nucleotide according to the present invention i.e., not only is the degree of homology high relative to each starting sequence; each has exactly the same degree of homology to the modified nucleic acid.

The universality of the present invention has been demonstrated by the feasibility of inactivating genes by RNAi, not only in plants, but also in vertebrate and invertebrate systems (Caplen et al., "Specific Inhibition of Gene Expression By Small Double-Stranded RNAs in Invertebrate and Vertebrate Systems," (2001)), including cultured mammalian cells (Elbashir et al., "Duplexes of 21-Nucleotides RNAs Mediate RNA Interference In Cultured Mammalian Cells, *Nature* 411:494–498 (2001), which are hereby incorporated by reference in their entirety). Thus, the present invention has potential application in many biological, and even non-biological systems.

EXAMPLES

Example 1

Synthetic Sequence Assembly and Amplification by PCR

The oligonucleotides used for the assembly and amplification of the synthetic gene fragments derived from the ¾ N gene of TSV-BL are listed in Table 3, below. For the assembly and amplification of the aforementioned constructs the protocol of Stemmer et al., "Single-Step Assembly of a Gene and Entire Plasmid from Large Numbers of Oligodeoxyribonucleotides," *Gene* 164(1):49–53 (1995), which is hereby incorporated by reference in its entirety, was essentially followed. Briefly, for the assembly step, 1 µl of each oligonucleotides (250 µM) corresponding to every single construct, were mixed in combinations as shown in Table 4 to produce the 10 final constructs. From this mixture an aliquot of 0.2 µl was mixed with 0.2 mM for each of the dNTPs, 50 mM KCl, 10 mM Tris-HCl (pH 9.0), 0.1% Triton® X-100, 2.25 mM MgCl$_2$, 1 unit of Taq polymerase and 0.5 units of Pfu polymerase in a final reaction volume of 20 µl. Conditions for PCR, in all cases, were as follows: 55 cycles of denaturing at 94° C. for 30 seconds, annealing at 52° C. for 30 seconds, and extension at 72° C. for 30 seconds. From the assembly step 2.5 µl were mixed for amplification with the appropriate pair of primers, as shown in Table 2, at a final concentration of 1 µM each, 0.2 mM for each of the dNTPs, 50 mM KCl, 10 mM Tris-HCl (pH 9.0), 0.1% Triton® X-100, 2.25 mM MgCl$_2$, 5 units of Taq polymerase and 0.5 units of Pfu polymerase in a final reaction volume of 100 µl. Conditions for amplification were: 35 cycles of denaturing at 92° C. for 30 seconds, annealing at 65° C. for 30 seconds and extension at 72° C. for 2 minutes. Size and yield of every single product were determined by agarose gel electrophoresis with molecular markers of known concentration.

TABLE 3

Oligos used for the synthesis and amplification of all different constructs

| Sequence | SEQ ID NO | Name |
|---|---|---|
| 5'-ATCATTCTCGAGGCAAAGTCTGTGAGGC-3': | SEQ ID NO: 163 | TS-N-1AH |
| 5'-TTGCCATAATGCTGGGAGGTAGCTTACCTCTTATTGCTTC-3': | SEQ ID NO: 164 | TS-N-2H |
| 5'-AGTTGATAGCTTTGAGATGATCAGTGTTGTCTTGGCTATA-3': | SEQ ID NO: 165 | TS-N-3H |
| 5'-TATCAGGATGCAAAATACAAGGATCTCGGGATCGACCCAA-3': | SEQ ID NO: 166 | TS-N-4H |
| 5'-AGAAGTATGACACCAGGGAAGCCTTAGGAAAAGTTTGCAC-3': | SEQ ID NO: 167 | TS-N-5H |
| 5'-TGTGCTGAAAAGAAAAGCATTTGAAATGAATGAAGATCAG-3': | SEQ ID NO: 168 | TS-N-6H |
| 5'-AGCTAAGGATCCCTGATCTTCATTCATTTCAA-3': | SEQ ID NO: 169 | TS-N-1AC |
| 5'-ATGCTTTTCTTTTCAGCACAGTGCAAACTTTTCCTAAGGC-3': | SEQ ID NO: 170 | TS-N-2C |
| 5'-TTCCCTGGTGTCATACTTCTTTGGGTCGATCCCGAGATCC-3': | SEQ ID NO: 171 | TS-N-3C |
| 5'-TTGTATTTTGCATCCTGATATATAGCCAAGACAACACTGA-3': | SEQ ID NO: 172 | TS-N-4C |
| 5'-TCATCTCAAAGCTATCAACTGAAGCAATAAGAGGTAAGCT-3': | SEQ ID NO: 173 | TS-N-5C |
| 5'-ACCTCCCAGCATTATGGCAAGCCTCACAGACTTTGCCTCG-3': | SEQ ID NO: 174 | TS-N-6C |
| 5'-TT<u>C</u>CCATAATGCTGGGAGGTA<u>T</u>CTTACCTCTTATTGCTTC-3': | SEQ ID NO: 175 | TS-S-211 |
| 5'-<u>T</u>GTTGATAGCTTTGAGATG<u>T</u>TCAGTGTTGTCTTGGCTA<u>A</u>A-3': | SEQ ID NO: 176 | TS-S-3H |
| 5'-TATCAGGATGCAAAATA<u>G</u>AAGGATCTCGGGATCGAC<u>G</u>CAA-3': | SEQ ID NO: 177 | TS-S-4H |
| 5'-AGAAGTATGACACCA<u>C</u>GGAAGCCTTAGGAAAAGT<u>A</u>TGCAC-3': | SEQ ID NO: 178 | TS-S-5H |
| 5'-TGTGCTGAAAAGA<u>T</u>AAGCATTTGAAATGAATG<u>T</u>AGATCAG-3': | SEQ ID NO: 179 | TS-S-6H |
| 5'-AGCTAAGGATCCCTGATCT<u>A</u>CATTCATTTCAA-3': | SEQ ID NO: 180 | TS-S-1AC |
| 5'-ATGCTT<u>A</u>TCTTTTCAGCACAGTGCA<u>T</u>ACTTTTCCTAAGGC-3': | SEQ ID NO: 181 | TS-S-2C |
| 5'-TTCC<u>G</u>TGGTGTCATACTTCTTTG<u>C</u>GTCGATCCCGAGATCC-3': | SEQ ID NO: 182 | TS-S-3C |
| 5'-TT<u>C</u>TATTTTGCATCCTGATAT<u>T</u>TAGCCAAGACAACACTGA-3': | SEQ ID NO: 183 | TS-S-4C |

TABLE 3-continued
Oligos used for the synthesis and amplification of all different constructs

| | | |
|---|---|---|
| 5'-ACATCTCAAAGCIATCAACAGAAGCAATAAGAGGTAAGAT-3': | SEQ ID NO: 184 | TS-5-5C |
| 5'-ACCTCCCAGCATTATGGGAAGCCTCACAGACTTTGCCTCG-3': | SEQ ID NO: 185 | TS-5-6C |
| 5'-ATCATTCTCGAGCGTTTCAGACAGAGGC-3': | SEQ ID NO: 186 | TS-5-5'-1AH |
| 5'-ACCTCCCAGCATTATGGCAAGCCTCTGTCTGAAACGCTCG-3': | SEQ ID NO: 187 | TS-5-5'-6C |
| 5'-TGTGCTGAAAAGAAAAGCATTTGAAATGATACTTCTAGTC-3': | SEQ ID NO: 188 | TS-5-3'-6H |
| 5'-AGCTAAGGATCCTCATTTCAA-3': | SEQ ID NO: 189 | TS-5-3'-1AC |
| 5'-AAAATACAAGGATCTCGGGATCGACCCAA-3': | SEQ ID NO: 190 | TS-5-m-4H |
| 5'-TTGTATTTTTATAGCCAAGACAACACTGA-3': | SEQ ID NO: 191 | TS-5-m-4C |
| 5'-ATCATTCTCGAG-3': | SEQ ID NO: 192 | TS-10-5'-1AH |
| 5'-TATAGCCAAGACAACACTGA-3': | SEQ ID NO: 193 | TS-10-m-4C |
| 5'-AGCTAAGGATCC-3': | SEQ ID NO: 194 | TS-10-3'-1AC |
| 5'-ATCATTCTCGAGCCAAAGACTGTGACGC-3': | SEQ ID NO: 195 | TS-15-1AH |
| 5'-TTGCGATAATGGTGGGAGCTAGCTTTCCTCTTTTTGCTTG-3': | SEQ ID NO: 196 | TS-15-2H |
| 5'-AGTTGACAGCTTTCAGATGAACAGTGTAGTCTTGCCTATA-3': | SEQ ID NO: 197 | TS-15-3H |
| 5'-TTTCAGGAAGCAAAAAACAAGGTTCTCGGCATCGACGCAA-3': | SEQ ID NO: 198 | TS-15-4H |
| 5'-AGATGTATGAGACCAGGCAAGCCTAAGGAAATGTTTGCTC-3': | SEQ ID NO: 199 | TS-15-5H |
| 5'-TGTGCTCAAAAGATAAGCATATGAAATCAATGAACATCAC-3': | SEQ ID NO: 200 | TS-15-6H |
| 5'-AGCTAAGGATCCGTGATGTTCATTGATTTCAT-3': | SEQ ID NO: 201 | TS-15-1AC |
| 5'-ATGCTTATCTTTTGAGCACAGAGCAAACATTTCCTTAGGC-3': | SEQ ID NO: 202 | TS-15-2C |
| 5'-TTGCCTGGTCTCATACATCTTTGCGTCGATGCCGAGAACC-3': | SEQ ID NO: 203 | TS-15-3C |
| 5'-TTGTTTTTTGCTTCCTGAAATATAGGCAAGACTACACTGT-3': | SEQ ID NO: 204 | TS-15-4C |
| 5'-TCATCTGAAAGCTGTCAACTCAAGCAAAAAGAGGAAAGCT-3' | SEQ ID NO: 205 | TS-15-5C |
| 5'-AGCTCCCACCATTATCGCAAGCGTCACAGTCTTTGGCTCG-3': | SEQ ID NO: 206 | TS-15-6C |
| 5'-ACCTCTCG-3': | SEQ ID NO: 207 | TS-15-5'-6C |
| 5'-TGTGCTGA-3': | SEQ ID NO: 208 | TS-15-3'-6H |
| 5'-TCAGCACAGTGCAAATTTTCCTAAGGC-3': | SEQ ID NO: 209 | TS-15-3'-2C |
| 5'-CGACCCAA-3': | SEQ ID NO: 210 | TS-15-m-4H |
| 5'-TTCCCTGGTGTCATACTTCTTTGGGTCG3': | SEQ ID NO: 211 | TS-15-m-3C |
| 5'-ATCATTCTCGAGGCAATGTCTCTGAGCC-3': | SEQ ID NO: 212 | TS-20-1AH |
| 5'-TTGGCATATTGCTCGGAGCTAGCATACCACTTAATGCTAC-3': | SEQ ID NO: 213 | TS-20-2H |
| 5'-AGTAGATACCTTTCAGATCATCACTGTTCTCTTCGCTAAA-3': | SEQ ID NO: 214 | TS-20-3H |
| 5'-TATGAGGAAGCAATATACTAGGAACTCGCGATCCACCCTA-3': | SEQ ID NO: 215 | TS-20-4H |
| 5'-AGATGTATCACACGAGGGTAGCCATAGGTAAAGATTGCTC-3': | SEQ ID NO: 216 | TS-20-5H |
| 5'-TGTCCTGATAAGATAAGCTTTTGTAATGTATGATGATCTG-3': | SEQ ID NO: 217 | TS-20-6H |
| 5'-AGCTAAGGATCCCAGATCATCATACATTACAA-3': | SEQ ID NO: 218 | TS-20-1AC |
| 5'-AAGCTTATCTTATCAGGACAGAGCAATCTTTACCTATGGC-3': | SEQ ID NO: 219 | TS-20-2C |
| 5'-TACCCTCGTGTGATACATCTTAGGGTGGATCGCGAGTTCC-3': | SEQ ID NO: 220 | TS-20-3C |
| 5'-TAGTATATTGCTTCCTCATATTTAGCGAAGAGAACAGTGA-3': | SEQ ID NO: 221 | TS-20-4C |

TABLE 3-continued

Oligos used for the synthesis and amplification of all different constructs

| Sequence | SEQ ID NO | Name |
|---|---|---|
| 5'-TGATCTGAAAGGTATCTACTGTAGCATTAAGTGGTATGCT-3' | SEQ ID NO: 222 | TS-20-5C |
| 5'-AGCTCCGAGCAATATGCCAAGGCTCAGAGACATTGCCTCG-3' | SEQ ID NO: 223 | TS-20-6C |
| 5'-ATCATTCTCGAGGCAAAATCTGTGAGAC-3' | SEQ ID NO: 224 | Rec2-1AH |
| 5'-TTGCCATAATGCTGGGAGGTAGTATCCCTCTTATTGCTTC-3' | SEQ ID NO: 225 | Rec2-2H |
| 5'-TGTTGACAGCTTTGAAATGATCAGTGTTGTCCTTGCTATA-3' | SEQ ID NO: 226 | Rec2-3H |
| 5'-TATCAAGATGCAAAATACAAGGATCTCGGGATTGAACCAA-3' | SEQ ID NO: 227 | Rec2-4H |
| 5'-CGAAGTATAACACTAAGGAAGCCTTAGGAAAAGTTTGCAC-3' | SEQ ID NO: 228 | Rec2-5H |
| 5'-TGTGCTGAAAAGCAAAGGATTTACAATGGATGAAGATCAG-3' | SEQ ID NO: 229 | Rec2-6H |
| 5'-AGCTAAGGATCCCTGATCTTCATCCATTGTAA-3' | SEQ ID NO: 230 | Rec2-1AC |
| 5'-ATCCTTTGCTTTTCAGCACAGTGCAAACTTTTCCTAAGGC-3' | SEQ ID NO: 231 | Rec2-2C |
| 5'-TTCCTTAGTGTTATACTTCGTTGGTTCAATCCCGAGATCC-3' | SEQ ID NO: 232 | Rec2-3C |
| 5'-TTGTATTTTGCATCTTGATATATAGCAAGGACAACACTGA-3' | SEQ ID NO: 233 | Rec2-4C |
| 5'-TCATTTCAAAGCTGTCAACAGAAGCAATAAGAGGGATACT-3' | SEQ ID NO: 234 | Rec2-5C |
| 5'-ACCTCCCAGCATTATGGCAAGTCTCACAGATTTTGCCTCG-3' | SEQ ID NO: 235 | Rec2-6C |

FIG. 1 shows the scheme of the 216 bp TSWV fragment and the corresponding primers to be named to be used for its synthesis. The diagonal lines indicate the place in the oligos where six random nucleotides and six nucleotides corresponding to restriction sites are located: XhoI for the 5' end (left) and BamHI for the 3' end (right). The XX in the middle of the oligo name refers to the percentage of change for every single construct according to Tables 1 and 2. The fragment is shown in the sense orientation.

Example 2

Cloning and Sequencing

Figure 2:
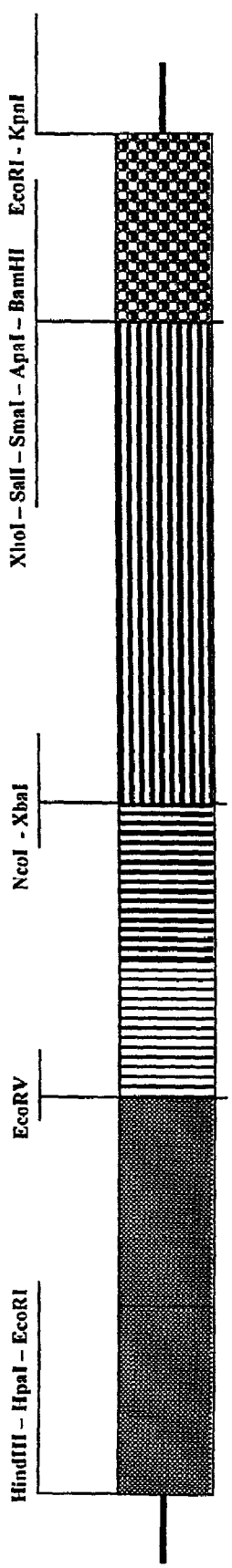
FIG. 2 is a schematic representation of the cloning/expression cassette vector pEPJ86GFP. The expression vector is located in a pUC backbone between the HindIII and KpnI sites in the multiple cloning site (MCS) adjacent to the lacZ gene. In the same order, from left to right, the expression cassette contains a double 35S CaMV enhancer (the first two 'hatched' regions), the 35S Cauliflower Mosaic Virus (CaMV) promoter (striped regions with thin vertical lines), the Alfalfa Mosaic Virus leader sequence (region with thick vertical lines), the green fluorescent protein (GFP) gene (region of horizontal lines), and the CaMV 35S terminator sequence (bubbled region). After sequence confirmation the HindIII/KpnI fragments were subcloned into the plant transformation vector pGA482G.

All gene fragments were digested with an excess of BamHI and XhoI for no less than 12 hours, according to Sambrook et al., "Molecular Cloning: A Laboratory Manual," Cold Spring Harbor, N.Y.: Cold Spring Harbor Press (1989), which is hereby incorporated by reference in its entirety. The digested fragments were excised from agarose gels and column purified for ligation into the BamHI/XhoI cloning site of vector pEPJ86GFP, shown in FIG. 2. In this cloning vector, a transcriptional fusion with GFP gene was created under the control of a double 35S promoter. For chemical or electro transformation either Escherichia coli DH5α or XL1-Blue were routinely used. For plasmid miniprep either the alkaline lysis or the boiling method were used. Five independent recombinant plasmids per construct were sequenced; plasmids with identical sequence to the computer-generated gene fragments were chosen for digestion and subsequent subcloning into pGA482G. Digestion with KpnI and HindIII renders a subcloning fragment with the GFP gene fused to the synthetic ¾ N gene fragment, and under the control of the 35S promoter. After checking by PCR and restriction analysis the recombinant derivatives of pGA482G were sequenced again before transforming Agrobacterium tumefaciens LBA4404.

A. tumefaciens transformants were kept at −80° C. after checking for the recombinant plasmid by restriction analysis. PCR products from transgenic plants were also column purified and sequenced from at least three different transgenic lines. All sequencing was done using an ABI 373 automated sequencer.

Example 3

Plant Transformation

Leaf discs of young, greenhouse-grown Nicotiana benthamiana plants were transformed with A. tumefaciens as described essentially by Horsch (Horsch et al., "A Simple and General Method for Transferring Genes into Plants," Science, 227:1229–31 (1985), which is hereby incorporated by reference in its entirety). Transformed leaf discs were selected and regenerated in MS medium containing 250 mg/L of carbenicillin and 150 mg/L of kanamycin sulfate. Rooting was induced in a hormone-free medium in the presence of both antibiotics. All regenerated and rooted explants derived from independent calli. Fully rooted transformants were transferred to Cornell soil mixture and grown under greenhouse conditions. Transgenic plants were self-pollinated and seeds were collected from all of them at the end of the experiments.

Example 4

Inoculation of Transgenic Plants

Seedlings of 5–7 leaf stage grown in the greenhouse were challenged with either TSWV-BL or GRSV. Both viruses were multiplied in N. benthamiana, tested by ELISA for tospoviruses and by indirect ELISA with specific antibodies raised against each virus. After multiplication and immunotesting individual leaves were kept at −20° C. for inoculation experiments. A week in advance to inoculation of transgenic plants non-transgenic *N. benthamiana* was infected with the frozen leaves to serve as a source of fresh virus inoculum. In every round of inoculation of no more than 50 plants per set, 4 non-transgenic plants were included as a control. Infected leaves were ground in a 0.033 M $KH_2PO_4$, 0.067 M $K_2HPO_4$, and 0.01 M $Na_2SO_3$ cold buffer. Ten-fold diluted leaf extract was immediately applied onto carborundum-dusted leaves, and subsequently rinsed with water. Symptoms were recorded daily starting 5 days after inoculation, but only weekly 2 weeks after inoculation and until the plants set seeds. At least one leaf was taken from every plant before infection and stored at −20° C. for further RNA extraction.

Example 5

Plant DNA and RNA Extraction

DNA from 100 mg of transgenic and non-transgenic *N. benthamiana* leaves was extracted according to Fulton et al., "Microprep Protocol for Extraction of DNA from Tomato and Other Herbaceous Plants," *Plant Molecular Biology Reporter* 13(3):207–209 (1995), which is hereby incorporated by reference in its entirety, from plants 3 weeks old. DNA was kept in water at −20° C. until used for PCR or Southern analysis. RNA was extracted before and after infection from plants 3 and 6 weeks old, respectively, according to Napoli et al., "Introduction of a Chimeric Chalcone Synthase Gene into Petunia Results in Reversible Co-suppression of Homologous Genes in Trans," *Plant Cell* 2:279–290 (1990), which is hereby incorporated by reference in its entirety, using 100 mg of leaves. In all cases, concentration was determined by spectrophotometry at 260 nm, and integrity in agarose gels for DNA and denaturing agarose gels for RNA.

Example 6

Northern and Southern Analysis

Probes for hybridization by Southern and Northern analysis were labeled with $\alpha$-$^{32}$P-dATP by random priming according to Feinberg et al., "A Technique for Radiolabeling DNA Restriction Endonuclease Fragments to High Specific Activity," *Anal. Biochem.* 132(1):6–13 (1983), which is hereby incorporated by reference in its entirety. For Southern analysis 15 µg of DNA from transgenic and non-transgenic lines were digested with an excess of restriction enzymes for at least 16 hours. Electrophoresis, transfer, and DNA fixation onto nylon membranes were performed as recommended by the manufacturer (NEN Life Sciences, Boston, Mass.). Hybridization was carried out with the homologous ¾ N gene fragment of the analyzed samples. After 24 hours of hybridization at 65° C., membranes were washed according to manufacturer's recommendations (NEN Life Sciences, Boston, Mass.). For Northern analysis, after 24 hours hybridization at 60° C., membranes were washed as before. After washing the membrane was put in contact with an auto radiographic film for different intervals of time. For Northern analysis membranes were stripped and hybridized with an $\alpha$-$^{32}$P-dATP-labeled actin gene.

Example 7

Software

For the design, virtual assembly, and alignment of all synthetic and native sequences the DNAStar program was used. Sequences were used to perform a BLAST search for homologous sequences at the GenBank database. For measuring band intensities both in photographed gels and in X-ray films the NIH Scio Image 1.59 software was used.

Example 8

Design and Synthesis of ¾N TSWV-BL N Gene

Sequence modifications made to a DNA fragment are generally limited by the availability of restriction sites, but also by the ability of mutating at random, or even site-specifically, the gene under analysis. When trying to establish how important nucleotides changes are, both the number and the location of nucleotide changes must be assessed under controlled conditions. This is, by far, the most important requisite in the design for making synthetic genes with specific desired properties, to test different hypothesis, and to attain specific plant phenotypes. Based on a sequence previously known to confer resistance, new fragments of 216 bp of TSWV N gene were designed with nucleotides changes to render scattered, 5' end, middle and 3' end region constructs differing by 5% and 15%, and scattered 10% and 20% from the native N TSWV-BL gene. A starting assumption was that in modifying the nucleotide sequence of a previous fragment proven to confer resistance in transgenic plants, a point would be reached in which resistance was no longer viable. In this way, information could be gathered regarding what extent of similarity is important to trigger post-transcriptional gene silencing, and, even more importantly, on how the location of nucleotide changes affect the phenotype of transgenic plants when challenged with the homologous virus.

Figure 3:
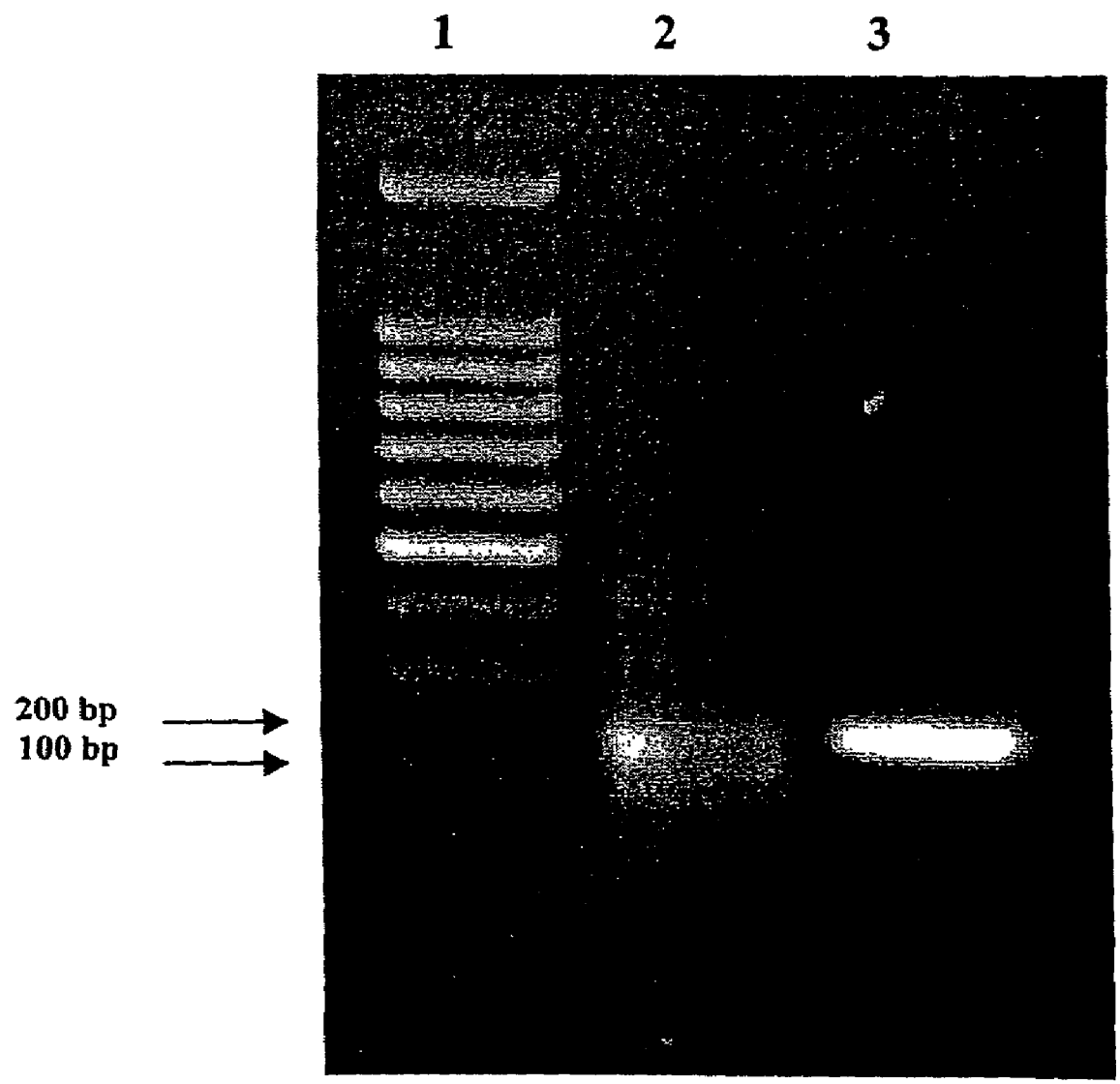
FIG. 3 shows a gel electrophoresis of one of the PCR assembly and amplification products obtained in this work (e.g., 5% changes in this case). Row 1: a molecular ladder 100 bp step; Row 2: assembled products after 55 cycles of all mixed different oligonucleotides, as described in examples; Row 3: a unique, single amplification product from the assembled reaction, prior to digestion.

Using the strategy originally devised by Stemmer et al., "Single-Step Assembly of a Gene and Entire Plasmid from Large Numbers of Oligodeoxyribonucleotides," *Gene* 164 (1):49–53 (1995), which is hereby incorporated by reference in its entirety, the constructs indicated by Table 4 were synthesized. The engineered N gene fragment of TSWV-BL (the lettuce isolate of TSWV) is the nucleotide sequence designated as ¾N by Pang et al., "Nontarget DNA Sequences Reduce the Transgene Length Necessary for RNA-Mediated Tospovirus Resistance in Transgenic Plants," *Proc. Natl. Acad. Sci. USA,* 94:8261–8266 (1997), which is hereby incorporated by reference in its entirety), which corresponds to bases 2668–2373 (antisense orientation) according to Pang et al., "Resistance to Heterologous Isolates of Tomato Spotted Wilt Virus in Transgenic Plants Expressing its Nucleocapsid Protein Gene," *Phytopathology,* 82: 1223–29 (1992), which is hereby incorporated by reference in its entirety. All fragments were 216 nt long, but adding the restriction recognition sites and random nucleotides introduced for cloning purposes, all assembled products are 240 nt long. No cloning from native virus was required. Even the native version of the ¾N gene fragment was synthetic, but also used as controls were ¾N-transgenic segregating lines previously obtained in this laboratory. In this sense the synthetic N gene fragment here used is identical to the one published by Pang et al., "Resistance to Heterologous Isolates of Tomato Spotted Wilt Virus in Transgenic Plants Expressing its Nucleocapsid Protein Gene," *Phytopathology* 82: 1223–29 (1992), which is hereby incorporated by reference in its entirety, and all modified constructs derived from this single original sequence. This sequence was chosen as a baseline due to its short size and its ability to confer good level of resistance to TSWV when transcriptionally fused to GFP gene. The design of the oligos and the changes introduced to the N subcloning process. All 10 newly-created sequences harbored only the restriction sites purposely introduced in the amplification oligos for cloning purposes (BamHI and XhoI). In all cases, the introduced nucleotide changes were transversions; meaning that no overall change in G+C content is expected. The 10 constructs created are listed in Table 4.

TABLE 4

| % Changes | Location | Assembly Primers | Amplification Primers |
|---|---|---|---|
| None | | TS-N-2H, TS-N-3H, TS-N-4H, TS-N-5H, TS-N-6H, TS-N2C, TS-N-3C, TS-N-4C, TS-N-5C, TS-N-6C | TS-N-1AH, TS-N-1AC |
| 5 | Scattered | TS-5-2H, TS-5-3H, TS-5-4H, TS-5-5H, TS-5-6H, TS-5-2C, TS-5-3C, TS-5-4C, TS-5-5C, TS-5-6C | TS-N-1AH, TS-5-1AC |
| 5 | 5' | TS-N-2H, TS-N-3H, TS-N-4H, TS-N-5H, TS-N-6H, TS-N2C, TS-N-3C, TS-N-4C, TS-N-5C, TS-5-5'-6C | TS-5-5'-1AH, TS-N-1AC |
| 5 | Middle | TS-N-2H, TS-N-3H, TS-5-m-4H, TS-N-5H, TS-N-6H, TS-N2C, TS-N-3C, TS-5-m-4C, TS-N-5C, TS-N-6C | TS-N-1AH, TS-N-1AC |
| 5 | 3' | TS-N-2H, TS-N-3H, TS-N-4H, TS-N-5H, TS-5-3'-6H, TS-N2C, TS-N-3C, TS-N-4C, TS-N-5C, TS-N-6C | TS-N-1AH, TS-5-3'-1AC |
| 10 | Scattered | Rec2-2H, Rec2-3H, Rec2-4H, Rec2-5H, Rec2-6H, Rec2-2C, Rec2-3C, Rec2-4C, Rec2-5C, Rec2-6C | Rec2-1AH, Rec2-1AC |
| 15 | Scattered | TS-15-2H, TS-15-3H, TS-15-4H, TS-15-5H, TS-15-6H, TS-15-2C, TS-15-3C, TS-15-4C, TS-15-5C, TS-15-6C | TS-15-1AH, TS-15-1AC |
| 15 | 5' | TS-15-5'-2H, TS-N-3H, TS-N-4H, TS-N-5H, TS-N-6H, TS-N2C, TS-N-3C, TS-N-4C, TS-N-5C, TS-15-5'-6C | TS-10-5'-1AH, TS-N-1AC |
| 15 | Middle | TS-N-2H, TS-N-3H, TS-15-m-4H, TS-N-5H, TS-N-6H, TS-N2C, TS-15-m-3C, TS-10-m-4C, TS-N-5C, TS-N-6C | TS-N-1AH, TS-N-1AC |
| 15 | 3' | TS-N-2H, TS-N-3H, TS-N-4H, TS-N-5H, TS-15-3'-6H, TS-15-3'-2C, TS-N-3C, TS-N-4C, TS-N-5C, TS-N-6C | TS-N-1AH, TS-10-3'-1AC |
| 20 | Scattered | TS-20-2H, TS-20-3H, TS-20-4H, TS-20-5H, TS-20-6H, TS-20-2C, TS-20-3C, TS-20-4C, TS-20-5C, TS-20-6C | TS-20-1AH, TS-20-1AC | sequence were performed by computer using the DNAStar software program. For every construct, all oligos required for their synthesis were individually designed and the complementary strand deduced using the DNAStar software. When all oligo sequences were deduced they were introduced in a different program of the same software to allow its virtual assemblage. All of them, without exception, gave a unique contig that matches 100% with the intended sequence when assembled as indicated in Table 4. That is, no other assemblage product was produced in this simulation-like exercise. Afterwards, computer-simulated restriction analysis were performed to assess whether the introduced changes created BamHI, XhoI, KpnI, and/or HindIII restriction sites that would eventually complicate the cloning and The strategy here used was devised by Stemmer et al., "Single-Step Assembly of a Gene and Entire Plasmid from Large Numbers of Oligodeoxyribonucleotides," Gene 164 (1):49–53 (1995), which is hereby incorporated by reference in its entirety, to assemble and amplify a synthetic bla (ampicillin resistance) gene in *E. coli.* Briefly, a set of different oligos corresponding to both strands of the DNA of interest is synthesized and mixed together in a PCR tube. After transformation and plasmid DNA extraction, samples were digested and those that yielded the expected size fragment were sequenced. In all cases, the sequence of the cloned gene matched perfectly with the virtual version of the designed fragment obtained by computer analysis. One example is shown in FIG. 3. All of the different synthetic constructs have the exact sequence generated by computer analysis.

Example 9

Figure 5:
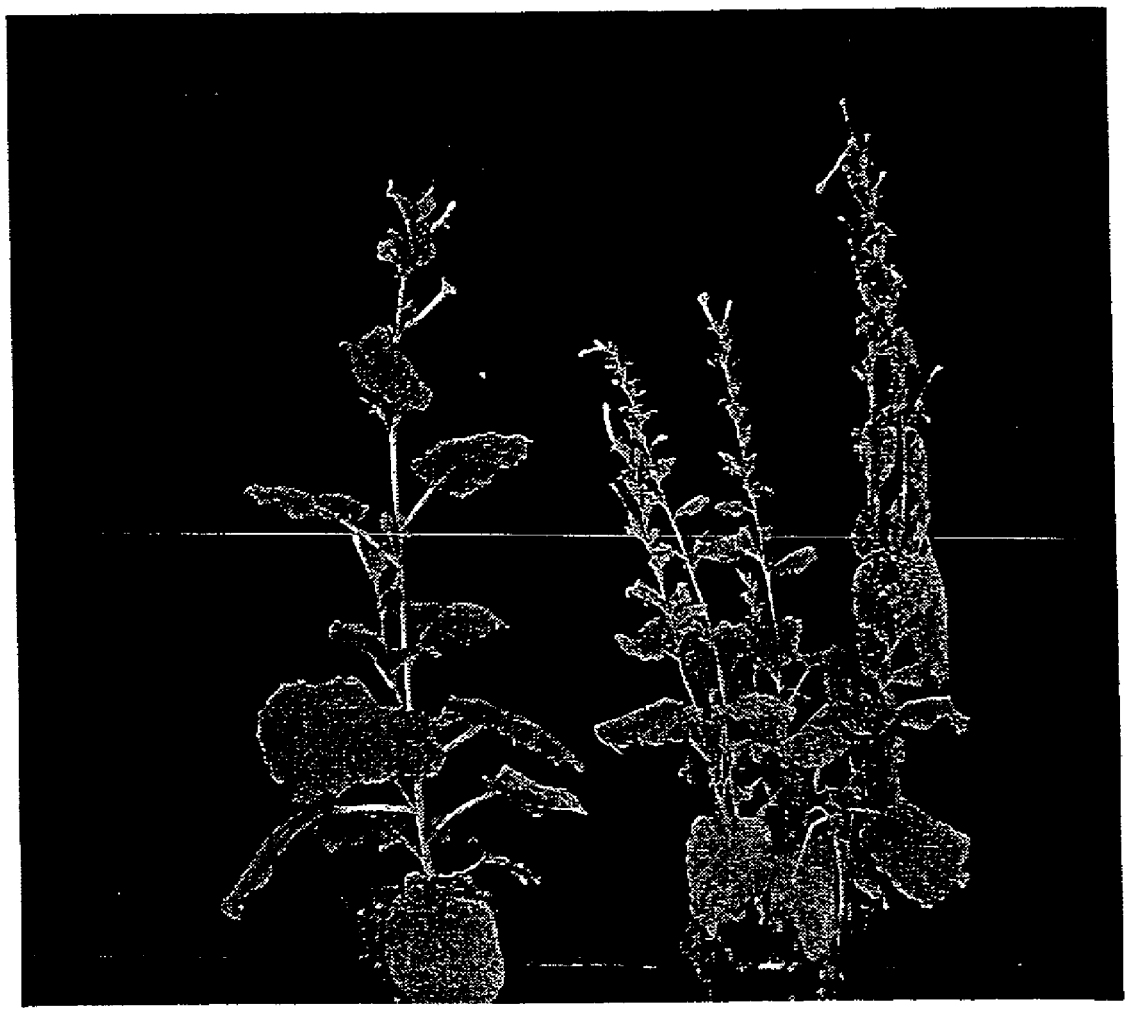
FIG. 5 shows susceptible and resistant plants: a transgenic (left) and a non-transgenic (right) plant four weeks after inoculation with TSWV-BL.

Both Degree of Similarity and Location of Nucleotide Changes Affect the Ability of a ¾N Transgene in Conferring Resistance to TSWV-BL The first goal was to determine how location of nucleotide changes, and the amount of those changes, affect the ability of transgenic plants to be resistant to TSWV. The fragment chosen for engineering (i.e., the third fourth of the TSWV N gene, ¾ N) proved to be very effective when transcriptionally fused to GFP. The nucleotide sequence of such a fragment was modified and used to transform *N. benthamiana* plants. Plants were analyzed by PCR for nptII and ¾ N gene; as shown in FIG. 4, and some selected lines for every construct were tested by Southern and Northern analysis. Results of inoculation are shown in Table 5, and examples of susceptible and resistant plants in FIG. 5.

TABLE 5

Response of *N. benthamiana* Transgenic Plants to TSWV Infection: Summary of Results by Construct

| Inserted transgene[a] | | Transgenic lines/phenotype[b] | | | |
|---|---|---|---|---|---|
| % Changes | Position | Total | Susceptible | Delay | Resistant |
| 5% | 5' | 57 | 23 | 2 | 32 (56.1%) |
| | M | 38 | 15 | — | 23 (60.5%) |
| | 3' | 51 | 30 | — | 21 (42.2%) |
| | Scattered | 33 | 13 | — | 20 (57.5%) |
| 15% | 5' | 64 | 31 | — | 33 (51.5%) |
| | M | 61 | 26 | 6 | 29 (47.5%) |
| | 3' | 36 | 20 | — | 16 (44.4%) |
| | Scattered | 20 | 14 | 1 | 5 (25.0%) |
| 20% | Scattered | 50 | 43 | 5 | 2 (4.0%) |
| None | Synthetic N | 36 | 14 | — | 22 (61.1%) |
| | Native N[c] | 50 | 21 | 6 | 23 (46.1%) |
| | Native N[d] | 19 | 5 | 3 | 11 (57.8%) |

[a]All genes, native or synthetic, correspond to the third fourth of the N gene of TSWV-BL.
[b]In vitro or seed-derived plants were kept in the greenhouse and inoculated at the 5–7 leavesstage with a 1:10 dilution of the virus, and scored daily until they set flowers.
[c]Segregating R1 plants from Pang et al., "Nontarget DNA Sequences Reduce the Transgene LengthNecessary for RNA-Mediated Tospovirus Resistance in Transgenic Plants," Proc. Natl. Acad. Sci. USA,94: 8261–66 (1997) which is hereby incorporated by reference in its entirety) N-transgenic line 5 seeds.
[d]Segregating R1 plants from Pang et al., "Nontarget DNA Sequences Reduce the Transgene LengthNecessary for RNA-Mediated Tospovirus Resistance in Transgenic Plants," Proc. Natl. Acad. Sci. USA,94: 8261–66 (1997) which is hereby incorporated by reference in its entirety) N-transgenic line 22 seeds.

As expected, a higher number of nucleotide changes that diminish sequence similarity between the transgene and the incoming virus have a detrimental effect on viral resistance. For 5%, 15%, and 20% changes, the number of resistant transgenic plants were 57.5%, 25%, and 2%, respectively. The highest number of resistant plants was obtained with the synthetic, unmodified version of ¾N gene (61.1%). Even at levels of homology as low as 80%, it is still possible to obtain some level of resistance. The 2 out of 50 plants with 20% changes that showed some level of resistance are under analysis in the second generation. This trend is also evident when all plants with a similar amount of changes are added up, regardless of the location, as shown in Table 6.

TABLE 6

Response of *N. benthamiana* Transgenic Plants to TSWV Infection (Summary of results by percentage of change)*

| Inserted transgene[a] | | Transgemic lines/phenotype[b] | | |
|---|---|---|---|---|
| % Changes | Number | Susceptible | Delay | Resistant |
| 5 | 179 | 81 | 2 | 96 (53.6%) |
| 15 | 181 | 91 | 7 | 83 (45.9%) |
| 20 | 50 | 43 | 5 | 2 (4.0%) |
| None: synthetic | 47 | 19 | — | 28 (59.6%) |
| None: native[c] | 50 | 21 | 6 | 23 (46.0%) |
| None: native[d] | 19 | 5 | 3 | 11 (57.8%) |

*Sum of all positions for same amount of changes, according to Table 3.
[a]All genes, native or synthetic, correspond to the third fourth of the N gene of TSWV-BL
[b]In vitro or seed-derived plants were kept in the greenhouse and inoculated at the 5–7 leaves stage with a 1:10 dilution of the virus, and scored daily until they set flowers.
[c]Segregating R1 plants from Pang et al., "Nontarget DNA Sequences Reduce the Transgene Length Necessary for RNA-Mediated Tospovirus Resistance in Transgenic Plants," Proc. Natl. Acad. Sci. USA, 94: 8261-66 (1997) which is hereby incorporated by reference in its entirety) N-transgenic line 5 seeds.
[d]Segregating R1 plants from Pang et al., "Nontarget DNA Sequences Reduce the Transgene Length Necessary for RNA-Mediated Tospovirus Resistance in Transgenic Plants," Proc. Natl. Acad. Sci. USA, 94: 8261-66 (1997) which is hereby incorporated by reference in its entirety) N-transgenic line 22 seeds.

It also appears that location of nucleotide changes in the transgene can exert an impact on transgenic resistance. Both for sequences with 5% and 15% changes, the number of resistant plants with engineered changes at the 3' end was lower when compared with plants with changes clustered at the 5' end or the middle section of the gene fragment. Apparently, the 3' end is somehow more critical in conferring resistance than the 5' end, regardless of the length of the modified 3' end, as shown in Table 5 and in Table 7, which shows a summary of results by location of change.

TABLE 7

Response of *N. benthamiana* Transgenic Plants to TSWV Infection

| Inserted transgene[a] | | Transgenic lines/phenotype[b] | | |
|---|---|---|---|---|
| Location of change | Number | Susceptible | Delay | Resistant |
| 5' end | 121 | 54 | 2 | 65 (53.8%) |
| 3' end | 87 | 50 | — | 37 (42.3%) |
| middle | 99 | 41 | 6 | 52 (52.5%) |
| None: synthetic | 47 | 19 | — | 28 (59.6%) |
| None: native[c] | 50 | 21 | 6 | 23 (46.0%) |
| None: native[d] | 19 | 5 | 3 | 11 (57.8%) |

* Sum of all different percentage of changes for same position, according to Table 3.
[a]All genes, native or synthetic, correspond to the third fourth of the N gene of TSWV-BL.
[b]In vitro or seed-derived plants were kept in the greenhouse and inoculated at the 5–7 leaves stage with a 1:10 dilution of the virus, and scored daily until they set flowers.
[c]Segregating R1 plants from Pang et al., "Nontarget DNA Sequences Reduce the Transgene Length Necessary for RNA-Mediated Tospovirus Resistance in Transgenic Plants," Proc. Natl. Acad. Sci. USA, 94: 8261-66 (1997) which is hereby incorporated by reference in its entirety) N-transgenic line 5 seeds.
[d]Segregating R1 plants from Pang et al., "Nontarget DNA Sequences Reduce the Transgene Length Necessary for RNA-Mediated Tospovirus Resistance in Transgenic Plants," Proc. Natl. Acad. Sci. USA, 94: 8261-66 (1997) which is hereby incorporated by reference in its entirety) N-transgenic line 22 seed.

Example 10

A Synthetic ¾N Gene, 216 bp Long Can Confer Resistance to Both TSWV and GRSV

Transgenic plants transformed with ¾N gene fused to GFP can confer resistance to TSWV but not to the related tospovirus Groundnut Ringspot Virus (GRSV). TSWV and GRSV are 78% similar, and it is possible that the lack of resistance of transgenic plants challenged with GRSV is due to a level of homology which is insufficient to target the GRSV genome for degradation, even if post-transcriptional gene silencing is triggered. To further explore the possibility that modifying the TSWV ¾N transgene would allow broader viral resistance of transgenic plants, a gene was synthesized that is, in toto, approximately 90% similar to the corresponding fragments of both TSWV and GRSV. To design this sequence, a ¾N TSWV gene was modified to make it more homologous to the GRSV N gene nucleotide sequence. In doing so, of course, the similarity to the native TSWV N gene decreased, the net result being that the artificial sequence presented here is 90% similar to both TSWV N gene and its counterpart in GRSV. The nt 1417–1632 (in sense form) of TSWV and nt 560–775 of GRSV were used. The newly created synthetic sequence (called Rec2 herein), when compared with its parental ¾N TSWV-BL gene sequence, has the following changes: one insertion and one deletion, plus 22 base changes (ca. 10% changes compared with the native sequence of ¾N TSWV gene). Similarity of TSWV N gene dropped from 100% to 90% according to sequence alignment. Similarity to GRSV rose from 73% to 89% according to the same analysis. The homologous gene of Tomato Chlorotic Spot Virus (TCSV), another member of the same group as TSWV and GRSV, is also 89% similar to Rec2, as seen in Table 8. In FIG. 6, all modifications are highlighted and uninterrupted stretches of full similarity are also indicated.

TABLE 8

Sequence Similarity (%) Among 216 bp 3/4 N Gene Fragments of Selected Tospoviruses and Recombinant, Synthetic Sequence Rec2.

| | TSWV | TCSV | GRSV | Rec2 |
|---|---|---|---|---|
| TSWV | 100.0 | 78.7 | 73.1 | 90.0 |
| TCSV | | 100.0 | 77.3 | 89.0 |
| GRSV | | | 100.0 | 89.0 |
| Rec2 | | | | 100.0 |

The values here tabulated were originated by annealing the sequences by pairs instead of a single, multiple analyses. For that purpose BLAST 2 Sequences algorithm and program was used.

Approximately 27% of the transgenic lines analyzed showed a good level of resistance against either TSWV or GRSV. At first glance, plants transformed with constructs differing by 10% from its native source support the trend observed for scattered changes. The proportion of resistant plants with engineered constructs differing by 10% lies between the values observed for plants transformed with 5% changes (56.1%) and 15% changes (25%)—although very similar for the latter. It must be taken into consideration that changes for construct Rec2 were not made at random, and the distance between changed nucleotides is not even; this was the case for all the other scattered changes constructs. A second important observation is that the original hypothesis—i.e., that a DNA fragment can be engineered that confers resistance to two different viruses whose "natural" similarity is below a threshold to trigger post-transcriptional gene silencing—can be effectively applied to obtain transgenic plants with multiple viral resistance. Using the current model for post-transcriptional gene silencing and RNA-interference, it would be possible to engineer a construct not only to confer resistance to three-distantly related virus, but also to manipulate other genetic traits using a single, short, gene fragment built from the information of different gene systems.

Example 11

Response to Infection of Transgenic *Nicotiana benthamiana* Plants

*Nicotiana benthamiana* plants were transformed with a ¾ N TSWV-BL gene fragment modified for a 90% similarity to TSWV, GRSV and TCSV according to the examples above. The transgenic plants were then challenged with TSWV-BL or GRSV. Table 9 shows the results of virus resistance for the transgenic plants.

TABLE 9

Response to Infection of Transgenics With a ¾ N TSWV-BL Modified Fragment

| Challenging virus | Total Plants | Resistant | Susceptible |
|---|---|---|---|
| TSWV-BL | 10 | 3 (30%) | 7 |
| GRSV | 15 | 4 (27%) | 11 |
| Total | 25 | 7 (28%) | 18 |

Example 12

A Synthetic Sequence Derived From Three PRSV Isolates

A set of synthetic genes were designed according to the present invention to target for degradation the RNAs of three different isolates of PRSV. The isolates were the Keaau (Hawaii) strain ("KE"), the Thailand strain ("TH"), and the severe Taiwan strain ("YK"). The starting sequences were the conserved and variable regions, respectively of the coat protein ("CP") gene. For the analysis of selected DNA sequences, the DNAStar package (LaserGene Software, Madison, Wis.) was used for editing and aligning. DNAStar and the Blast 2 Sequences from NCBI were used to compare sequences by pairs. To compare the sequence of interest with the GenBank database, the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). For multiple alignment both ClustalW and Map were employed (both of them freely available), whereas for searching motifs MEME and MAST yielded the best results (Bailey et al, "New Tools for Quantifying Molecular Diversity," *Pharmainformatics* 6–7 (1999); Bailey et al., "Combining Evidence Using p-Values: Application to Sequence Homology Searches," *Bioinformatics* 14:48–54 (1998), which are hereby incorporated by reference in their entirety). DNAStar can also be used to generate phylogenetic trees and sequence similarity matrices. The CP gene sequences employed for this work were isolated and were sequenced in inventors' laboratory.

Alignments were also analyzed with the GeneDoc software Nicholas et al., "GeneDoc: A Tool For Editing and Annotating Multiple Sequence Alignments" *Software Ver.* 2.6.002 (1997), and similarity trees generated with the Tree View software (Page, Software version 1.6. (2001), both of them freely available on the web.

The similarity matrix for the conserved and variable regions of the CP gene for the KE, TH and YK isolates and the synthetic sequence created for the conserved region and the variable region is shown below in Table 10.

TABLE 10

| | Conserved region (203 nt) | | | | Variable region (209 nt) | | | |
|---|---|---|---|---|---|---|---|---|
| | KE | TH | YK | Syn-con | | KE | TH | YK | Syn-var |
| KE | 100.0 | 94.1 | 94.1 | 97.0 | KE | 100.0 | 83.5 | 83.7 | 91.9 |
| TH | | 100.0 | 96.1 | 97.0 | TH | | 100.0 | 85.4 | 91.7 |
| YK | | | 100.0 | 97.0 | YK | | | 100.0 | 91.9 |
| Syn-con | | | | 100.0 | Syn-var | | | | 100.0 |

Isolates under comparison are KE, Keaau (Hawaii); TH, Thailand; YK, Severe Taiwan strain. "Syncon" standsfor the synthetic sequence for the conserved region, and "Synvar" for variable region.

FIG. 7 shows the starting sequences for the conserved regions of the CP gene of TH (SEQ ID NO: 6), KE (SEQ ID NO: 7) and YK (SEQ ID NO: 8) compared to each other and to the sequence of the modified synthetic nucleic acid (SEQ ID NO: 5) sequence generated for targeting these PRSV isolates. The underlined portions identify segments of more than 20 nt long of perfect similarity. The nucleotide changes differing from the synthetic sequence are shown in lowercase. Because the homology of the three starting sequences chosen for the isolates was high, a high homology (97%) synthetic sequence with a low variation (range: 0%) was created, as shown in Table 10.

FIG. 8 shows the distribution of dissimilar nucleotides compared to the synthetic gene (SEQ ID NO: 9) for the variable regions of the of the CP gene of TH (SEQ ID NO: 10) KE (SEQ ID NO: 11) and YK (SEQ ID NO: 12). The underlined portions identify segments of more than 20 nt long of perfect similarity. The nucleotide changes differing from the synthetic sequence are shown in lowercase. The starting homologies among the variable regions of the CP gene are shown in Table 10. In this case, the homology of the starting sequence was 84.2%, and was raised to 91.8% when compared to the synthetic sequence. In addition, the variation among the starting sequences relative to the synthetic is very low, >1%.

Note that in both cases, as seen in FIG. 7 and FIG. 8, the long fragments of perfect similarity are present in all of the three isolates when compared with the sequence of the synthetic transgene. The rationale of this approach is based on the proposed concept that the mediator molecules of dsRNA that trigger gene silencing seem to be 20–27 nt long (Hamilton et al., "A Species of Small Antisense RNA in Posttranscriptional Gene Silencing in Plants," *Science* 286: 950–952 (1999); Waterhouse et al., "Role of Short RNAs in Gene Silencing," *Trends in Plant Science* 6:297–301 (2001), which are hereby incorporated by reference in their entirety). This is not meant to limit in any way the size of similar segments chosen for a synthetic sequence of the present invention in comparison with the desired trait DAN molecules.

Example 13

A Synthetic Sequence Derived From Diverse Potyviruses

A synthetic sequence was generated according to the present invention to target for degradation a variety of different potyviruses. The desired trait is potyvirus resistance in different crop plants, both dicots and monocots. Therefore, the complete potyvirus genome was the starting point for this synthetic sequence. Nineteen sequences from potyviruses whose complete genomes have been already sequenced, having an overall homology of 34–83%, were chosen as starting nucleotide sequences for comparative analysis. The nucleotide sequences were obtained from the GenBank database. A variety of genes of the potyvirus genome were potential candidates for applying the method of the present invention. Table 11, below, gives the numerical coordinates of all the genes of the potyviruses used for this analysis.

Table 12 shows an analysis of percent of nucleotide identity for all different genes in selected potyviruses. Using this type of analyses assists in selecting a gene within a genome suitable for generating the synthetic nucleic acid molecule of the present invention.

TABLE 11

| VIRUS | 5'UTR[a] | P1 (1)[b] | HC-PRO[c] | P3[d] | 6K1[e] | CI[f] | 6k2[g] | NIa-VPg[h] | NIa-Pro[i] | NIb[j] | CP (2)[k] | 3'UTR[l] |
|---|---|---|---|---|---|---|---|---|---|---|---|---|
| Bean common mosaic | 1 | 131 | 1400 | 2771 | 3812 | 3968 | 5870 | 6029 | 6599 | 7328 | 8876 | 9737 |
| Japanese yam mosaic | 1 | 154 | 1135 | 2509 | 3574 | 3730 | 5662 | 5821 | 6397 | 7126 | 8680 | 9553 |
| Maize dwarf mosaic | 1 | 140 | 839 | 2219 | 3260 | 3461 | 5375 | 5534 | 6101 | 6827 | 8390 | 9263 |
| Papaya ringspot | 1 | 86 | 1727 | 3098 | 4133 | 4289 | 6210 | 6365 | 6932 | 7646 | 9197 | 10199 |
| Peanut Mottle | 1 | 123 | 1086 | 2460 | 3507 | 3663 | 5565 | 5724 | 6294 | 7032 | 8586 | 9423 |
| Peanut Stripe | 1 | 134 | 1463 | 2834 | 3875 | 4031 | 5933 | 6092 | 6662 | 7391 | 8939 | 9800 |
| Pea seed-borne | 1 | 144 | 1338 | 2715 | 3771 | 3927 | 5835 | 5994 | 6567 | 7305 | 8865 | 9738 |
| Pepper mottle | 1 | 168 | 1029 | 2397 | 3480 | 3636 | 5538 | 5694 | 6258 | 6996 | 8553 | 9372 |
| Plum pox | 1 | 147 | 1071 | 2445 | 3495 | 3651 | 5556 | 5715 | 6294 | 7023 | 8577 | 9522 |
| Potato Y | 1 | 185 | 1056 | 2427 | 3468 | 3624 | 5529 | 5688 | 6255 | 7010 | 8573 | 9373 |
| Potato A | 1 | 162 | 1037 | 2405 | 3500 | 3656 | 5558 | 5714 | 6278 | 6984 | 8532 | 9339 |
| Ryegrass mosaic | 1 | 113 | 881 | 2246 | 3302 | 3461 | 5372 | 5531 | 6110 | 6833 | 8153 | 9371 |
| Scallion mosaic | 1 | 110 | 743 | 2114 | 3176 | 3332 | 5264 | 5423 | 5999 | 6728 | 8279 | 9113 |
| Soybean mosaic N | 1 | 132 | 1056 | 2427 | 3468 | 3624 | 5526 | 5685 | 6255 | 6984 | 8535 | 9330 |
| Sugarcane mosaic | 1 | 150 | 849 | 2229 | 3260 | 3471 | 5385 | 5544 | 6111 | 6837 | 8400 | 9339 |
| Sweet Potato feathery mottle | 1 | 118 | 2110 | 3484 | 4540 | 4696 | 6625 | 6784 | 7360 | 8089 | 9652 | 10597 |
| Tobacco etch | 1 | 144 | 1056 | 2433 | 3474 | 3633 | 5532 | 5691 | 6255 | 6981 | 8517 | 9306 |
| Turnip mosaic | 1 | 131 | 1217 | 2591 | 3656 | 3812 | 5744 | 5903 | 6479 | 7208 | 8759 | 9623 |

TABLE 11-continued

| VIRUS | 5'UTR[a] | P1 (1)[b] | HC-PRO[c] | P3[d] | 6K1[e] | CI[f] | 6k2[g] | NIa-VPg[h] | NIa-Pro[i] | NIb[j] | CP (2)[k] | 3'UTR[l] |
|---|---|---|---|---|---|---|---|---|---|---|---|---|
| Zucchini yellow mosaic | 1 | 139 | 1069 | 2437 | 3475 | 3631 | 5533 | 5692 | 6262 | 6991 | 8542 | 9379 |

(1)Including the ATG codon;
(2)Not including the Stop codon;
[a]5' untranslated region;
[b]Protein 1;
[c]Helper component Protease;
[d]protein 3;
[e]6 kda 'protein 1';
[f]cytoplasmic inclusion protein;
[g]6 kda 'protein 2';
[h]Nuclear inclusion protein a-viral genome linked protein;
[i]protease nuclear inclusion protein a;
[j]Nuclear inclusion protein b;
[k]Coat Protein;
[l]3' untranslated region.

TABLE 12

| Gene | Length (nt) | Percent Similarity (%) ClustalW | | Maximum Workable Length (nt) | Quality |
|---|---|---|---|---|---|
| 5' UTR | 85–184 | 22–80 | | 30 | Low |
| P1 | 633–1992 | 19–85 | | 20 | Low |
| HC-Pro | 1368–1380 | 39–86 | 1: | 85 | Medium |
| | | | → 2: | 158 | Medium |
| | | | 3: | 90 | Medium |
| P3 | 1035–1083 | 30–81 | | 83 | Low |
| 6K1 | 156–211 | 27–86 | | 59 | Low |
| CI | 1899–1932 | 50–82 | 1: | 152 | Medium |
| | | | 2: | 46 | High |
| | | | → 3: | 188 | Medium |
| 6K2 | 96–159 | 27–81 | | <20 | Low |
| NIa Pro | 706–738 | 45–88 | 1: | 94 | Medium |
| | | | 2: | 190 | Low |
| NIa VPg | 564–579 | 42–87 | → 1: | 121 | Medium |
| | | | 2: | 105 | Medium |
| NIb | 1320–1563 | 54–86 | → 1: | 211 | High |
| | | | → 2: | 273 | High |
| CP | 801–1218 | 37–91 | → 1: | 201 | High |
| | | | → 2: | 250 | Medium |
| 3' UTR | 165–331 | 18–93 | None | None | |
| Whole genome | 9324–10820 | 34–83 | Indicated | Indicated | |

From these 19 potyviruses, the group was narrowed down to the 9 potyviruses, shown along with their accession numbers, in Table 13, below.

TABLE 13

| Plant Species | Gene | Accession Number |
|---|---|---|
| Bean common mosaic virus | Complete Genome | NC 003397 |
| Maize dwarf mosaic virus | Complete Genome | NC 003377 |
| Peanut mottle virus | Complete Genome | NC 002600 |
| Pea seed-borne mosaic virus | Complete Genome | AJ252242 |
| Pepper mottle virus | Complete Genome | NC 001517 |
| Potato virus Y | Complete Genome | NC 001616 |

TABLE 13-continued

| Plant Species | Gene | Accession Number |
|---|---|---|
| Soybean mosaic virus N | Complete Genome | NC 002634 |
| Sugarcane mosaic virus | Complete Genome | NC 003398 |
| Zucchini yellow mosaic virus | Complete Genome | NC 003224 |

Figure 9:
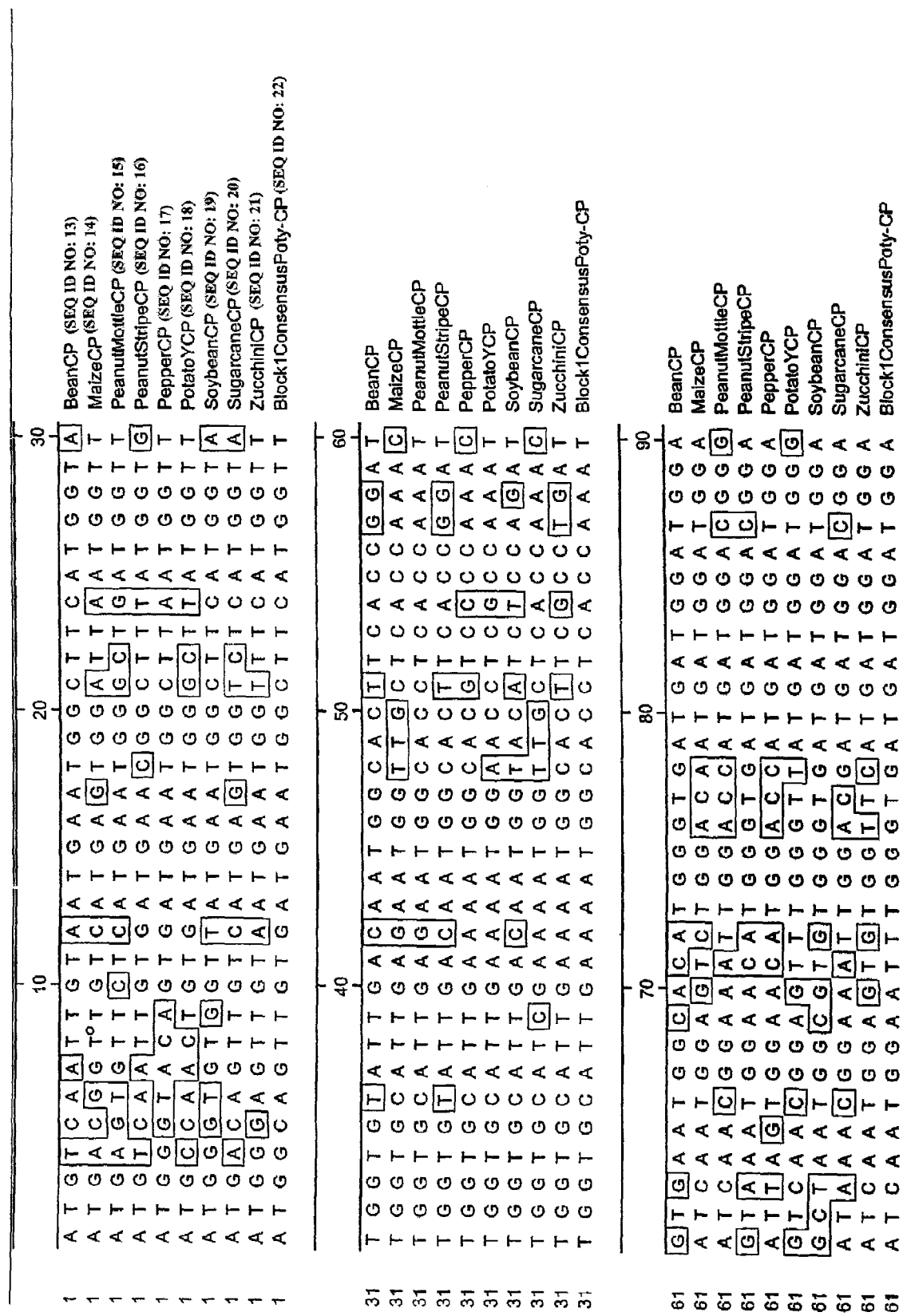
FIG. 9 shows the CLUSTALW alignment of the nine selected potyvirus sequences (SEQ ID NO: 13–SEQ ID NO: 22) and their consensus sequence before modification.
Figure 12:
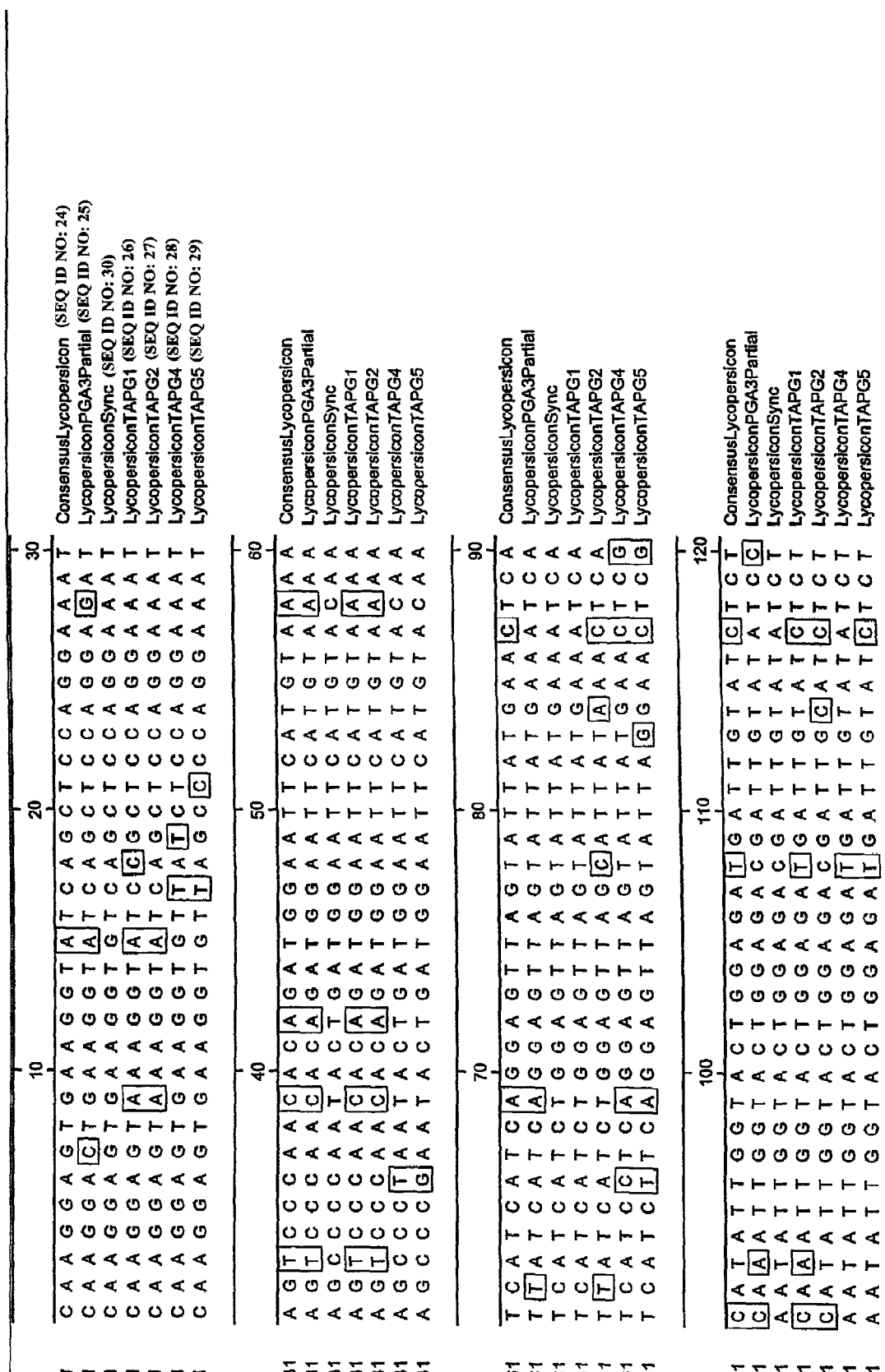
FIG. 12 shows the CLUSTALW alignment of the nine selected potyvirus sequences and their consensus sequence from FIG. 11 after modification in comparison to the synthetic modified potyvirus sequence (SEQ ID NO: 30).

The nine selected potyvirus genes were compared and analyzed using DNAStar package (LaserGene Software, Madison, Wis.) which was utilized for editing and aligning. DNAStar and the Blast 2 Sequences from NCBI were used to compare sequences by pairs. To compare the sequence of interest with the GenBank database, the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). For multiple alignment both ClustalW and Map were employed (both of them freely available), whereas for searching motifs MEME and MAST yielded the best results (Bailey et al, "New Tools for Quantifying Molecular Diversity," *Pharmainformatics* 6–7 (1999); Bailey et al., "Combining Evidence Using p-Values: Application to Sequence Homology Searches," *Bioinformatics* 14:48–54 (1998), which are hereby incorporated by reference in their entirety). FIG. 9 shows the CLUSTALW alignment of the nine selected potyvirus sequences and their consensus sequence. The similarity among the nine native sequences, having approximately 200 nucleotides, was determined to be 64.4–92.1% (range: 27.7%). The similarity with the consensus sequence identified for the nineteen sequences was found to be: 75.2–86.6% (range: 11.4%). Using Formula I supra, it was determined the total number of changes would be approximately 20. A reference sequence was chosen from among the starting sequences, and nucleotide changes were made by reviewing the alignment data of FIG. 9 and determining those modifications that would result in a single synthetic sequence with a homology of greater than 80, but less than 100% relative to each starting sequence, and which would also result in variation in percent identity narrower than 3%. After approximately 20 nucleotides were changed, the CLUSTALW alignment was run again as shown in FIG. 10. The similarity with the synthetic gene was determined to be 74.3–78.2% (range: 3.9%). Thus, a single 202 nt synthetic gene was designed in this step-wise fashion. This synthetic modified potyvirus nucleic acid molecule has a nucleotide sequence of SEQ ID NO: 23 as follows:

```
atgggagttg tgatgaatgg cctcatggtt tggtgcattg aaaatggaac ctcaccaaac   60
atcaatggag tatgggctat gatggatggg gacgaacaag ttgagtttcc attaaagcca  120
gtgattgaga atgcaaagcc aacttttcga caaatcatgc atcatttttc agatgcagca  180
gaagcttaca tagagtagag ca                                           202
```

This example illustrates that the present invention can be applied to a highly divergent trait DNA group with significant results in terms of creating a molecule that is a marked improvement over the variation in homology found among the members of the group in nature. The range of homology was reduced from 27.7% for the starting sequences themselves to 3.9% for the starting sequences in comparison to the modified sequence. It is highly probable that with further manipulations in accordance with the present invention, a suitable single modified nucleic acid molecule will be created that has yet a lower range in homology with respect to the starting trait DNA group.

Note that more than one "block" or region of homology can be used from different genes, and sequences can be grouped separately to create chimeras of the same block or chimeras of different blocks. The one presented here is just one example of a multitude of possibilities.

Example 14

A Synthetic Sequence to Delay Fruit Ripening Using a Synthetic Polygalacturonase Gene Derived from Different Plants A synthetic sequence was generated according to the present invention to target for degradation of different genes of the same gene family in the same plant, in this case the polygalacturonase ("PG") gene of tomato. The desired trait to be imparted by this synthetic gene is delayed fruit ripening.

PG is a well-characterized enzyme family implicated in the disassembly of pectin that accompanies many stages of plant development, in particular, fruit ripening (Sheehy et al., "Reduction of Polygalacturonase Activity in Tomato Fruit by Antisense RNA," *Proc. Natl. Acad. Sci. USA* 85:8805–8809 (1988); Smith et al., "Antisense RNA Inhibition of Polygalacturonase Gene Expression in Transgenic Tomatoes," *Nature* 334:724–726 (1988); Giovannoni et al., "Expression of a Chimeric Polygalacturonase Gene in Transgenic Rin (Ripening Inhibitor) Tomato Fruit Results in Polyuronide Degradation But Not Fruit Softening," *Plant Cell* 1:53–63 (1989), which are hereby incorporated by reference in their entirety). Delivery to market of mature, full-flavored, and unadulterated fruits, such as tomato and papaya, is a challenge to producers, especially when long-distance transport is involved. Therefore, the ability to control fruit ripening is a commercially desirable trait.

Five reported sequences for the polygalacturonase gene in *Lycopersicon esculentum* were obtained from GenBank, as shown Table 14.

TABLE 14

| Plant Species | Gene | GenBank Accession Number |
|---|---|---|
| *Lycopersicon esculentum* | Polygalacturonase 3 (TAPG3) gene | AF000999 |
| *Lycopersicon esculentum* | Polygalacturonase 5 (TAPG5) gene | AF001003 |
| *Lycopersicon esculentum* | Polygalacturonase 4 (TAPG4) gene | AF001002 |
| *Lycopersicon esculentum* | Polygalacturonase 2 (TAPG2) gene | AF001001 |
| *Lycopersicon esculentum* | Polygalacturonase 1 (TAPG1) gene | AF00100 |

Once the sequence were obtained, DNAStar package (LaserGene Software, Madison, Wis.) was used for editing and aligning. DNAStar and the Blast 2 Sequences from NCBI were used to compare sequences by pairs. To compare the sequence of interest with the GenBank database the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). For multiple alignment both ClustalW and Map were employed (both of them freely available), whereas for searching motifs MEME and MAST yielded the best results (Bailey et al, "New Tools for Quantifying Molecular Diversity," *Pharmainformatics* 6–7 (1999); Bailey et al., "Combining Evidence Using p-Values: Application t Sequence Homology Searches," *Bioinformatics* 14:48–54 (1998), which are hereby incorporated by reference in their entirety). FIG. 11 shows the alignment of the five selected tomato PG sequences and their consensus sequence. The similarity among the five native sequences was determined to be 86.0–96.1% (range: 10.1%). The similarity with the consensus sequence was determined to be 90.3–96.6% (range: 6.3%). Using Formula I supra, it was determined that approximately 20 nucleotides could be expected to be modified in order to create a suitable synthetic sequence to target PG RNA. Using a reference sequence chosen from among the starting PG sequences, nucleotides were changed stepwise to create a single 207 nt synthetic gene. The similarity with the synthetic gene was determined to be 92.3–93.2% (range: 0.9%) for all of the starting tomato genes. The modified nucleic acid molecule has a high percent homology, and, importantly, also has an decreased variation in similarity, as compared to all the starting sequences. This means that the synthetic nucleic acid molecule is more likely to be an effector of RNA degradation in a variety of plants because it is more similar, on average, than many of the native starting sequences were to one another, or to the consensus sequence. FIG. 12 shows the percent identity determined for the five starting sequences compared to the synthetic sequence. This synthetic gene is then cloned into an appropriate vector, as described above herein, and used to transform a tomato plant, plant cell, or plant line. The transgene can be engineered by creating a sequence having inverted repeats that lead to the production of a dsRNA upon transcription in the transgenic plant Without being bound to a theory, a transgene engineered in this way should lead to gene silencing of the endogenous gene, and, in this case, delayed plant ripening in the transgenic tomato plant.

This synthetic modified tomato PG nucleic acid molecule has a nucleotide sequence of SEQ ID NO: 30 as follows:

```
caaggagtga aggtgtcagc tccaggaaat agccccaata ctgatggaat tcatgtacaa    60
tcatcatctg gagttagtat tatgaaatca aatattggta ctggagacga ttgtatatct   120
attggccctg gaacttcgaa cttatggatt gaaggcattg cttgtggccc tggccatgga   180
ataagcattg gaagcttagg ctgggaa                                        207
```

Example 15

A Synthetic Gene Using Chalcone Synthase Genes in Petunia

A synthetic sequence was generated according to the present invention to target for degradation different genes of the same gene family in the same plant, using the chalcone synthase gene of Petunia. In flowers, as well as food crops, the ability to manipulate color through genetic engineering is desirable because it is more predictable and less time-consuming than classic breeding methods. Thus, the desired trait in this example is the species-specific inactivation of color development in Petunia. Petunia was also chosen as a representative of the application of the present invention to a dicot. Six reported sequences for the chalcone synthase gene of Petunia, shown below in Table 15 along with their GenBank accession numbers, were chosen.

TABLE 15

| Plant Species | Gene | GenBank Accession Number |
| --- | --- | --- |
| Petunia x hybrida | chalcone synthase (chs) mRNA | AF233638 |
| Petunia hybrida | chsJ gene for chalcone synthase | X14597 |
| Petunia hybrida | chsG gene for chalcone synthase | X14595 |
| Petunia hybrida | chsF gene for chalcone synthase | X14594 |
| Petunia hybrida | chsD gene for chalcone synthase | X14593 |
| Petunia hybrida | chsB gene for chalcone synthase | X14592 |

Figure 13:
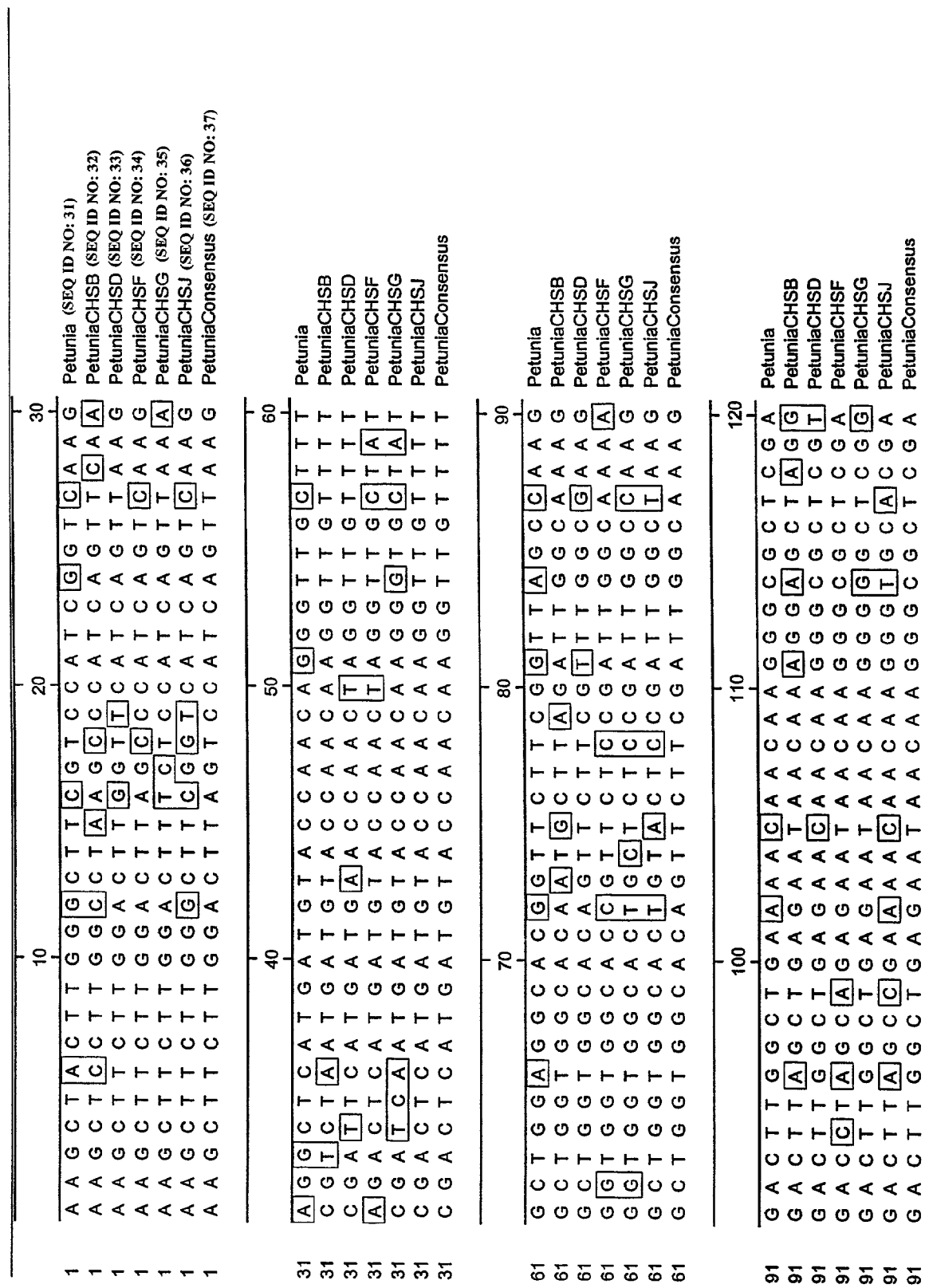
FIG. 13 shows the CLUSTALW alignment of the six selected Petunia chalcone synthase ("CHS") sequences and their consensus sequence (SEQ ID NO: 31–SEQ ID NO: 37) before modification.

The genes of the six Petunia CHS genes were compared and analyzed using both ClustalW and MAP for multiple alignment. DNAStar package (LaserGene Software, Madison, Wis.) was used for editing and aligning, and DNAStar and the Blast 2 Sequences from NCBI were used to compare sequences by pairs. To compare the sequence of interest with the GenBank database the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). FIG. 13 shows the homology of the starting sequences and their consensus sequence. The similarity among the six sequences was determined to be 76.1–86.6% (range: 10.5%). The similarity with the consensus sequence was determined to be 83.6–93.3% (range: 9.7%). A single 134 nt synthetic gene, SEQ ID NO: 38, shown below, was manually designed using the region of high homology within the identified consensus sequences. The similarity with the synthetic gene was determined to be 85.8–86.6% (range: 0.8%) for all of the starting Petunia genes. The synthetic modified nucleic acid molecule for Petunia CHS not only has an improved degree of homology, having raised the least homologous starting sequence from 76.1% to 85.8%, but it also has a narrow range of variation in similarity compared to all starting sequences, i.e., 0.8% compared to a range of 10.5% variation in similarity among the native starting sequences. This combination of homology greater than 80% and a narrow range of variation make the Petunia synthetic nucleic acid molecule a good candidate for degrading RNA in a target host, because the transcribed dsRNA is less likely to be perceived as foreign by its host, and will, therefore, be able to initiate RNA degradation of the target host RNA and impart its intended trait. FIG. 14 shows the percent identity determined for the six starting sequences compared to the synthetic sequence. This synthetic gene is then cloned into an appropriate vector, using methods described above, and then used to transform a Petunia plant, plant cell or plant line. The transgene can be engineered by creating a sequence having inverted repeats that lead to the production of a dsRNA upon transcription in the transgenic plant. Without being bound to a theory, a transgene engineered in this way should lead to gene silencing of the endogenous gene, and, in this case, disruption of color development in the transgenic Petunia plant. This synthetic modified Petunia CHS nucleic acid molecule has a nucleotide sequence of SEQ ID NO: 38 as follows:

```
aagctccttg gacttagtcc atcagtcaag cgactaatga tgtaccaaca aggttgcttt    60
gctggtggca ctgtgcttcg attggcaaag gacttggctg agaataacaa aggcgctcga   120
gtccttgttg tgtg                                                      134
```

Example 16

A Synthetic Gene Using Chalcone Synthase Genes in Sorghum

A synthetic sequence was generated according to the present invention to target for degradation different genes of the same gene family in the same plant, this time using the chalcone synthase gene of Sorghum. Sorghum was selected, because it is a grain crop of commercial value and is a representative of the application of the present invention to a monocot. Seven reported sequences for the chalcone synthase gene in Sorghum, shown below in Table 16 along with their GenBank accession numbers, were chosen as starting sequences for analysis.

neered in this way should lead to gene silencing of the endogenous gene, and, in this case, disruption of color development in the transgenic Sorghum plant. The synthetic modified Sorghum CHS nucleic acid molecule has a nucleotide sequence of SEQ ID NO: 47 as follows:

```
cctcaaggag aagttcaaga ggatatgcga caagtcgaag atcaggaagc gttacatgca  60
cttgacggag gagaacctag cggagaaccc caacatatgc gcgtacaggg cgccgtcgct 120
ggacgcccgc caggacatcg tggtggtgga gatacccaag ctaggcgagg ccgcggcgca 180
gaaggcgatc aaagagtggg ggcagccgaa ttccaagatc acgcacctcg tcttctgcac 240
cacctccggc gtcgacatgc ctggcgccga ctaccagctc atcaagatgc t            291
```

TABLE 16

| Plant Species | Gene | GenBank Accession Number |
|---|---|---|
| Sorghum bicolor | chalcone synthase 7 (CHS7) gene | AF152554 |
| Sorghum bicolor | chalcone synthase 6 (CHS6) gene | AF152553 |
| Sorghum bicolor | chalcone synthase 5 (CHS5) gene | AF152552 |
| Sorghum bicolor | chalcone synthase 4 (CHS4) gene | AF152551 |
| Sorghum bicolor | chalcone synthase 3 (CHS3) gene | AF152550 |
| Sorghum bicolor | chalcone synthase 2 (CHS2) gene | AF152549 |
| Sorghum bicolor | chalcone synthase 1 (CHS1) gene | AF152548 |

Figure 15:
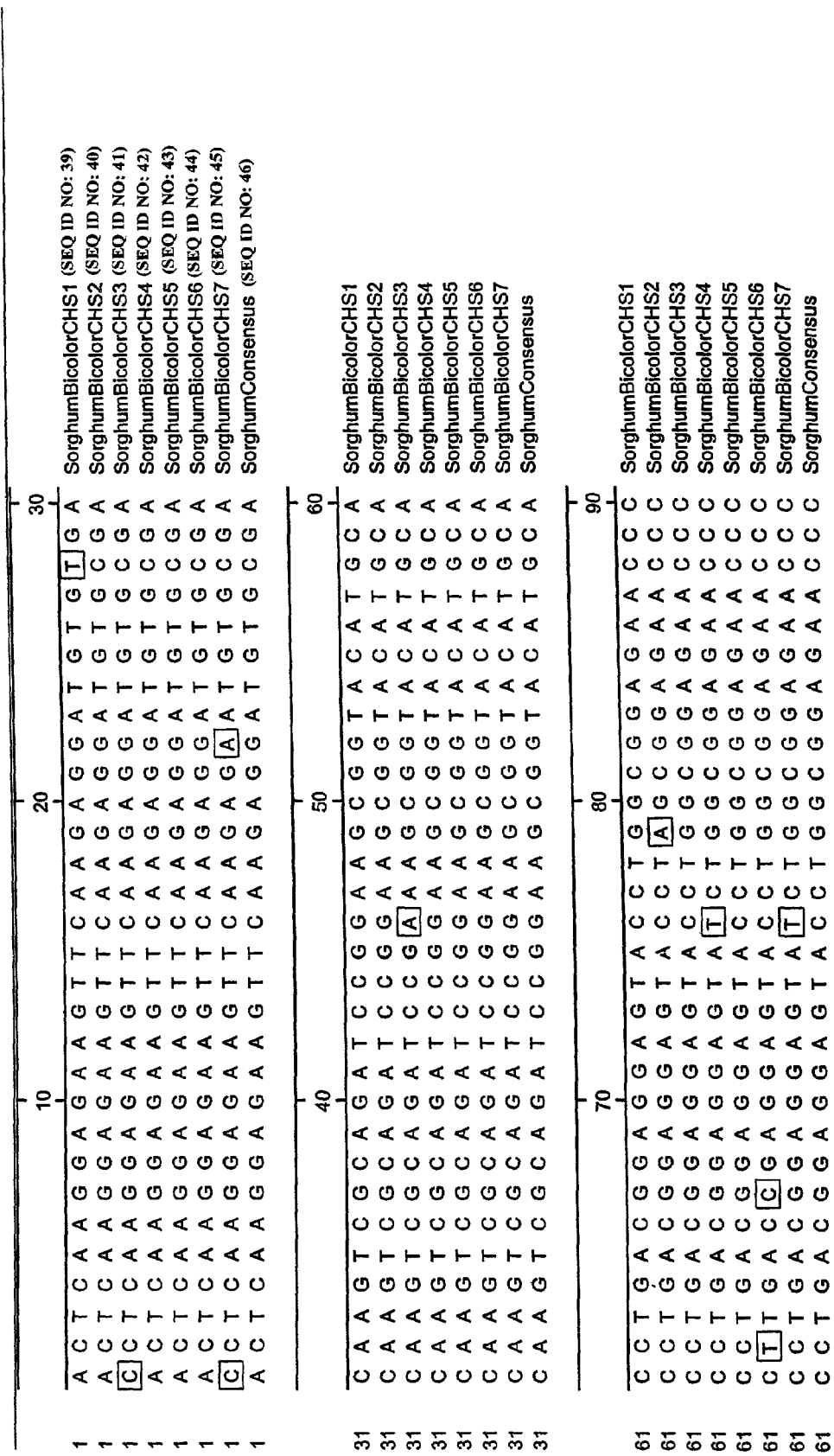
FIG. 15 shows the CLUSTALW alignment of the seven selected Sorghum CHS gene sequences and their consensus sequence (SEQ ID NO: 39–SEQ ID NO: 46) before modification.
Figure 16:
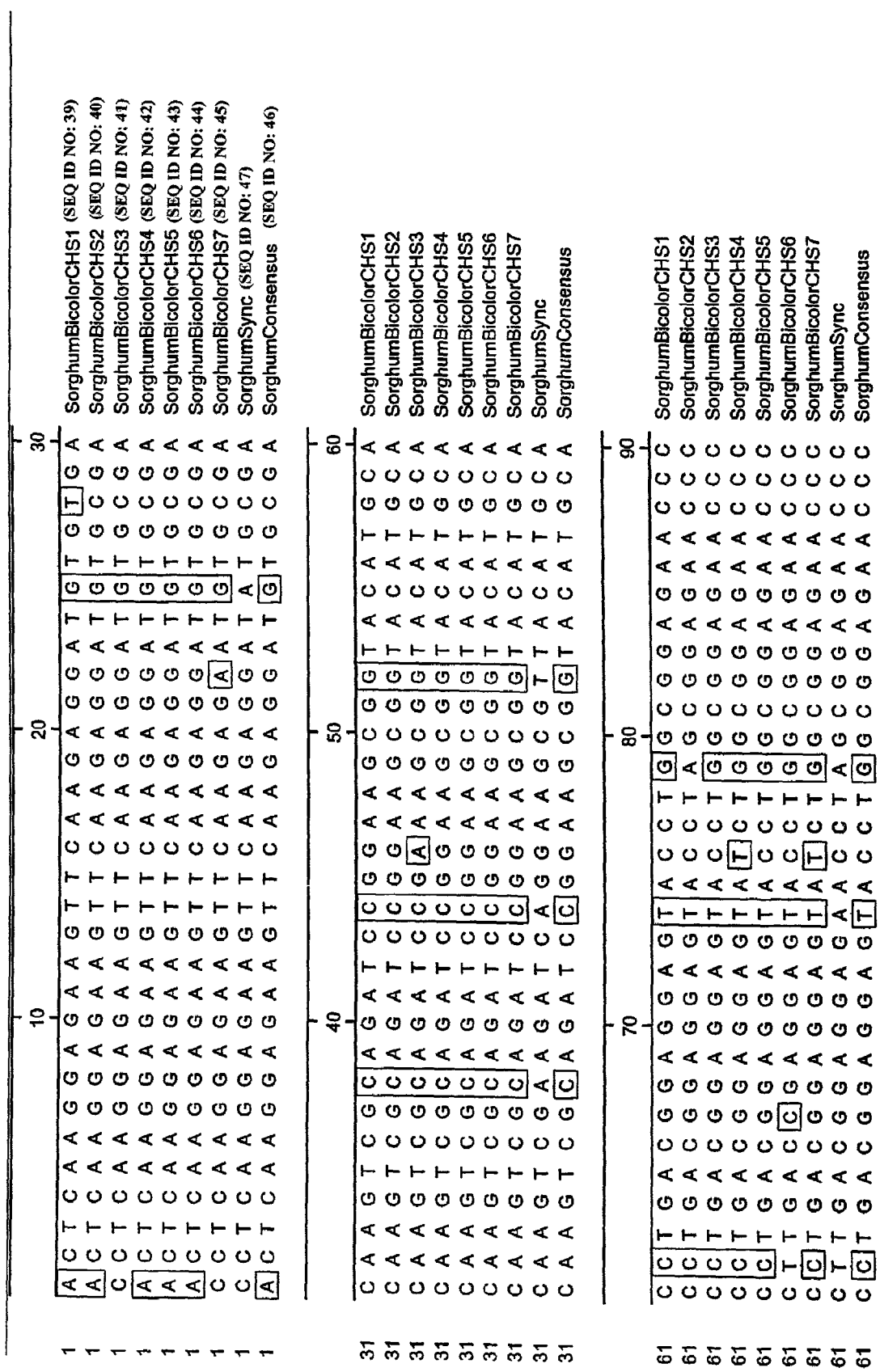
FIG. 16 shows the CLUSTALW alignment of the seven selected Sorghum CHS genes sequences and their consensus sequence from FIG. 15 after modification in comparison to the synthetic modified Sorghum CHS sequence (SEQ ID NO: 47).

The genes of the seven Sorghum CHS genes were compared and analyzed using both ClustalW and MAP for multiple alignment. DNAStar package (LaserGene Software, Madison, Wis.) was used for editing and aligning, and DNAStar and the Blast 2 Sequences from NCBI were used to compare sequences by pairs. To compare the sequence of interest with the GenBank database the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). The alignment of the selected sorghum sequences are shown in FIG. 15. The similarity among the seven sequences was determined to be 95.9–97.9% (range: 2.0%). The similarity with the consensus sequence was determined to be 93.5–99% (range: 5.5%). Using Formula I supra, it was determined the total number of nucleotide changes would be approximately 3. A reference sequence was chosen from among the starting sequences, and nucleotide changes were made by reviewing the alignment data of FIG. 15 and determining those modifications that would result in a single synthetic sequence with a homology of greater than 80, but less than 100% relative to each starting sequence, and which would also result in variation in percent identity of 3% or less. After the nucleotide changes were made the alignment was run again as shown in FIG. 16. The similarity with the synthetic gene was determined to be 91.8–93.1% (range: 1.3%) for all of the starting Sorghum genes. This synthetic gene could then cloned into an appropriate vector, using methods described above, and then used to transform a Sorghum plant, plant cell or plant line. The transgene can be engineered by creating a sequence having inverted repeats that lead to the production of a dsRNA upon transcription in the transgenic plant. Without being bound to a theory, a transgene engi-

Example 17

A Synthetic Sequence to Target the Same Gene Present in Different Plant Species (Same Trait, Different Species) Using ACC-Oxidase Gene in Different Plant Species A synthetic sequence was generated according to the present invention to target for degradation the same gene present in several different plant species. The desired trait is fruit ripening delay in different plant species. Sequences for 20 different genes of the ACC-oxidase gene involved in fruit ripening were used (see Table 17). From different possible 'families', a branch was selected that includes a varied group of plants—some of them of economic value.

TABLE 17

| Plant Species | Gene | GenBank Accession Number |
|---|---|---|
| Actinidia deliciosa | ACC oxidase homologue protein mRNA | M97961 |
| Arabidopsis thaliana | ACC oxidase (ACO2) mRNA | AF016100 |
| Arabidopsis thaliana | At1g12010/F12F1_12 mRNA | AY-052694 |
| Brassica juncea | 1-aminocyclopropane-1-carboxylate oxidase (EFEMR2) mRNA | AF252628 |
| Brassica napus | amino-cyclopropane-carboxylic acid oxidase exons 1–4 | L27664 |
| Brassica oleracea | mRNA for ACC oxidase (ACCOx1) | X81628 |
| Brassica oleracea | mRNA for ACC oxidase (ACCOx2) | X81629 |
| Brassica rapa subsp. rapa | mRNA for ACC oxidase (acoii gene) | AJ309322 |
| Brassica rapa subsp. rapa | mRNA for ACC oxidase (acoi gene) | AJ309321 |
| Carica papaya | ripening-induced ACC oxidase mRNA | AY-077461 |
| Carica papaya | ACC oxidase gene | AF320071 |
| Lycopersicon esculentum | LE-ACO4 mRNA for 1-aminocyclopropane-1-carboxylate oxidase | AB013101 |
| Malus domestica | ACC oxidase gene | X89627 |
| Malus domestica | 1-aminocyclopropane-1-carboxylate oxidase (ACO2) gene | AF015787 |
| Nicotiana glutinosa | ACC oxidase (NGACO3) mRNA | U62764 |
| Nicotiana glutinosa | 1-aminocyclopropane-1-carboxylic acid oxidase (NGACO2) mRNA | U54566 |
| Pisum sativum 1- | aminocyclopropane-1-carboxylate oxidase mRNA | M98357 |
| Pyrus pyrifolia | mRNA for ACC oxidase | D67038 |
| Solanum tuberosum | 1-aminocyclopropane-1-carboxylate oxidase (ACO2) mRNA | AF384821 |
| Vigna radiata | ACC oxidase gene, complete cds | AF315316 |

The genes of the 20 ACC-oxidase genes were compared and analyzed using both ClustalW and MAP for multiple alignment. DNAStar package (LaserGene Software, Madison, Wis.) was used for editing and aligning, and DNAStar and the Blast 2 Sequences from NCBI were used to compare sequences by pairs. To compare the sequence of interest with the GenBank database the Blast program was used (Altschul et al., "Gapped BLAST and PSI-BLAST: A New Generation of Protein Database Search Programs, *Nucleic Acids Research* 35:3389–3402 (1997), which is hereby incorporated by reference in its entirety). The similarity among the 20 sequences was determined to be 73.1–97.7% (range: 24.2%). The similarity with the identified consensus sequence was determined to be 77.3–90.0% (range: 12.7%). Using Formula I supra, it was estimated that approximately 31 nucleotides would need to be modified to create a suitable synthetic gene. A single 260 nt synthetic gene shown below, was designed using the region of high homology within the identified consensus sequence for all the starting ACC sequences, as seen in FIG. 17. FIG. 18 shows the alignment determined for the 20 starting sequences compared to the synthetic sequence. The similarity with the synthetic gene was determined to be 91.8–93.1% (range: 1.3%) for all of the starting genes. The modified nucleotide for this trait, even though derived from a variety of plant species, has an improved homology over that of the consensus sequence compared to the starting sequences, and a significantly improved range of similarity. In accordance with the present invention, this synthetic gene can then be cloned into an appropriate vector, using methods described above, and then used to transform a plurality of different plants, plant cells or plant lines, chosen from among the different plant species from which the starting genes were selected. The transgene can be engineered by creating a sequence having inverted repeats that lead to the production of a dsRNA upon transcription in the transgenic plant. Without being bound to a theory, a transgene engineered in this way should lead to gene silencing of the endogenous gene, and, in this case, disruption of color development in any plant transformed with the synthetic transgene.

This synthetic modified multi-species ACC-oxidase nucleic acid molecule has a nucleotide sequence of SEQ ID NO: 68 as follows:

```
ccagagctga tcaagggcct tcgggctcac acagatgctg gtggcatcat cctgctgttc   60
caagatgaca aggtcagtgg tctccagctt ctcaaagatg gtgattggat tgatgttcct  120
ccaatgaacc actccattgt catcaatctt ggtgaccagc ttgaggtgat taccaatgga  180
aaatacaaga gtgtgatgca ccgtgtgatt gctcagacag atggaaacag aatgtcaata  240
gcatcgttct acaatccggg                                              260
```

Example 18

A Synthetic Sequence to Target for Degradation All Known Isolates of A Single Viral Pathogen Using PRSV CP A synthetic sequence able to target for degradation of all known isolates of PRSV was generated. These isolates come from the Americas, Asia, and the Pacific (i.e., Australia and Hawaii). The desired trait is PRSV resistance in papaya (and probably some cucurbits). Sequences from 47 American isolates, 29 Asian isolates, and 8 from Hawaii and Australia, were used for a total of 84 sequences. These isolates and their accession numbers are shown in Table 18. It has been shown that transgenic papayas are resistant, in most cases, to closely similar strains of the virus (homologous resistance), which creates the unforeseen disadvantage of a potential low durability of transgenic resistance due to mutation or introduction of new variants of PRSV (Tennant et al., "Papaya Ringspot Virus Resistance of Transgenic Rainbow and Sunup is Affected By Gene Dosage, Plant Development, and Coat Protein Homology," *European J. of Plant Pathology* 107:645–653 (2001), which is hereby incorporated by reference in its entirety). On the other hand, due to an extreme dependence on sequence similarity, different transgenic lines should, theoretically, be created for every geographical location in which a different variant of the virus is prevalent to keep the virus under control. Such a task, although apparently pragmatic, would be impractical in terms of cost and labor. Furthermore, many isolates of PRSV have been a source of CP genes that have been already cloned, and most of them sequenced.

TABLE 18

| Geographical Origin | | | GenBank Accession |
|---|---|---|---|
| Country | Isolate | Source | Number |
| Australia | Bridgeman Do. | GenBank | U14736 |
|  | Bundaberg | GenBank | U14737 |
|  | W | GenBank | S89893 |
|  | W, Gatton | GenBank | U14739 |
|  | W, Nort. Terr. | GenBank | U14744 |
|  | P, no name | GenBank | U14738 |
|  | Wellington Po. | GenBank | U14740 |
| Brazil | No name | Gonsalves Lab | Not applicable |
|  | Bahia | GenBank | AF344641 |
|  | Brasilia | GenBank | AF344650 |
|  | W-Brasilia | GenBank | AF344649 |
|  | Ceara | GenBank | AF344647 |
|  | W-Ceara | GenBank | AF344648 |
|  | Espirito Santo | GenBank | AF344644 |
|  | Itabela 1 | GenBank | AF344639 |
|  | Itabela 2 | GenBank | AF344640 |
|  | Paraiba | GenBank | AF344645 |
|  | Parana | GenBank | AF344643 |
|  | Pernambuco | GenBank | AF344646 |
|  | Sao Paulo | GenBank | AF344642 |

TABLE 18-continued

| Geographical Origin | | | GenBank Accession |
|---|---|---|---|
| Country | Isolate | Source | Number |
| China | Severe | GenBank | X96538 |
|  | Vb | GenBank | AF243496 |
| India | AP, partial | GenBank | AF323637 |
|  | Bangalore | GenBank | AF120270 |

TABLE 18-continued

| Geographical Origin | | | GenBank Accession Number |
|---|---|---|---|
| Country | Isolate | Source | |
| | Chiengmai-1 | GenBank | AY010719 |
| | Chiengmai-2 | GenBank | AY010720 |
| | Ratchaburi | GenBank | AY010721 |
| | UP, partial | GenBank | AF323638 |
| | W | GenBank | AF063221 |
| | P, no name | GenBank | AF063220 |
| Indonesia | 1 | GenBank | AF374864 |
| | 2 | GenBank | AF374865 |
| Jamaica | No name | Gonsalves | Not applicable |
| Japan | (Hanada's) | GenBank | E12704 |
| | (Maoka's) | GenBank | AB044339 |
| | Okinawa S, no name | GenBank | D50591 |
| Malaysia | (Maoka's) | GenBank | AB044342 |
| Mexico | Chiapas-11 | GenBank | AJ012650 |
| | Chiapas-30 | GenBank | AY017190 |
| | Chiapas-39 | GenBank | AF319500 |
| | Chiapas-40 | GenBank | AF319501 |
| | Colima | GenBank | AF309968 |
| | Guerrero-9 | GenBank | AY017189 |
| | Jalisco-13 | GenBank | AF319482 |
| | Jalisco-14 | GenBank | AF319483 |
| | Jalisco-39 | GenBank | AF319484 |
| | Michoacan-18 | GenBank | AF319485 |
| | Michoacan-57 | GenBank | AF319486 |
| | Nayarit-22 | GenBank | AF319487 |
| | Oaxaca-27 | GenBank | AF319488 |
| | Oaxaca-66 | GenBank | AF319489 |
| | Oaxaca-80 | GenBank | AF319490 |
| | Quintana Roo-1 | GenBank | AF319491 |
| | Quintana Roo-2 | GenBank | AF319492 |
| | Quintana Roo-3 | GenBank | AF319493 |
| | San Luis Potosi | GenBank | AF319502 |
| | Tabasco-42 | GenBank | AF319503 |
| | Tabasco-43 | GenBank | AF319504 |
| | Tamaulipas-25 | GenBank | AF319494 |
| | Tamaulipas-70 | GenBank | AF319495 |
| | Veracruz-1 | GenBank | AF319497 |
| | Veracruz-6 | GenBank | AJ012649 |
| | Veracruz-7 | GenBank | AF319507 |
| | Veracruz-15 | GenBank | AF319506 |
| | Veracruz-18 | GenBank | AF319498 |
| | Veracruz-Al-18 | GenBank | AF319496 |
| | Veracruz-27 | GenBank | AF319505 |
| | Veracruz-28 | GenBank | AJ012099 |
| | Yucatan | GenBank | AF319499 |
| Sri Lanka | W, no name | GenBank | U14741 |
| Taiwan | (Maoka's) | GenBank | AB044340 |
| | W-Chiayi | GenBank | AY027810 |
| | W-Pintung | GenBank | AY027811 |
| | W-Tainan | GenBank | AY027812 |
| | YK | GenBank | X78557 |
| | YK, complete | GenBank | X97251 |
| Thailand | No name | Gonsalves | Not applicable |
| | Bangkok | GenBank | AY010712 |
| | Chonburi-1 | GenBank | AY010715 |
| | Chonburi-2 | GenBank | AY010716 |
| | Chonburi-3 | GenBank | AF405529 |
| | Chumporn | GenBank | AY010713 |
| | Khon Kaen | GenBank | AY010714 |
| | Nan | GenBank | AF405530 |
| | Nakhon Phat. | GenBank | AF405532 |
| | Nakhon Ratc. | GenBank | AF405531 |
| | Lab. Mild | GenBank | AY010717 |
| | Lab. Severe | GenBank | AY010718 |
| | (Maoka's) | GenBank | AB044340 |
| | W, complete | GenBank | NC_002814 AY010722 |
| | W, partial | GenBank | U14743 |
| United States | Florida | GenBank | AF196839 |
| | Hawaii, HA | GenBank | X67673 |
| | Idem, complete | GenBank | S46722 |
| | Hawaii, revised | GenBank | NC_001785 |
| | Hawaii, Kapoho | Gonsalves | Not applicable |
| | Hawaii, Keaau | Gonsalves | Not applicable |
| | Hawaii, Oahu | Gonsalves | Not applicable |
| | Puerto Rico | GenBank | AF196838 |
| Venezuela | El Vigia | Gonsalves | Not applicable |
| | Lagunillas | Gonsalves | Not applicable |
| Vietnam | W, no name | GenBank | U14742 |

Eighty-four sequences of geographical isolates of PRSV worldwide were analyzed and compared by multiple alignments for the CP gene alone. Given that CP gene sequences have been obtained from different laboratories using different cloning strategies, it was necessary to trim the sequences in order to compare only the region that was available for (and shared by) all of them. After this step, the sequences were once again aligned. DNAStar package was used for editing and aligning, and DNAStar and the Blast 2 Sequences from NCBI were used to compare sequences by pairs. The similarity among the starting sequences was determined to be 79.2–100% (range: 20.8%). The similarity with the consensus was found to be 84.3–99.5% (range: 15.2%).

Figure 19:
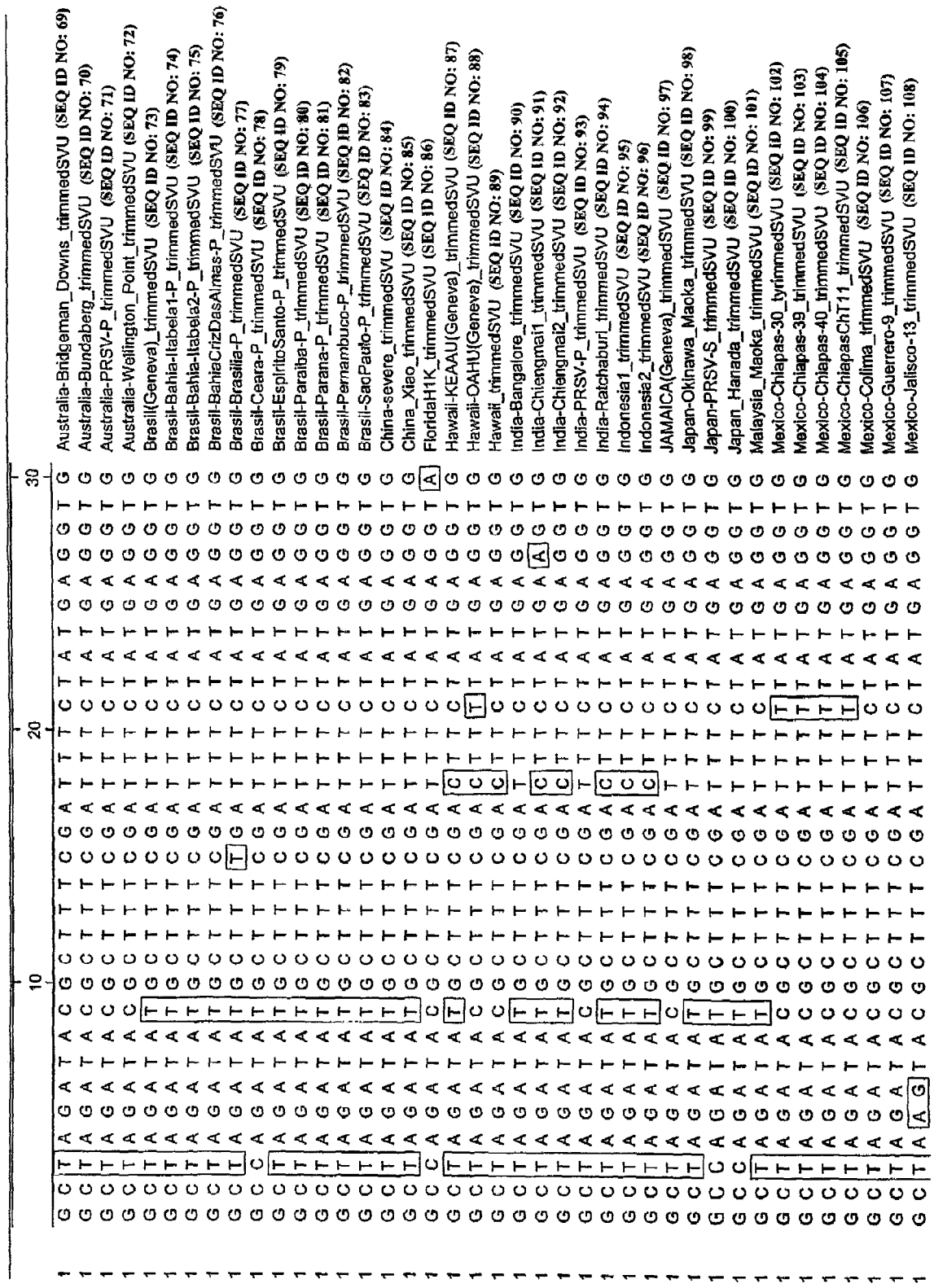
FIG. 19 shows the CLUSTALW alignment of the resulting synthetic modified "Universal" PRSV isolate sequence in comparison with the starting sequences, the consensus sequences, and synthetic gene sequences (SEQ ID NO: 69–SEQ ID NO: 156).

After the sequences were aligned, a potential location of high homology amenable to manipulation was chosen. Using Formula I, supra, it was determined that approximately 20 nucleotides would need to be manipulated to create a suitable synthetic gene. A reference sequence was chosen and nucleotides modified until a 216 nt nucleic acid molecule was determined to be suitable for gene silencing of all 84 PRSV isolates. FIG. 19 shows the CLUSTALW alignment of the resulting synthetic "Universal" PRSV isolate sequence. Sequence similarity analysis with the synthetic gene was 89.8–93.5% (range: 3.7%) compared to all starting sequences. The homology of the synthetic sequence relative to the starting sequences, was lower than the maximum homology of the starting sequences, but was above the lower limits of similarity found for the consensus sequence relative to the starting sequences. The synthetic nucleic acid also had a narrow range of variation in similarity compared to all starting sequences (i.e., 0.8%) compared to a range of 10.5% variation in similarity among the native starting sequences. This combination of homology greater than 80% and a narrow range of variation make the Petunia synthetic nucleic acid molecule a good candidate for degrading RNA in a target host because the transcribed dsRNA is less likely to be perceived as foreign by its host, and will therefore be able to initiate RNA degradation of the target host RNA and impart its intended trait. This universal PRSV synthetic molecule has a nucleotide sequence of SEQ ID NO: 156 as follows:

```
gccagatacg ctttcgattt ctatgaggtg aattcaaaaa cacctgatag agctcgtgaa   60
gctcacacgc agatgaaagc tgcagcactg cgtaacacta atcycagaat gtttggaatg  120
gacggcagtg tcagtaacaa agaagaaaac acagaaagac acacagtgga agatgtaaac  180
agagacatgc actctctcct gggtatgcgc aactga                            216
```

Additionally, the CP genes were analyzed in smaller geographic groupings. All isolates from North and South American countries (excluding those from Hawaii) were grouped as "the Americas." The starting sequences within this group were aligned using CLUSTALW, and DNAStar and the Blast 2 Sequences from NCBI were used to compare sequences by pairs. This analysis showed a similarity among starting sequences of 91.7–100% (range: 8.3%), with a similarity of 94–100% (range: 6.0%) for the starting sequences compared to the consensus sequence. A reference sequence was chosen from a region of high homology and select nucleotides were manipulated. Using Formula I, supra, it was determined that approximately 20 nucleotides would need to be manipulated to create a suitable synthetic gene. The modified sequence was aligned with the starting sequences numerous times until a modified 216 nt synthetic "universal" nucleic acid molecule for the combined "Americas" isolates was determined to be suitable. The final CLUSTALW alignment is shown in FIG. 20. The final homology analysis resulted in a similarity of 93.1–94.9% (range: 1.8%) with the synthetic gene compared to all starting sequences. The modified sequence had a degree of homology over 90%, with a much improved range of variation in similarity values over those of the starting sequences or even the consensus sequence. The "universal Americas" PRSV synthetic molecule has a nucleotide sequence of SEQ ID NO: 153 as follows:

```
gccagatacg cttttgattt ctatgaggtg aattcaaaaa cacctgatag agctcgtgaa   60
gctcacatgc agatgaaggc tgcagcgctg cgaaacacta atcgtagaat gtttggtatg  120
gacggcagtg ttagcaacaa tgaagaaaac acggagagac acacagtgga agatgtcaat  180
agagacatgc actctctcct gggtatgcgc aactaa                            216
```

All isolates from Asia were grouped as "Asia." The starting sequences within this group were aligned using CLUSTALW, and DNAStar and the Blast 2 Sequences from NCBI were used to compare sequences by pairs. This analysis showed a similarity of 80.6–99.5% (range: 18.9%) among starting sequences and a similarity of 84.3–99.5% (range: 15.2%) for the starting sequences compared to the consensus sequence. A reference sequence was chosen from a region of high homology and select nucleotides were manipulated as described above. Using Formula I, supra, it was determined that approximately 20 nucleotides would need to be manipulated to create a suitable synthetic gene. The modified sequences were aligned numerous times until a final 216 nt synthetic "universal" nucleic acid molecule for the combined "Asia" isolates was determined to be suitable. The final CLUSTALW alignment is shown in FIG. 21. The final homology analysis showed a similarity of 89.9–93.1% (range: 3.2%) with the synthetic gene compared to all starting sequences. The modified Asia sequence has a fairly high degree of homology, well over the 80% minimum. Striking here is the variation in the range of similarity, which was improved significantly from that among the starting sequences themselves (18.9%). While the modifications in this trait group were halted when the values shown here were reached, it is highly probable that the 3.2% variance in homology can be further reduced with additional manipulations. This "universal Asia" PRSV synthetic molecule has a nucleotide sequence of SEQ ID NO: 154 as follows:

```
gccagatatg ctttcgattt ctatgaagtg aattcaaaaa cacctgatag agctcgtgaa   60
gctcacatgc agatgaaagc tgcagcactg cgtaacgcta atcgcagaat gtttggaatg  120
gacggcactg tcagtaacaa agaagaaaac acagaaagac acacagtgga agatgtaaac  180
agagacatgc aatctctcct gggtatgcgc aactga                            216
```

All isolates from Australia and Hawaii were grouped as the "Pacific" isolates. The sequences within each of these groups were aligned using the CLUSTALW, and DNAStar and the Blast 2 Sequences from NCBI were used to compare sequences by pairs. This analysis showed a similarity among starting sequences of 96.8–99.5% (range: 2.7%), with the similarity of 96.8–100% (range 2.7%) for the starting sequences compared to the consensus sequence. Following alignment, a potential location amenable to manipulation was chosen. In this case, due to the high similarity value among the starting sequences (96.8–99.5%), only about 4 nts are required for manipulation in order to create a suitable modified synthetic nucleic acid molecule. A reference sequence was selected, manipulated, and aligned, and a modified 216 nt synthetic "universal" nucleic acid molecule was determined to be suitable for gene silencing of PRSV isolates within the Asia geographic group. The final CLUSTALW alignment is shown in FIG. 22. The similarity with the synthetic gene was determined to be 97.7–98.1% (range: 0.4%) compared to all starting sequences. The modified sequence of this trait group has a high homology value that is very similar to each of the starting sequences (0.4% variation), which is an improvement over the native starting sequences themselves, and in comparison to the consensus sequence. This trait group is an example that the present invention can create a molecule with improved range of variation in similarity values, even from a trait group which exhibits high native homology. This "universal Pacific" PRSV synthetic molecule has a nucleotide sequence of SEQ ID NO: 155 as follows:

```
gctagatatg ctttcgattt ttatgaggtg aattcgaaaa cacctgatag ggctcgcgaa    60
gctcacatgc agatgaaagc tgcagcgctg cgaaacacta gtcgcagaat gtttggtatg   120
gacggcagtg ttagtaacaa ggaagaaaac acggagagac acacagtgga agatgtcaat   180
agagacatgc actctctcct gggtatgcgc aactaa                              216
```

All of the "universal" synthetic sequences of the present invention can be used to prepare DNA constructs of the present invention, as described above, that are capable of producing transcribed dsRNA of the nucleic acid sequence in the plant, plant cell or plant line transformed with the construct, thereby effecting gene silencing and imparting the trait of resistance to multiple strains of PRSV, a devastating pathogen of *Carica papaya* worldwide.

Fusing multiple synthetic modified genes in a single transgene may result in a single construct able to trigger gene silencing and resistance against all isolates of PRSV. For example, the Universal synthetic nucleic acid molecule could be combined in a single construct with the synthetic molecule for the Americas; or all three universal geographic synthetic sequences could be combined in a single transgene. With the PCR assembly strategy (Stemmer et al., "Single-Step Assembly of a Gene and Entire Plasmid From Large Numbers of Oligodeoxyribonucleotides," *Gene* 164: 49–53 (1985), which is hereby incorporated by reference in its entirety) that was already successfully used with the N gene of different tospoviruses as explained above, it highly likely that such a transgene would be effective.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A DNA construct comprising:
   a modified nucleic acid molecule having a nucleotide sequence which is at least 80%, but less than 100%, homologous to two or more desired trait DNA molecules from a viral plant pathogen and which achieves post-transcriptional gene silencing of the homologous desired trait DNA molecules when transcribed in plants, thereby imparting the desired trait to plants transformed with said DNA construct, wherein each of the desired trait DNA molecules relative to the modified nucleic acid molecule have a nucleotide sequence similarity value and each of these similarity values differs by no more than 3 percentage points, and wherein the desired trait is viral resistance in plants.

2. The DNA construct according to claim 1, wherein the modified nucleic acid has the nucleotide sequence of SEQ ID NO: 4.

3. The DNA construct according to claim 1 further comprising:

a promoter sequence and a termination sequence, wherein the promoter sequence and the termination sequence are operatively coupled to said modified nucleic acid molecule.

4. The DNA construct according to claim 1, wherein said modified nucleic acid molecule encodes an RNA molecule which is translatable.

5. The DNA construct according to claim 1, wherein said modified nucleic acid molecule encodes an RNA molecule which is non-translatable.

6. The DNA construct according to claim 1, wherein said the trait DNA molelcule is a viral plant pathogen gene or fragment thereof from a plant viral genome.

7. The DNA construct according to claim 6, wherein the trait DNA molecule derived from a plant viral genome is selected from the group consisting of a DNA molecule encoding a coat protein, a DNA molecule encoding replicase, a DNA molecule not encoding a protein, a DNA molecule encoding a viral gene product, and combinations thereof.

8. The DNA construct according to claim 6, wherein the trait DNA molecule is derived from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

9. The DNA construct according to claim 1, wherein each of the desired trait DNA molecules relative to the modified nucleic acid molecule have a nucleotide sequence similarity value and each of these similarity values differs by no more than 2 percentage points.

10. The DNA construct according to claim 1, wherein each of the desired trait DNA molecules relative to the modified nucleic acid molecule have nucleotide sequence similarity value and each of these similarity values differs by 1 percentage point or less.

11. A DNA expression vector comprising the DNA construct according to claim 1.

12. A host cell transformed with the DNA construct of claim 1, wherein the cell is a bacterial cell or a plant cell.

13. The host cell according to claim 12, wherein the cell is a plant cell.

14. The transgenic plant transformed with the DNA construct according to claim 1.

15. A transgenic plant according to claim 14, wherein the modified nucleic acid molecule has a nucleotide sequence which is at least 80%, but less than 100%, homologous to a plurality of desired trait DNA molecules, wherein each of the desired trait DNA molecules relative to the modified nucleic acid molecule have a nucleotide sequence similarity value and each of these similarity values differs by no more than 2 percentage points.

16. The transgenic plant according to claim 14, wherein the trait DNA molecules are viral plant pathogen genes or fragments thereof from a plant viral genome.

17. The transgenic plant according to claim 16, wherein said trait DNA molecules are selected from the group consisting of a DNA molecule encoding a coat protein, a DNA molecule encoding a replicase, a DNA molecule not encoding a protein, a DNA molecule encoding a viral gene product, and combinations thereof.

18. The transgenic plant according to claim 16, wherein the trait DNA molecules from a plant virus are selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, a DNA molecule not encoding a protein, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

19. The transgenic plant according to claim 14 further comprising:
a promoter sequence and
a termination sequence, wherein the promoter sequence and the termination sequence are operatively coupled to said modified nucleic acid.

20. The transgenic plant according to claim 14, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinnia.

21. A transgenic plant seed transformed with the DNA construct according to claim 1.

22. The transgenic plant seed according to claim 21, wherein said modified nucleic acid molecule has a nucleotide sequence which is at least 80%, but less than 100%, homologous to a plurality of desired trait DNA molecules, wherein each of the desired trait DNA molecules relative to the modified nucleic acid molecule have a nucleotide sequence similarity value and each of these similarity values differs by 2 percentage points or less.

23. The transgenic plant seed according to claim 22, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinnia.

24. A DNA construct comprising:
a plurality of modified nucleic acid molecules, wherein each modified nucleic acid molecule has a nucleotide sequence which is at least 80%, but less than 100%, homologous to two or more desired trait DNA molecules from a viral plant pathogen, wherein said plurality of modified nucleic acid molecules acheives post-transcriptional gene silencing of the homologous desired trait DNA molecules, thereby collectively imparting a plurality of traits to plants transformed with said DNA construct, and wherein the desired trait DNA molecules relative to their respective modified nucleic acid molecule have a nucleotide sequence similarity value and each of these similarity values differs by no more than 3 percentage points, and wherein the desired trait is viral resistance to more than one virus in plants.

25. The DNA construct according to claim 24, wherein the desired trait DNA molecules relative to their respective modified nucleic acid molecule have a nucleotide sequence similarity value and each of these similarity values differs by no more than 2 percentage points.

26. The DNA construct according to claim 24, wherein the desired trait DNA molecules relative to their respective modified nucleic acid molecule have a nucleotide sequence similarity value and each of these similarity values differs by no more than 1 percentage point.

27. The DNA construct according to claim 24, wherein at least one of the modified nucleic acid molecules has the nucleotide sequence of SEQ ID NO: 4.

28. The DNA construct according to claim 24, wherein the trait DNA molecules are viral pathogen genes or fragments thereof from a plant viral genome.

29. The DNA construct according to claim 28, wherein said trait DNA molecules from a plant viral genome are selected from the group consisting of a DNA molecule encoding a coat protein, a DNA molecule encoding replicase, a DNA molecule not encoding a protein, a DNA molecule encoding a viral gene product, and combinations thereof.

30. The DNA construct according to claim 28, wherein the trait DNA molecules are from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

31. The DNA construct according to claim 24 further comprising:

a promoter sequence and a termination sequence, wherein the promoter sequence and the termination sequence are operatively coupled to said plurality of modified nucleic acid molecules.

32. The DNA construct according to claim 24, wherein at least some of said modified nucleic acid molecules encode RNA molecules which are translatable.

33. The DNA construct according to claim 24, wherein at least some of said modified nucleic acid molecules encode RNA molecules which are nontranslatable.

34. An expression vector comprising the DNA construct according to claim 24.

35. A host cell transformed with the DNA construct of claim 24, wherein the cell is a bacterial cell or a plant cell.

36. The host cell according to claim 35, wherein the cell is a plant cell.

37. A transgenic plant transformed with the DNA construct of claim 24.

38. The transgenic plant according to claim 37, wherein the modified nucleic acid molecules have a nucleotide sequence which is at least 80%, but less than 100%, homologous to two or more desired trait DNA molecules and wherein each of the desired trait DNA molecules relative to their respective modified nucleic acid molecule have a nucleotide sequence similarity value and each of these similarity values differs by no more than 2 percentage points.

39. The transgenic plant according to claim 37, wherein each of the trait DNA molecules are viral plant pathogens genes or fragments thereof from a plant viral genome and the trait is viral disease resistance.

40. The transgenic plant according to claim 39, wherein said trait DNA molecules from a plant viral genome are selected from the group consisting of a DNA molecule encoding a coat protein, a DNA molecule not encoding a protein, a DNA molecule encoding a viral gene product, and combinations thereof.

41. The transgenic plant according to claim 39, wherein said trait DNA molecules are from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, a DNA molecule not encoding a protein, tomato mottle virus and tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

42. The transgenic plant according to claim 37 further comprising:
a promoter sequence and
a termination sequence, wherein the promoter sequence and the termination sequence are operatively coupled to the plurality of modified nucleic acid molecules.

43. The transgenic plant according to claim 37, wherein at least some of said modified nucleic acid molecules encode RNA molecules which are translatable.

44. The transgenic plant according to claim 37, wherein at least some of said modified nucleic acid molecules encode RNA molecules which are non-translatable.

45. The transgenic plant according to claim 37, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinnia.

46. A transgenic plant seed transformed with the DNA construct according to claim 24.

47. The transgenic plant seed according to claim 46, wherein each of the modified nucleic acid molecules have a nucleotide sequence which is at least 80%, but less than 100%, homologous to two or more of desired trait DNA molecules and wherein each of the desired trait DNA molecules relative to their respective modified nucleic acid molecule have a nucleotide sequence similarity value and each of these similarity values differs by no more than 2 percentage points.

48. The transgenic plant seed according to claim 46, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinnia.

49. A method of imparting viral resistance to plants comprising:
transforming a plant with a DNA construct according to claim 1.

50. The method according to claim 49, wherein each of the desired trait DNA molecules relative to the modified nucleic acid molecule have a nucleotide sequence similarity value and each of these similarity values differs by no more than 2 percentage points.

51. The method according to claim 49, wherein each of the desired trait DNA molecules relative to the modified nucleic acid molecule has a nucleotide sequence similarity values which differ by no more than 1 percentage point.

52. The method according to claim 49, wherein the trait DNA molecule is viral plant pathogen or fragment thereof from a plant viral genome.

53. The method according to claim 52, wherein said trait DNA molecule from a plant viral genome is selected from the group consisting of a DNA molecule encoding a coat protein, a DNA molecule encoding a replicase, a DNA molecule not encoding a protein, a DNA molecule encoding a viral gene product, and combinations thereof.

54. The method according to claim 52, wherein said trait DNA molecule is from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, a DNA molecule not encoding a protein, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

55. The method according to claim 49 further comprising:
propagating progeny of the transgenic plant.

56. A method of imparting viral resistance to plants comprising:

planting a transgenic plant seed according to claim 21 and growing a plant from the planted transgenic plant seed.

57. A method of imparting viral resistance to plants comprising:

transforming a plant with a DNA construct according to claim 24.

58. The method according to claim 57, wherein said modified nucleic acid molecules have a nucleotide sequence which is at least 80%, but less than 100%, homologous to two or more desired trait DNA molecules, and wherein each of the desired trait DNA molecules relative to the modified nucleic acid molecule have a nucleotide sequence similarity value and each of these similarity values differs by no more than 2 percentage points.

59. The method according to claim 57, wherein the trait DNA molecules are viral plant pathogen genes or fragments thereof from a plant viral genome.

60. The method according to claim 59, wherein said trait DNA molecules from a plant viral genome are selected from the group consisting of a DNA molecule encoding a coat protein, a DNA molecule encoding a replicase, a DNA molecule which does not encode a protein, a DNA molecule encoding a viral gene product, and combinations thereof.

61. The method according to claim 59, wherein the trait DNA molecules from a plant virus are selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

62. The method according to claim 57 further comprising:

propagating progeny of the transgenic plants wherein the progeny comprise said DNA construct.

63. A method of imparting viral resistance to plants comprising:

planting the transgenic plant seed according to claim 46 and growing a plant from the planted transgenic plant seed.

64. A DNA construct comprising a first nucleic acid molecule having a nucleotide sequence which is at least 80%, but less than 100%, homologous to two or more desired trait DNA molecules from a viral plant pathogen, and which has a length that is insufficient to independently impart a desired trait to plants transformed with said DNA construct, wherein each of the desired trait DNA molecules relative to the first nucleic acid molecule have a nucleotide sequence similarity value and each of these similarity values differs by no more than 3 percentage points, and wherein the desired trait is viral resistance in plants; and a second DNA molecule, operatively coupled to the first nucleic acid molecule, wherein said first nucleic acid molecule and said second DNA molecule collectively achieve post-transcriptional silencing of the homologous desired trait DNA molecules from a viral plant pathogen, thereby imparting viral resistance to plants transformed with said DNA construct.

65. The DNA construct according to claim 64 further comprising:

a promoter sequence and a termination sequence, wherein the promoter sequence and the termination sequence are operatively coupled to the first and the second DNA molecules.

66. The DNA construct according to claim 64, wherein the first nucleic acid has the nucleotide sequence of SEQ ID NO: 4.

67. The DNA construct according to claim 64, wherein the trait DNA molecule is a viral plant pathogen gene or fragment thereof from a plant viral genome.

68. The DNA construct according to claim 67, wherein said second DNA molecule is selected from the group consisting of a viral cDNA molecule, a jellyfish green fluorescence protein encoding DNA molecule, and a plant DNA molecule.

69. The DNA construct according to claim 67, wherein the trait DNA molecules are from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

70. The DNA construct according to claim 64, wherein the trait DNA molecules are selected from the group consisting of a DNA molecule encoding a coat protein, a DNA molecule encoding replicase, a DNA molecule not encoding a protein, a DNA molecule encoding a viral gene product, and combinations thereof.

71. The DNA construct according to claim 64, wherein the trait DNA molecules are from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

72. The DNA construct according to claim 64, wherein each of the desired trait DNA molecules relative to the modified nucleic acid molecule has a nucleotide sequence similarity value and each of these similarity values differs by 1 percentage point or less.

73. The DNA construct according to claim 64, further comprising:

a plurality of first DNA molecules operatively coupled to a second DNA molecule, wherein each operatively coupled first and second DNA molecule imparts resistance to a different virus when transcribed in plants.

74. The DNA construct according to claim 73, wherein the first DNA molecules have a nucleotide sequence which is at least 80%, but less than 100%, homologous to a plurality of desired trait DNA molecules, and wherein the desired trait DNA molecules relative to the respective first DNA molecule have a nucleotide sequence similarity value and each of these similarity values differs by no more than 3 percentage points.

75. The DNA construct according to claim 73, wherein the trait DNA molecules from a viral plant pathogen are selected from the group consisting of a DNA molecule encoding a coat protein, a DNA molecule encoding replicase, a DNA molecule not encoding a protein, a DNA molecule encoding a viral gene product, and combinations thereof.

76. A DNA expression vector comprising the DNA construct according to claim 64.

77. A host cell transformed with the DNA construct according to claim 64, wherein the cell is a bacterial cell or a plant cell.

78. The host cell according to claim 77, wherein the cell is a plant cell.

79. A transgenic plant transformed with the DNA construct according to claim 64.

80. The transgenic plant according to claim 79, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinma.

81. A transgenic plant seed transformed with the DNA construct according to claim 64.

82. The transgenic plant seed according to claim 81, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, *Arabidopsis thaliana, Saintpaulia,* petunia, pelargonium, poinsettia, chrysanthemum, carnation, and zinnia.

83. A method of imparting viral resistance to plants comprising:
    transforming a plant with the DNA construct according to claim 64.

84. The method according to claim 83, wherein each of the desired trait DNA molecules relative to the modified nucleic acid molecule have a nucleotide sequence similarity value and each of these similarity values differs by no more than 2 percentage points.

85. The method according to claim 83, wherein each of the desired trait DNA molecules relative to the modified nucleic acid molecule have a nucleotide sequence similarity value and each of these similarity values differs by no more than 1 percentage point.

86. The method according to claim 83, wherein the trait DNA molecule is a viral plant pathogen gene or fragment thereof from a plant viral genome.

87. The method according to claim 86, wherein said trait DNA molecule from a plant viral genome is selected from the group consisting of a DNA molecule encoding a coat protein, a DNA molecule encoding a replicase, a DNA molecule not encoding a protein, a DNA molecule encoding a viral gene product, and combinations thereof.

88. The method according to claim 86, wherein said trait DNA molecule is from a plant virus selected from the group consisting of tomato spotted wilt virus, impatiens necrotic spot virus, groundnut ringspot virus, potato virus Y, potato virus X, tobacco mosaic virus, turnip mosaic virus, tobacco etch virus, papaya ringspot virus, a DNA molecule not encoding a protein, tomato mottle virus, tomato yellow leaf curl virus, arabis mosaic virus, grapevine rupestris stem pitting associated virus-1, rupestris stem pitting associated virus-1, grapevine leafroll-associated virus 3, grapevine leafroll-associated virus 4, grapevine leafroll-associated virus 8, grapevine leafroll-associated virus 1, grapevine leafroll-associated virus 5, grapevine leafroll-associated virus 7, grapevine leafroll-associated virus 2, grapevine virus A, grapevine trichovirus B, grapevine virus B, and combinations thereof.

89. The DNA construct according to claim 1, further comprising a second nucleic acid molecule coupled to the modified nucleic acid molecule, wherein the modified nucleic acid molecule and the second nucleic acid molecule achieve post-transcriptional silencing of the homologous desired trait DNA molecules when transcribed in plants, and impart the desired trait to plants transformed with said DNA construct.

90. The DNA construct according to claim 89 further comprising:
    a promoter sequence and
    a termination sequence, wherein the promoter sequence and the termination sequence are operatively coupled to the modified nucleic acid molecule and the second nucleic acid molecule.

91. The DNA construct according to claim 89, wherein the second nucleic acid molecule is selected from the group consisting of a viral cDNA molecule, a jellyfish green fluorescence protein encoding DNA molecule, and a plant DNA molecule.

* * * * *